US012369852B2

(12) United States Patent
Toth et al.

(10) Patent No.: US 12,369,852 B2
(45) Date of Patent: Jul. 29, 2025

(54) CONTROLLED AND PRECISE TREATMENT OF CARDIAC TISSUES

(71) Applicant: Autonomix Medical, Inc., Excelsior, MN (US)

(72) Inventors: Landy Toth, Doylestown, PA (US); Robert Schwartz, Inver Grove Heights, MN (US)

(73) Assignee: Autonomix Medical, Inc., Ivyland, PA (US)

( * ) Notice: Subject to any disclaimer, the term of this patent is extended or adjusted under 35 U.S.C. 154(b) by 959 days.

(21) Appl. No.: 17/501,502

(22) Filed: Oct. 14, 2021

(65) Prior Publication Data

US 2022/0104762 A1 Apr. 7, 2022

Related U.S. Application Data

(63) Continuation of application No. 15/769,184, filed as application No. PCT/US2016/057875 on Oct. 20, 2016, now Pat. No. 11,154,239.

(Continued)

(51) Int. Cl.
*A61B 5/00* (2006.01)
*A61B 5/02* (2006.01)
(Continued)

(52) U.S. Cl.
CPC .......... *A61B 5/4839* (2013.01); *A61B 5/0215* (2013.01); *A61B 5/282* (2021.01);
(Continued)

(58) Field of Classification Search
CPC ..... A61B 5/4839; A61B 5/282; A61B 5/0215; A61B 5/4848; A61B 5/6858;
(Continued)

(56) References Cited

U.S. PATENT DOCUMENTS

| 4,380,237 A | 4/1983 | Newbower |
| 5,261,889 A | 11/1993 | Laine et al. |

(Continued)

FOREIGN PATENT DOCUMENTS

| AU | 2010207062 B2 | 5/2015 |
| AU | 2014233285 A1 | 9/2015 |

(Continued)

OTHER PUBLICATIONS

Extended European Search Report for European Patent Application No. 16858201.3, dated Sep. 3, 2019. 11 pages.

(Continued)

*Primary Examiner* — Patrick Fernandes
(74) *Attorney, Agent, or Firm* — Ryan, Mason & Lewis, LLP

(57) ABSTRACT

Systems, devices, and methods for performing precise treatment, mapping, and/or testing of tissues are disclosed. Systems, devices, and methods for administering an agent to one or more a precise regions within a tissue mass are disclosed. Systems, devices, and methods for treating targeted regions within a tissue mass are disclosed. Systems, devices, and methods for identifying, localizing, monitoring neural traffic in the vicinity of, quantifying neural traffic in the vicinity of, and mapping neural traffic near targeted regions within a tissue mass are disclosed.

20 Claims, 17 Drawing Sheets

Related U.S. Application Data

(60) Provisional application No. 62/244,322, filed on Oct. 21, 2015.

(51) Int. Cl.

| | | |
|---|---|---|
| *A61B 5/0205* | (2006.01) | |
| *A61B 5/0215* | (2006.01) | |
| *A61B 5/08* | (2006.01) | |
| *A61B 5/1473* | (2006.01) | |
| *A61B 5/20* | (2006.01) | |
| *A61B 5/282* | (2021.01) | |
| *A61B 5/287* | (2021.01) | |
| *A61B 5/316* | (2021.01) | |
| *A61B 5/352* | (2021.01) | |
| *A61B 18/00* | (2006.01) | |
| *A61B 18/14* | (2006.01) | |
| *A61N 1/36* | (2006.01) | |

(52) U.S. Cl.
CPC .......... *A61B 5/4848* (2013.01); *A61B 5/6858* (2013.01); *A61B 5/6869* (2013.01); *A61B 18/1492* (2013.01); *A61N 1/36135* (2013.01); *A61B 5/0059* (2013.01); *A61B 5/02028* (2013.01); *A61B 5/0205* (2013.01); *A61B 5/08* (2013.01); *A61B 5/1473* (2013.01); *A61B 5/201* (2013.01); *A61B 5/287* (2021.01); *A61B 5/316* (2021.01); *A61B 5/352* (2021.01); *A61B 2018/00351* (2013.01); *A61B 2018/00577* (2013.01); *A61B 2018/00702* (2013.01); *A61B 2018/00839* (2013.01); *A61B 2505/05* (2013.01); *A61B 2562/0247* (2013.01); *A61B 2562/0261* (2013.01); *A61B 2576/023* (2013.01)

(58) Field of Classification Search
CPC ... A61B 5/6869; A61B 18/1492; A61B 5/352; A61B 5/287; A61B 5/316; A61B 5/0059; A61B 5/02028; A61B 5/0205; A61B 5/08; A61B 5/1473; A61B 5/201; A61B 2018/00351; A61B 2018/00577; A61B 2018/00702; A61B 2018/00839; A61B 2505/05; A61B 2562/0247; A61B 2562/0261; A61B 2576/023; A61N 1/36135

See application file for complete search history.

(56) References Cited

U.S. PATENT DOCUMENTS

| | | | |
|---|---|---|---|
| 6,129,725 A * | 10/2000 | Tu | A61B 18/1492 606/49 |
| 6,466,817 B1 | 10/2002 | Kaula et al. | |
| 7,177,677 B2 | 2/2007 | Kaula et al. | |
| 7,865,236 B2 | 1/2011 | Cory et al. | |
| 7,885,700 B2 | 2/2011 | Clark et al. | |
| 8,097,926 B2 | 1/2012 | De Graff et al. | |
| 8,320,990 B2 | 11/2012 | Vij | |
| 8,536,667 B2 | 9/2013 | De Graff et al. | |
| 8,702,857 B2 | 4/2014 | Venema et al. | |
| 8,706,219 B2 | 4/2014 | Feldman et al. | |
| 8,712,549 B2 | 4/2014 | Zdeblick et al. | |
| 9,031,647 B2 | 5/2015 | Maskara et al. | |
| 9,131,864 B2 | 9/2015 | Korenberg | |
| 9,186,060 B2 | 11/2015 | De Graff et al. | |
| 9,295,842 B2 | 3/2016 | Ghaffari et al. | |
| 9,326,816 B2 | 5/2016 | Srivastava | |
| 9,339,332 B2 | 5/2016 | Srivastava | |
| 9,629,586 B2 | 4/2017 | Ghaffari et al. | |
| 9,662,069 B2 | 5/2017 | De Graff et al. | |
| 9,750,421 B2 | 9/2017 | Ghaffari et al. | |
| 9,801,557 B2 | 10/2017 | Ghaffari et al. | |
| 9,820,673 B2 | 11/2017 | Feldman et al. | |
| 9,931,047 B2 | 4/2018 | Srivastava | |
| 10,186,546 B2 | 1/2019 | De Graff et al. | |
| 10,271,898 B2 | 4/2019 | Cao et al. | |
| 10,292,610 B2 | 5/2019 | Srivastava | |
| 10,426,545 B2 | 10/2019 | Asirvatham et al. | |
| 10,737,123 B2 | 8/2020 | Sullivan et al. | |
| 10,918,298 B2 | 2/2021 | Rogers et al. | |
| 11,058,484 B2 | 7/2021 | Asirvatham et al. | |
| 11,515,029 B2 | 11/2022 | Sullivan et al. | |
| 11,540,775 B2 | 1/2023 | Shachar et al. | |
| 2002/0138075 A1 * | 9/2002 | Edwards | A61N 1/06 606/41 |
| 2005/0090761 A1 * | 4/2005 | Carney | A61B 5/01 600/549 |
| 2005/0261672 A1 | 11/2005 | Deem et al. | |
| 2007/0282254 A1 | 12/2007 | Chow | |
| 2008/0027346 A1 * | 1/2008 | Litt | A61N 1/36053 600/544 |
| 2009/0054803 A1 | 2/2009 | Saadat et al. | |
| 2010/0298895 A1 | 11/2010 | Ghaffari et al. | |
| 2011/0034912 A1 * | 2/2011 | de Graff | H01L 27/14687 606/41 |
| 2012/0017804 A1 | 1/2012 | Venema et al. | |
| 2012/0157804 A1 | 6/2012 | Rogers et al. | |
| 2013/0303876 A1 | 11/2013 | Gelfand et al. | |
| 2014/0088554 A1 | 3/2014 | Li et al. | |
| 2014/0180028 A1 * | 6/2014 | Burkett | A61B 5/02152 600/585 |
| 2014/0236103 A1 | 8/2014 | Fischell et al. | |
| 2014/0275993 A1 | 9/2014 | Ballakur | |
| 2015/0065945 A1 * | 3/2015 | Zarins | A61B 18/04 514/183 |
| 2015/0119674 A1 | 4/2015 | Fischell et al. | |
| 2015/0190194 A1 | 7/2015 | Weber et al. | |
| 2017/0188942 A1 | 7/2017 | Ghaffari et al. | |
| 2018/0078169 A1 | 3/2018 | Feldman et al. | |
| 2019/0069949 A1 | 3/2019 | Vrba et al. | |
| 2020/0337765 A1 | 10/2020 | Smith | |
| 2020/0375541 A1 | 12/2020 | Shachar et al. | |
| 2021/0307824 A1 | 10/2021 | Asirvatham et al. | |
| 2022/0047202 A1 | 2/2022 | Shachar et al. | |
| 2023/0057437 A1 | 2/2023 | Sullivan et al. | |

FOREIGN PATENT DOCUMENTS

| | | |
|---|---|---|
| AU | 2013230893 B2 | 12/2015 |
| AU | 2013305279 B2 | 7/2017 |
| AU | 2015358385 B2 | 9/2020 |
| CA | 2934245 A1 | 7/2015 |
| CA | 2969129 A1 | 6/2016 |
| CA | 2749024 C | 10/2016 |
| CN | 203138452 U | 8/2013 |
| CN | 102292395 B | 7/2014 |
| CN | 103284693 B | 12/2014 |
| CN | 103271766 B | 8/2015 |
| CN | 105828709 A | 8/2016 |
| CN | 106068105 A | 11/2016 |
| CN | 105120785 B | 11/2017 |
| CN | 107802341 B | 7/2020 |
| CN | 105658163 B | 8/2020 |
| CN | 111700677 A | 9/2020 |
| DK | 2389415 T3 | 11/2014 |
| EP | 1451595 B1 | 7/2009 |
| EP | 2389415 B1 | 8/2014 |
| EP | 2513953 B1 | 10/2017 |
| EP | 3038555 B1 | 7/2018 |
| EP | 2986243 B1 | 6/2020 |
| EP | 3226795 B1 | 8/2020 |
| EP | 2887900 B1 | 12/2020 |
| EP | 2967713 B1 | 12/2020 |
| EP | 3799815 A1 | 4/2021 |
| EP | 3038556 B1 | 5/2021 |
| EP | 3884897 A1 | 9/2021 |
| EP | 4144294 A1 | 3/2023 |
| ES | 2329773 T3 | 12/2009 |
| ES | 2523498 T3 | 11/2014 |

(56) References Cited

FOREIGN PATENT DOCUMENTS

| | | |
|---|---|---|
| JP | 2006509547 A | 3/2006 |
| JP | 5405706 B2 | 2/2014 |
| JP | 5681117 B2 | 3/2015 |
| JP | 5694947 B2 | 4/2015 |
| JP | 2016534842 A | 11/2016 |
| JP | 2017502752 A | 1/2017 |
| JP | 6109863 B2 | 4/2017 |
| JP | 2017148514 A | 8/2017 |
| JP | 6204616 B2 | 9/2017 |
| JP | 2017536187 A | 12/2017 |
| JP | 6574134 B2 | 9/2019 |
| KR | 101590005 B1 | 1/2016 |
| KR | 20160106582 A | 9/2016 |
| KR | 101743628 B1 | 6/2017 |
| NL | 2002442 C2 | 7/2010 |
| WO | 2001093759 A1 | 12/2001 |
| WO | 2003048789 A2 | 6/2003 |
| WO | 2004052182 A2 | 6/2004 |
| WO | 2006044868 A1 | 4/2006 |
| WO | 2007136491 A1 | 11/2007 |
| WO | 2010030373 A2 | 3/2010 |
| WO | 2010082993 A2 | 7/2010 |
| WO | 2010085140 A1 | 7/2010 |
| WO | 2011084450 A1 | 7/2011 |
| WO | 2011093991 A1 | 8/2011 |
| WO | 2013134479 A1 | 9/2013 |
| WO | 2014029355 A1 | 2/2014 |
| WO | 2014051705 A1 | 4/2014 |
| WO | 2014070999 A2 | 5/2014 |
| WO | 2014089553 A1 | 6/2014 |
| WO | 2014160832 A2 | 10/2014 |
| WO | 2014172398 A1 | 10/2014 |
| WO | 2015031643 A1 | 3/2015 |
| WO | 2015031648 A1 | 3/2015 |
| WO | 2015057696 A1 | 4/2015 |
| WO | 2015061457 A1 | 4/2015 |
| WO | 2015102951 A2 | 7/2015 |
| WO | 2015103541 A1 | 7/2015 |
| WO | 2016090175 A1 | 6/2016 |
| WO | PCT/US2016/057875 | 1/2017 |
| WO | 2020242753 A1 | 12/2020 |
| WO | 2023038682 A1 | 3/2023 |
| WO | 2023038748 A1 | 3/2023 |

OTHER PUBLICATIONS

China Second Office Action for China Patent Application No. 201680068094.3, dated May 28, 2021, 14 pages.

\* cited by examiner

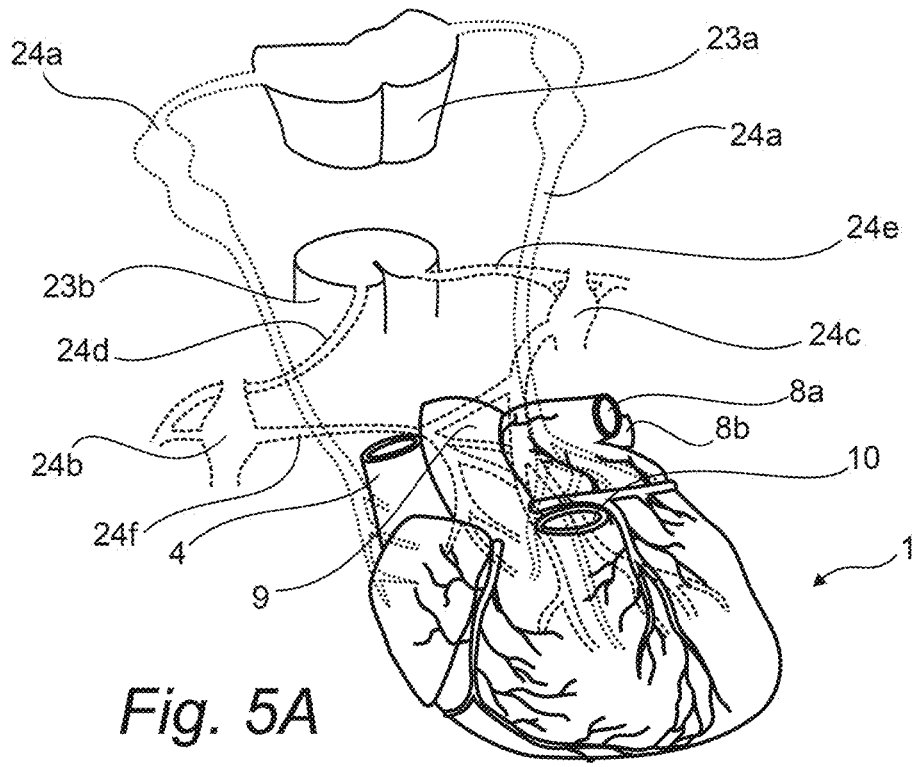
Fig. 5A
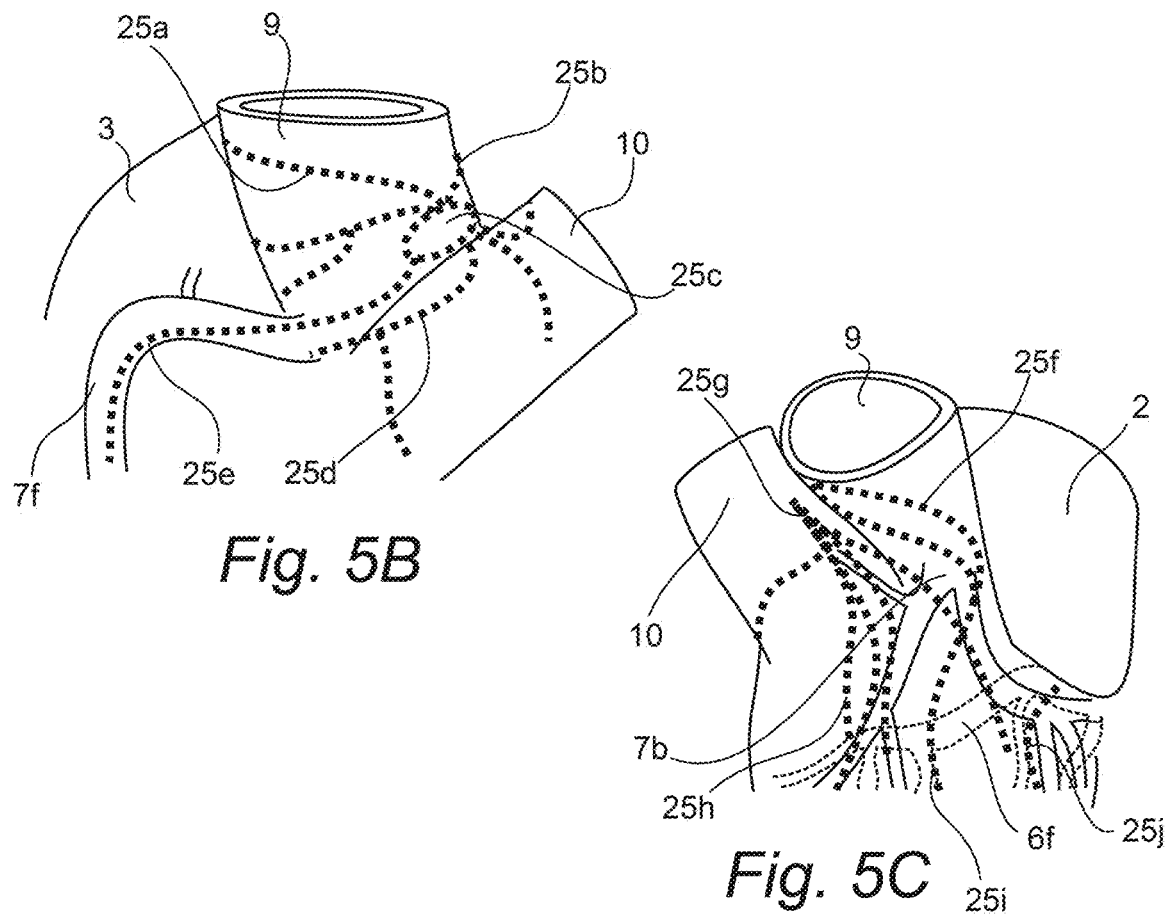
Fig. 5B
Fig. 5C

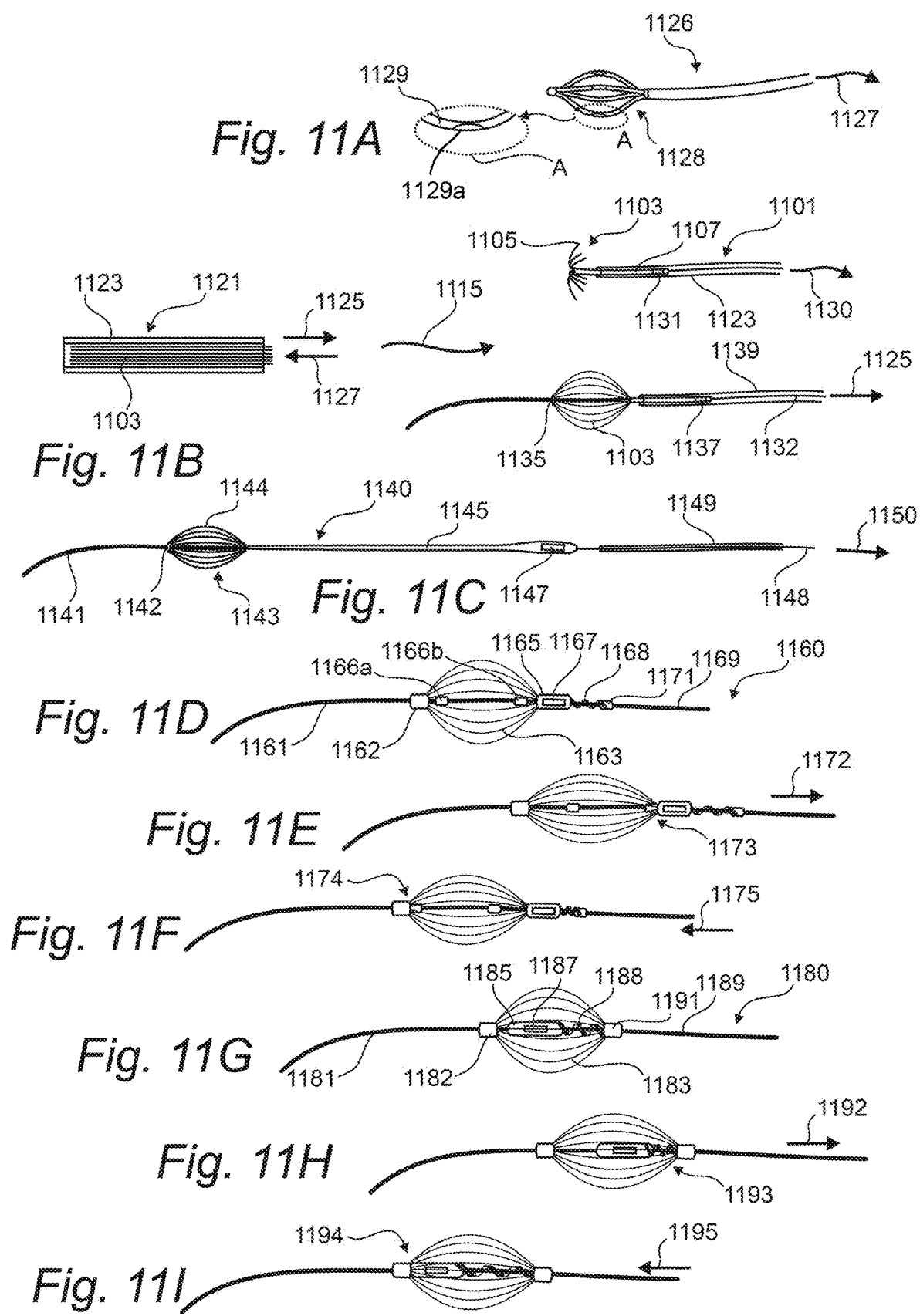

PRIOR ART

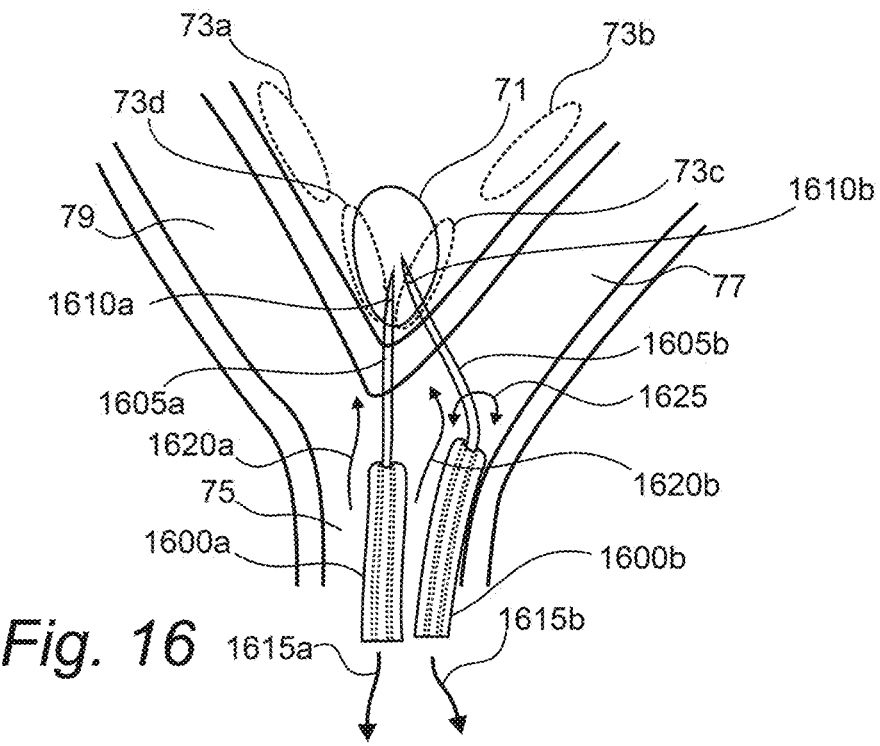
Fig. 16
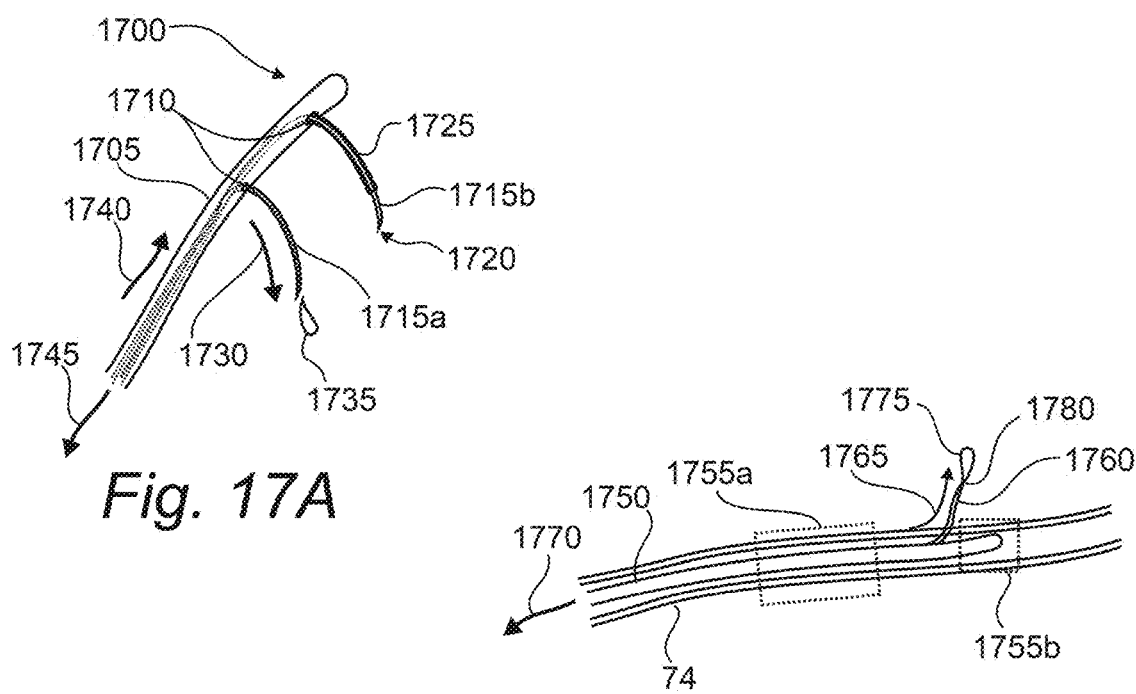
Fig. 17A
Fig. 17B

CONTROLLED AND PRECISE TREATMENT OF CARDIAC TISSUES

CROSS-REFERENCE TO RELATED APPLICATIONS

The present application is a continuation of U.S. patent application Ser. No. 15/768,184, filed Apr. 18, 2018, which is a national stage of International Application PCT/US2016/057875, filed Oct. 20, 2016, which claims the benefit of and priority to U.S. Provisional Application Ser. No. 62/244,322, filed on Oct. 21, 2015 and entitled "Controlled and Precise Treatment of Cardiac Tissues," by Landy Toth et al., the entire contents of which are incorporated by reference herein for all purposes.

BACKGROUND

Technical Field

The present disclosure relates to interventional monitoring, detection, mapping, and diagnostic/therapeutic feedback of autonomic and cardiac electrophysiologic signals and function. The present disclosure relates to systems, devices, and methods for performing feedback driven neuromodulation, denervation, and/or ablation of tissues.

Background

There are several disease states wherein ablation, neuromodulation, or functional change in a tissue is desired. Such disease states include pain management, arrhythmia treatments, neuroendocrine disorders, autoimmune disorders, lower urinary tract symptoms (LUTS), central nervous system disorders, and cancer.

Relating to cardiac diseases, the autonomic nervous system plays a major role in regulating and maintaining normal cardiac activity. However, it frequently also plays a major role in pathologic disease states.

A majority of cardiac disease is treated by sympathetic beta-receptor blockade. This includes ischemia (acute and chronic), angina (ischemic chest pain), arrhythmias (supraventricular or ventricular), heart failure including both systolic and diastolic dysfunction, coronary artery spasm and its pain.

Cardiac parameters as well govern blood pressure and hypertension which is an effect of the interaction between peripheral vascular resistance/impedance, myocardial contractility, cardiac stroke volume, and ventricular ejection time.

Beta receptor blockade by pharmacologic agents include specific, non-specific, and ISA agents, which by virtue of their systemic dosing affect all cells and cardiac structures (cardiac muscle, conduction tissues and tracts, pacemaker cells, cardiac stroma) indiscriminately and simultaneously.

The indiscriminate and global effects of systemic beta blockade leads to clinical problems whereby therapy of one function causes dysfunction of another. For example, beta blockade for heart failure (ventricular muscle cells) leads to severe bradyarrhythmias.

Systemic beta blockade as well affects all cells and organs of the body, often leading to unwanted and intolerable side effects (e.g., depression, impotence, lassitude, fatigue, etc.).

There is a need to treat such disease states with fewer complications.

SUMMARY

One illustrative, non-limiting objective of this disclosure is to provide methods for interventional treatment of cardiac muscle and coronary vessels. Another illustrative, non-limiting objective of this disclosure is to provide a tool for monitoring, evaluating the function of, mapping, and/or modulating electrophysiological activity in the vicinity of a lumen within a body. Yet another illustrative, non-limiting objective is to provide systems and methods for evaluating the extent of a neuromodulation procedure such as a neuromodulating ablation and/or stimulation. Another objective is to provide systems and methods for modifying lymphatic structures and the function or integrity thereof in a body.

According to a first aspect there is provided, a microsurgical tool for monitoring electrophysiological activity within the vicinity of a lumen, the microsurgical tool including a microfinger in accordance with the present disclosure having a substantially elongate structure configured so as to bias a region thereof against a wall of the lumen upon deployment within the lumen, and a sensing tip in accordance with the present disclosure electrically and mechanically coupled to the microfinger in the vicinity of the region, configured to interface with the wall of the lumen, the sensing tip configured to convey one or more electrophysiological signals associated with the activity.

In aspects, one or more of the electrophysiological signals may be related to one or more of water concentration, tone, evoked potential, remote stimulation of nervous activity, an electromyographic signal [EMG], a mechanomyographic signal [MMG], a local field potential, an electroacoustic event, vasodilation, vessel wall stiffness, muscle sympathetic nerve activity (MSNA), central sympathetic drive (e.g., bursts per minute, bursts per heartbeat, etc.), tissue tone, nerve traffic (e.g., post ganglionic nerve traffic in the peroneal nerve, celiac ganglion, superior mesenteric ganglion, aorticorenal ganglion, renal ganglion, and/or related nervous system structures), combinations thereof, or the like.

In aspects, one or more of the sensing tips may include one or more electrodes, a needle electrode, a force sensor, mechanomyographic (MMG) sensing element, a strain sensor, a compliance sensor, a temperature sensor, combinations thereof, or the like each in accordance with the present disclosure. In aspects, one or more sensing tips may be electrically coupled with a microcircuit, the microcircuit configured to condition the signal.

In aspects, a system/surgical tool in accordance with the present disclosure may be used to access, monitor, and/or to treat one or more sensory receptors: Ampullae of Lorenzini (respond to electric field, salinity, temperature, etc.), baroreceptors, chemoreceptors, hydroreceptors, mechanoreceptors, nociceptors, osmoreceptors (osmolarity sensing), photoreceptors, proprioceptors, thermoreceptors, combinations thereof, and the like.

According to aspects there is provided, an elongate medical device including one or more sensing tips each in accordance with the present disclosure. The elongate medical device may be configured for placement within a vessel, for delivery to or within the parenchyma of an organ into which the vessel extends.

In aspects, the elongate medical device may be a guidewire configured for nerve monitoring, electrophysiological monitoring, stimulation, and/or ablation procedures.

In aspects, a guidewire in accordance with the present disclosure may be configured to provide a path over which a second surgical tool may be delivered to the vessel, the guidewire sensing tip configured to monitor one or more physiologic functions relevant to the operation and/or evaluation of a procedure performed by the surgical tool.

In aspects, a guidewire and/or sensing tip in accordance with the present disclosure may be dimensioned and configured for placement into the parenchyma of an organ, a renal cortex of a kidney, an adrenal gland, a vessel connected with the adrenal gland, an adrenal medulla, and/or a renal pelvis of a kidney.

In aspects, a guidewire in accordance with the present disclosure may include a plurality of zones arranged along the length thereof, each zone configured for sensing local electrophysiological activity, stimulating local neural anatomy, and/or neuromodulating local neural anatomy (e.g., ablating, denervating, etc.). In aspects, a guidewire in accordance with the present disclosure may include a sensing zone located at the distal tip thereof, an ablating/stimulating zone located along the length of the guidewire proximally to the distal tip, and a second sensing zone located along the length of the guidewire proximally to the ablating/stimulating zone. In aspects, functions performed within each zone during a procedure may be coordinated by a controller in accordance with the present disclosure for purposes of diagnosis, determining the extent of a procedure, performing a neuromodulation procedure, denervating a neural structure, combinations thereof, or the like.

In aspects, a guidewire in accordance with the present disclosure may be sized with a diameter of less than 1 mm, less than 0.75 mm, less than 0.5 mm, less than 0.25 mm, etc. In aspects, the guidewire may be configured with a shape set region, configured to bias one or more regions of the guidewire against a wall of a lumen into which it has been placed. In aspects, the guidewire may include a wire basket, a helical region, a balloon, etc. in order to provide such bias against an adjacent lumen wall. In aspects, the shape set region may be retractably collapsible into a delivery sheath (i.e., a sheath provided over the guidewire sized and dimensioned for delivery thereof to an anatomical site of interest). In aspects, the shape set region may be deployed so as to bias against a wall of a lumen into which it is placed by an actuation procedure, retraction of a delivery sheath, protrusion of the guidewire distal tip beyond the distal tip of a delivery sheath, etc.

In aspects, a guidewire in accordance with the present disclosure may include a bulbous feature located within the vicinity of the distal tip thereof, the bulbous feature configured to bottom out the guidewire within a lumen (e.g., when the lumen diameter approaches that of the bulbous feature, between a step between a feeding lumen and a treatment lumen, etc.). Such a feature may be advantageous to position the distal tip of the guidewire within a treatment lumen (e.g., a vessel, an artery, a vein, a tubule, etc.), to provide hemostasis to the treatment lumen, etc.

In aspects, a guidewire in accordance with the present disclosure may include a microelectronic circuit embedded within or coupled to the distal tip thereof, as well as coupled to an interconnect and/or controller coupled to the proximal end thereof, configured to control signal flow to/from one or more zones of the guidewire for purposes of performing a procedure in accordance with the present disclosure.

According to aspects there is provided, a method for treating an anatomical site within a body, including imaging the anatomical site (e.g., with a computed tomography system, high-resolution computed tomography (HRCT), magnetic resonance imaging (MRI), functional magnetic resonance imaging (fMRI), positron emission tomography, ultrasound, optical coherence tomography (OCT), combinations thereof, or the like) to produce one or more images (e.g., 2D images, 3D images, etc.) thereof, guiding a guidewire, device, and/or aspects of a system in accordance with the present disclosure to within the vicinity of the anatomical site (optionally in combination with the images), and performing a procedure, and/or treating the anatomical site (e.g., via ablation, chemical delivery, energy delivery, etc.). In aspects, the procedure may include sensing one or more physiologic aspects of the anatomical site and/or a bodily process related thereto, stimulating the anatomical site, etc.

In aspects, a method in accordance with the present disclosure may include advancing a guidewire in accordance with the present disclosure until it "bottoms out" against the walls of the lumen including and/or coupled to the anatomical site.

In aspects, a method in accordance with the present disclosure may include releasing a chemical substance in accordance with the present disclosure into, through the wall of, and/or into the adventitia around a lumen coupled with the anatomical site, and/or associated organ.

In aspects, a method in accordance with the present disclosure may include monitoring one or more physiologic processes with the distal tip of a guidewire in accordance with the present disclosure, before, during, and/or after the release of the chemical substance. The method may include assessing the efficacy of a procedure (e.g., ablation, chemical release, chemical ablation, RF ablation, ultrasound ablation, hypothermic ablation, radiosurgical ablation, etc.). In aspects, the method may include inducing a temporary neural block, monitoring the effects of the temporary neural block, and/or creating a substantially long term neural block depending on the monitoring.

In aspects, a guidewire in accordance with the present disclosure may include one or more electrodes, each electrode configured to sense, stimulate, and/or ablate a local anatomical site within a body. In aspects, the guidewire may include a plurality of ablation electrodes configured to interface with a wall of a lumen into which the guidewire is placed, so as to provide coupling for delivery of radiofrequency, and/or microwave frequency energy into the wall of the lumen and/or tissues surrounding the lumen, as part of a procedure in accordance with the present disclosure. In aspects, the guidewire may be configured to monitor one or more physiologic aspects in conjunction with the energy delivery process (e.g., before, during, after, etc.).

In aspects, a system in accordance with the present disclosure may include a delivery catheter including one or more electrodes, and a guidewire including one or more electrodes, the system configured to pass energy between the catheter electrode(s) and the guidewire electrode(s) as part of a procedure. In aspects, the system may be configured to monitor electrophysiological activity between the guidewire electrode(s) and the catheter electrode(s) as part of a procedure.

In aspects, a guidewire in accordance with the present disclosure may include a drug eluting region (e.g., over an electrode, at the distal tip, etc.), configured so as to elute a drug into the vicinity of the region during a procedure (e.g., so as to minimize clotting, minimize damage to adjacent structures, etc.).

In aspects, a guidewire in accordance with the present disclosure may include a thrombus net coupled to the distal tip thereof. The thrombus net may be configured so as to bridge a cross section of a lumen into which the guidewire is placed during a procedure. The thrombus net may be configured to capture debris generated at a site along the system, guidewire, associated catheter, etc. during a procedure in accordance with the present disclosure. The thrombus net may be configured so as to withdraw any captured debris along with the guidewire during withdrawal from the body.

In aspects there is provided a guidewire for monitoring electrophysiological activity in the vicinity of an anatomical site of interest within the vicinity of a lumen within a body, the guidewire including an elongate body dimensioned for insertion into the lumen, and a sensing tip electrically and mechanically coupled to the elongate body, configured to interface with the wall of the lumen, the sensing tip configured to convey one or more electrophysiological signals associated with the activity.

In aspects, the sensing tip may include one or more sensors and/or electrodes each in accordance with the present disclosure. The sensor and/or electrode may be dimensioned and configured to interface with the anatomical site of interest upon placement thereby.

In aspects, the sensing tip may include one or more sensors configured to measure one or more electrophysiological signals related to one or more of water concentration, tone, evoked potential, extracellular potentials, remote stimulation of nervous activity, an electromyographic signal [EMG], a mechanomyographic signal [MMG], a local field potential, an electroacoustic event, vasodilation, vessel wall stiffness, muscle sympathetic nerve activity (MSNA), muscle activity, cardiac muscle potentials, smooth muscle action potentials, central sympathetic drive, tissue tone, nerve traffic, combinations thereof, or the like.

In aspects, a sensing tip in accordance with the present disclosure may be dimensioned for placement into the parenchyma of an organ coupled with the lumen (e.g., into a liver, a prostate, a pancreas, a spleen, a bladder, a prostate, a ganglion, a gland, into a renal cortex of a kidney, an adrenal gland, an adrenal medulla, an adrenal cortex, and/or a renal pelvis of a kidney, combinations thereof, or the like).

In aspects, the sensing tip may be configured such that the sensor and/or the electrode included therein may be substantially isolated from a fluid within the lumen upon deployment of the sensing tip within the lumen, maintains contact with a wall of the lumen during a procedure upon deployment of the sensing tip within the lumen, substantially maintains contact with the wall of the lumen while the sensing tip is dragged along the interior thereof, after deployment of the sensing tip within the lumen, and/or may be embedded into a wall of the lumen upon deployment of the sensing tip within the lumen.

In aspects, the guidewire may be coupled to a second surgical device, the second surgical device configured to perform an ablation, stress, and/or stimulation procedure within the body.

In aspects, the second surgical device may include a reference electrode electrically coupled with one or more of the sensors and/or electrodes included within the guidewire.

In aspects, a guidewire in accordance with the present disclosure may include a microcircuit coupled to the sensing tip, configured to convey one or more sensed physiologic signals to a proximal end of the guidewire, to condition the signal, to perform a digital conversion of the signal, to multiplex signals from a plurality of sensors and/or electrodes within the guidewire.

In aspects, a guidewire in accordance with the present disclosure may include one or more electrodes electrically and mechanically coupled with the elongate body, configured to deliver energy to the anatomical site of interest upon placement thereby.

In aspects, the guidewire may include one or more microneedles slidingly coupled with the elongate body, configured so as to be deployed beyond the elongate body into the anatomical site of interest upon placement thereby. Such a microneedle may include a lumen through which a substance may be delivered to the anatomical site of interest upon deployment of the microneedle there into. Some non-limiting examples of substances include a neurotoxin, a cancer treating agent, a neuroblocking agent, a neurostimulating agent, a neurodepressant, a vasodilator, a vasoconstrictor, glucose, insulin, a combination thereof, a formulation of the substance with a delivery vehicle, or the like.

In aspects, one or more of the microneedles may include one or more electrodes for sensing, stimulating, and/or ablating the anatomical site of interest upon deployment of the microneedle there into.

According to aspects there is provided, use of a guidewire in accordance with the present disclosure, to monitor electrophysiological activity in the vicinity of a vessel, an artery, a vein, a renal artery, a hepatic artery, or the like.

According to aspects there is provided, use of a guidewire in accordance with the present disclosure to monitor electrophysiological activity in the parenchyma of an organ, a kidney, a renal cortex, a gland, an adrenal gland, a liver, a pancreas, a spleen, a prostate, or a renal pelvis, an arteriole, venule, or vesicle associated therewith, or the like.

According to aspects there is provided, use of a guidewire in accordance with the present disclosure to perform and/or monitor a neuromodulation procedure.

According to aspects there is provided, use of a guidewire in accordance with the present disclosure, to evaluate a sympathetic and/or parasympathetic activity level associated with an organ, a process associated with the organ, or a region thereof within a body.

According to aspects there is provided, a system for neuromodulating an anatomical site in the vicinity of a lumen or along the wall of a chamber, including a subsystem configured to perform a surgical procedure on the anatomical site, a guidewire in accordance with the present disclosure, configured to monitor electrophysiological activity within the parenchyma of an organ coupled to the lumen and to generate one or more signals therefrom, and a control unit configured to accept signals from the guidewire, and to adjust the surgical procedure dependent upon the signals, to display the signals (e.g., to an operator, a subject, a client, etc.), to evaluate the surgical procedure dependent upon the signals, to plan a surgical path dependent upon the signals, and/or to determine the extent of the procedure dependent upon the signals, or the like.

In aspects, the surgical procedure may an ablation, an excision, a cut, a burn, a radio frequency ablation, radiosurgery, an ultrasonic ablation, a cryoablation, an abrasion, a biopsy, delivery of a substance, a combination thereof, or the like.

In aspects, the system may include a stimulation and/or ablation electrode configured so as to convey a pulsatile and/or radio frequency signal to the anatomical site from the control unit, the guidewire configured to convey one or more feedback signals related to the pulsatile and/or radio frequency signals back to the control unit. Such feedback signals may be related to electrode impedance, a bioimpedance, a local electrical field, or an electrophysiological response to the pulsatile and/or radio frequency signal, or the like. In aspects, the stimulation and/or ablation electrode may be included within the guidewire and/or a sensing tip thereof.

In aspects, the subsystem may be situated coaxially with the guidewire in the lumen.

In aspects, the system may include a sensor to measure one or more physiologic signals associated with a body comprising the lumen, and to convey the physiologic signals to the control unit for use in the procedure. The sensor may be configured to measure one or more of water concentration, tone, blood oxygen saturation of local tissues, evoked potential, stimulation/sensing of nervous activity, electromyography, temperature, blood pressure, vasodilation, vessel wall stiffness, muscle sympathetic nerve activity (MSNA), central sympathetic drive, tissue tone, blood flow, a blood flow differential signal, blood perfusion, pupil dilation, electrolyte levels in a biofluid, a blood analyte level, nerve traffic, a combination thereof, or the like.

According to aspects there is provided, a method for evaluating sympathetic tone of a subject including, recording electrophysiological signals from a lumen and/or from one or more sites within an organ of the subject, and generating a metric relating to sympathetic tone from the recorded signals.

In aspects the recording may be at least partially facilitated by a guidewire in accordance with the present disclosure.

The method may include applying a stress test to the subject during the recording. The stress test may include having the subject perform a valsalva maneuver, a tilt table test, elevating one or more legs, transient sitting to standing exercises, execute a change in posture, move from a prone position to a sitting or standing position, a breath hold technique, or combinations thereof. In aspects, the stress test may include injecting into the subject a vasodilator, a vasoconstrictor, a neuroblocker, a neurostimulant, a diuretic, insulin, glucose, beta-adrenergic receptor antagonist, angiotensin-ll converting enzyme inhibitor, calcium channel blocker, an HMG-CoA reductase inhibitor, digoxin, an anticoagulant, a diuretic, a beta blocker, an ACE inhibitor, a steroid, combination thereof, or the like. In aspects, such an injection may be made into the lumen and/or into the organ. In aspects, the injection may be performed at least in part by a guidewire in accordance with the present disclosure.

In aspects the metric may be generated from recordings taken while the subject is awake or asleep, assessment while awake versus under anesthesia, before, during and/or after electrostimulation at one or more sites on the subject, combinations thereof, or the like. In aspects, the stress test may include having the subject perform a physical activity, altering the blood volume of the subject, altering the heartbeat of the subject, injecting a quantity of saline into the subject, or a combination thereof.

In aspects, the method may include evaluating how the activity responds to the stress test, comparing the response to a previous stress test performed on the subject, comparing the response to a population average response to the stress test, comparing aspects within a single stress test, comparing the activity before and after a procedure, comparing the activity between a resting state and an active state, comparing activity between an awakened state and a sleeping state, or combinations thereof.

In aspects, the method may include neuromodulating one or more anatomical sites within the subject.

The method may include inserting a balloon catheter into a lumen coupled to the organ and temporarily blocking the lumen, applying a polarizing potential to one or more sites in the organ and/or the lumen wall, monitoring another physiologic parameter remotely from the lumen to generate a corrective signal and using the corrective signal to remove movement artifacts from the electrophysiological signals, stimulating one or more anatomical sites in the subject during the recording, and/or diagnosing a medical condition based at least in part upon the metric.

According to aspects there is provided, a method for determining the properties of one or more neurological features in the vicinity of one or more monitoring sites, including monitoring one or more of water concentration, tone, blood oxygen saturation of local tissues, evoked potential, stimulation/sensing of nervous activity, electromyography, temperature, blood pressure, vasodilation, vessel wall stiffness, muscle sympathetic nerve activity (MSNA), central sympathetic drive, tissue tone, blood flow (e.g., through an artery, through a renal artery), a blood flow differential signal, blood perfusion, pupil dilation, electrolyte levels in a biofluid, a blood analyte level, nerve traffic, or combinations thereof, at one or more of the monitoring sites to generate one or more physiologic signals, applying a stress test to the subject, and evaluating the physiologic signals obtained from each monitoring site to determine an anatomical map therefrom, a physiologic response to the stress test, or the like.

The method may include using the anatomical map or physiologic response to selectively ablate one or more of the sites.

The method may include determining if a monitoring site includes substantially more sympathetic or parasympathetic neurological features, and/or applying energy in the vicinity of the lumen so as to induce a neurological block in the vicinity thereof. In aspects, the method may include comparing the physiologic signals obtained before the neurological block to those obtained during the neurological block to determine the influence of the neurological block there upon, and optionally determining if the neurological block is favorable in terms of treating an underlying disease state in the body. In aspects, the method may include applying energy in the vicinity of the lumen so as to induce a substantially permanent neurological block in the vicinity of selected monitoring sites.

According to aspects there is provided, use of a method in accordance with the present disclosure for evaluation of the effectiveness of a neuromodulation procedure within a body.

According to aspects, there is provided a method to ablate and/or assess a region of an organ coupled to an arterial tree including identifying a branch of the arterial tree that substantially exclusively provides blood flow to the region, and delivering a bolus of an ablating agent, providing energy to a site along the branch, or the like.

In aspects, the step of identifying may be facilitated by performing one or more contrast angiograms in one or more branches of the arterial tree, correlating an approach with a 3D (three dimensional) tomographic image, a CT image, an MRI image, etc.

In aspects, the method may include monitoring the effect of the composition on the electrophysiological state of the branch (e.g., so as to determine the state of nerve kill, nerve block, the completion of the ablation procedure, the electrophysiological response to a stress test, etc.).

In aspects, the method may include monitoring migration of the composition into the organ and/or a vascular tree coupled thereto.

In aspects, the organ may be a site within the heart, a kidney, and the arterial tree may be coupled to an accessory artery.

In aspects, the method may include performing a stress test on the region of the organ, the stress test including injecting a drug, or a stressing agent such as a vasodilator, a vasoconstrictor, a neuroblocker, a neurostimulant, a diuretic, insulin, glucose, beta-adrenergic receptor antagonist, angiotensin-ll converting enzyme inhibitor, calcium channel blocker, an HMG-CoA reductase inhibitor, digoxin, an anticoagulant, a diuretic, a beta blocker, an ACE inhibitor, a steroid, a combination thereof, or the like into the branch, and/or organ and monitoring a physiological response of the subject to the stress test. Such a test may be advantageous for assessing the function of the region, so as for diagnostic purposes, to select one or more regions to ablate, to compare the performance of regions, to assess the suitability of a subject for a therapeutic procedure, etc.

In aspects, the delivery of the bolus may be directed into a lumen of the branch, an adventitia surrounding the branch, into a wall surrounding the lumen, and/or into an organ coupled thereto.

In aspects, the step of delivery may be performed by a delivery system in accordance with the present disclosure. In aspects, the method may include positioning at least a portion of the delivery system into the arterial tree via a main artery serving the tree. In aspects, one or more portions of the delivery system may be embodied within a catheter and/or guidewire in accordance with the present disclosure.

In aspects, the catheter or guidewire may be equipped with a substance eluting element, configured to deliver the composition, a substance, a medicament, a denervating substance, a combination thereof, or the like into the target organ, into a perivascular site surrounding the wall of the lumen, into the adventitia of the lumen, into a microenvironment of the tumor, into the lumen, into the tissues surrounding the wall of the lumen, in a region within the wall of the lumen, a combination thereof, or the like.

In aspects, the method may include treating and/or ablating one or more nerves coupled to the region, while substantially limiting damage to the tissues surrounding the region or the nerves, substantially limiting damage to the organ coupled to the region, substantially limiting local inflammation, or the like.

In aspects, induced necrosis will typically cause the corresponding cells to exhibit rapid swelling, lose membrane integrity, shut down metabolism, and release their contents into the environment. Cells that undergo rapid necrosis in vitro do not often have sufficient time or energy to activate apoptotic machinery and thus will often not express apoptotic markers. Rather induced apoptosis typically causes the corresponding cells to exhibit cytological and molecular events such as a change in the refractive index of the cell, cytoplasmic shrinkage, nuclear condensation, and cleavage of DNA (deoxyribonucleic acid) into regularly sized fragments.

In aspects, the composition may be selected so as to induce apoptosis in one or more neural tissues (i.e., axon, dendrite, cell body, myelin sheath, synapse, etc.).

According to aspects, there is provided use of one or more systems, methods, and devices each in accordance with the present disclosure for interventionally altering one or more homeostatic or neuroendocrine processes within a body.

Some non-limiting examples of homeostatic processes include production/release of renin, insulin, cholesterol, bile salts, testosterone, progesterone, prion, serotonin, endorphins, dopamine, monoamine neurotransmitters, histamines, noradrenaline, glucose, and the like, adjustment of blood pressure, anti-inflammatory activity, testosterone, estrogen, "uterine hemorrhaging", hunger, bowel movement, nutritional uptake in the bowel, bone density, a rate of bone remodeling, formation of osteoblasts and the like.

In aspects, a system in accordance with the present disclosure may include a substance delivery aspect, configured for elution of a substance into the vicinity of the target.

BRIEF DESCRIPTION OF THE DRAWINGS

Several aspects of the disclosure can be better understood with reference to the following drawings. In the drawings, like reference numerals designate corresponding parts throughout the several views.

FIGS. 5A-5C illustrate the autonomic innervation into the heart and the innervation around the major vessels coupled with a human heart.

FIGS. 11A-11I illustrate aspects of sensing devices in accordance with the present disclosure.

FIG. 16 shows application of a composition, delivery system, and delivery tip each in accordance with the present disclosure to treatment of a carotid body.

FIGS. 17A and 17B show aspects of a delivery system in accordance with the present disclosure for treating tissues along a vessel.

DETAILED DESCRIPTION

Figure 1A:
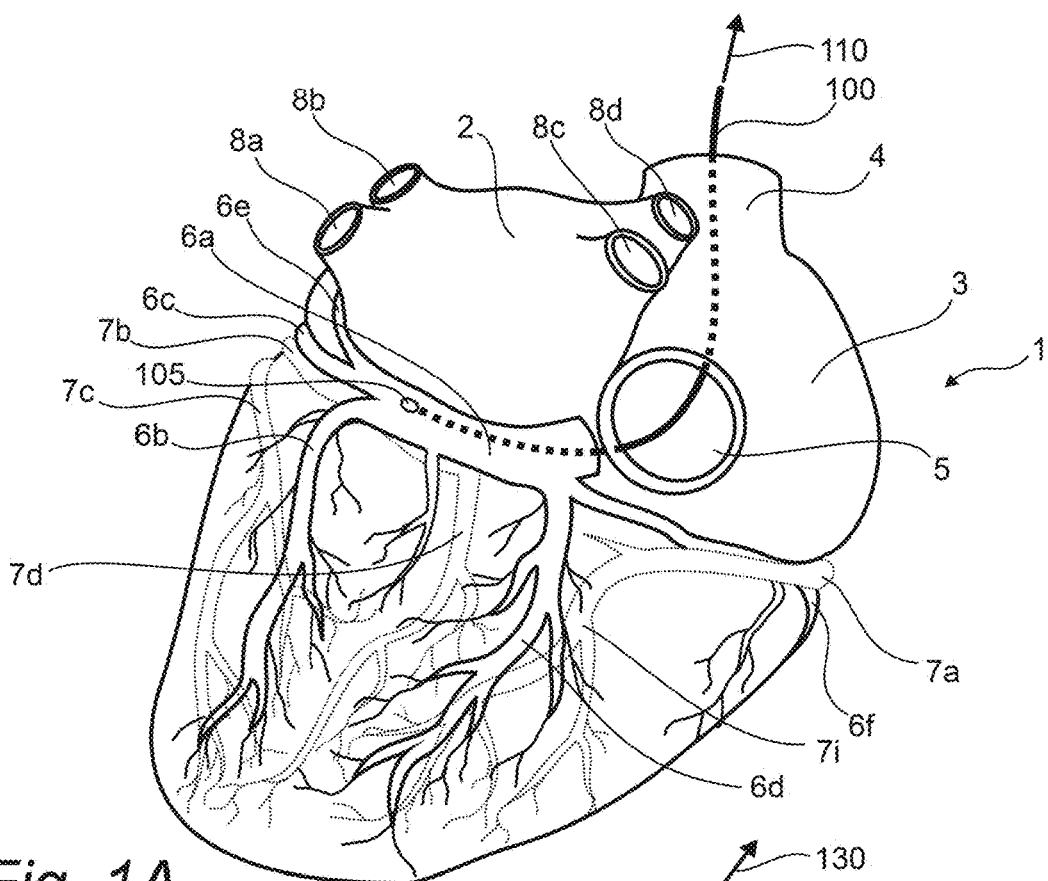
FIGS. 1A and 1B show catheter access routes into various coronary vessels of a human heart.

Particular embodiments of the present disclosure are described hereinbelow with reference to the accompanying drawings; however, the disclosed embodiments are merely examples of the disclosure and may be embodied in various forms. Therefore, specific structural and functional details disclosed herein are not to be interpreted as limiting, but merely as an illustrative basis for the claims and as a representative basis for teaching one skilled in the art to variously employ the present disclosure in virtually any appropriately detailed structure. Like reference numerals may refer to similar or identical elements throughout the description of the figures.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

Methods and techniques for cardiac tissue treatments, as well as cardiac denervation are described throughout this disclosure. In aspects, the anatomic relationships between the neural target sites and to coronary arteries and veins may be considered to access the targets with minimal collateral damage to the adjacent tissues. Autonomic nerve fibers and hence cardiac innervation anatomically co-locates with the coronary arteries and veins after leaving the cardiac ganglia. Such anatomic relationships are analogous to other organs such as the kidney whereby colocation of blood supply and neural traffic make for anatomic, evolutionary efficiency and simplicity (i.e., evolutionary simplification such that there is no need for separate bundles fulfilling different nourishment and regulatory function).

In aspects, specific local sites for targeting therapy are the coronary artery and coronary vein adventitia; the coronary arteries and veins lie on and within the heart muscle, and are very predictable in location and distribution.

In accordance with the present disclosure, cardiac and/or neural therapy, cardiac denervation, or the like can thus be selectively performed through the coronary arteries perfusing a specific cardiac region or the coronary veins receiving blood from a specific region. In aspects, a sensing element, sensing catheter, or the like in accordance with the present disclosure may sense cardiac autonomic neural activity at the inner-lumen of a coronary vessel, a cardiac chamber, etc. Some non-limiting examples of regions that may be targeted with a device and/or method in accordance with the present disclosure include, but are not limited to the atria (individual walls), the ventricles (e.g., ventricular septum, lateral, inferior, posterior, anterior walls), conduction tissue (SA node, AV node, His bundles, R/L bundles), combinations thereof, and the like.

In aspects, autonomic neural sensing may be achieved by antenna deployment (i.e., an array including a plurality of sensing elements and/or electrodes each in accordance with the present disclosure) at the luminal vessel surface. In aspects, a therapy, an ablation procedure, or the like may be performed as guided by luminal autonomic signals.

In aspects, cardiac denervation may also be performed on tissue that is abnormal, for example infarcted, partially infarcted, ischemic myocardium any of which can be detrimental as sources of arrhythmia or abnormal function. In aspects, denervation when performed procedurally in accordance with the present disclosure may be highly controlled and site-selective using a device or method in accordance with the present disclosure. In one non-limiting example, if the locus of an arrhythmia is identified, the myocardium responsible for arrhythmogenesis could be selectively denervated with a device or method in accordance with the present disclosure.

In aspects, to perform a localized, highly selective therapy to such cardiac tissues, a key component of the denervation may involve highly localized sensing in accordance with the present disclosure, a technique that will guide the ablation technology as the procedure is underway, and also determine when the desired ablation has reached its goal. This disclosure thus identifies sensing and ablation within the same device.

In aspects, denervation of tissues in accordance with the present disclosure need not be binary, either none or complete. It can be applied selectively and proportionally (e.g., incomplete, complete, neuro-selective, controlled so as to alter neural traffic or local nerve density by a given percentage, less than 95%, less than 75%, less than 50%, less than 25%, etc.). In one non-limiting example, incomplete denervation may find use, for example, in partially ablating neural drive to a cardiac pacemaker cell group, preserving some degree of natural regulation but decreasing its impact. Another non-limiting example may be found in dysautonomias such as the POTS syndrome (Postural Orthostatic Tachycardia), where a natural reflex is over-reactive. Yet another non-limiting example may be found in coronary vessel spasm, wherein local neural sprouting and aberrant traffic may lead to spasm instead of dilation. In such applications, a controlled, proportional denervation may be advantageous in terms of improved efficacy.

Aspects of the present disclosure may be directed to cardiac ganglion ablation and corresponding methods for sensory-aided catheter-based pre-ablation sensing. In aspects, sensing ganglion tissue prior to ablation would have substantial clinical benefit. A high fidelity sensing element in accordance with the present disclosure may be suitable for measuring ganglion tissue neural activity, generally in the frequency range of 100 Hz-2 kHz, including 200 Hz-1 kHz, and over the voltage range of 1 µV-1 mV, including 1 µV-50 µV. For example, a neural ablation probe (regardless of ablation modality) brought into, within or near a cardiac ganglion of the heart would permit partial or complete ganglion destruction. The sensed autonomic neural information may be utilized to localize the ganglion, diagnose the ganglion neural traffic, quantify the ganglion neural traffic, monitor the traffic during a procedure, after a procedure, etc. Furthermore, the neural sensing may be suitable for mapping changes in spatial neural traffic patterns around a ganglion before, during, and/or after an associated ablation procedure. Such mapping may be advantageous to locate other neural targets, to monitor neural traffic patterns in the vicinity of a ganglion, to/from a ganglion, changes in neural patterns during a local temporary neural block, traffic before, during, or after a plurality of local spatially distributed neural blocks, or the like.

Generally speaking, current methods cannot sense neural or muscular activity thus ablation is carried out in a "blind" manner. The sensing electrode or array of electrodes disclosed herein may be used to sense neurologic or muscular activity consistent with the structure that is intended to be ablated. In aspects, a combination of cardiac electrophysiologic activity, local field potentials, and extracellular action potentials may be monitored by one or more sensing elements and associated microelectronic components in accordance with the present disclosure. Signal analysis may be performed on the recorded signals so as to identify traffic types, to associate traffic signals of a first type with traffic of a second type, etc.

In aspects, the sensing technology can be separated or integrated with the ablation technology. The present disclosure utilizes feedback of a neurologic or myogenic sensing technology in conjunction with the ablation technology to permit direct knowledge of what procedure is being planned in an appropriate patient, whether the procedure is being performed correctly, and when the procedure can be terminated.

In another non-limiting example, a system, device, catheter, method, or a combination thereof each in accordance with the present disclosure may be configured to perform autonomic ablation at one or more sites on the heart, along an atrium of the heart, ventricle, near the ostium of a vessel coupled with the heart, along coronary vessels (e.g., arteries or veins), via procedure based, highly focal cardiac denervation. Such procedures may be suitable for treating various disorders. Some non-limiting examples of such disorders include suppressing aberrant cardiac muscle activity, treating myocardial infarction, cardiac arrhythmias, congestive heart failure, augmenting heart function, altering blood pressure, combinations thereof, and the like.

In aspects, local coronary treatment and diagnostic functions disclosed herein may be used for suppressing coronary artery plaque formation. Multiple histopathologic studies clearly show local inflammation as a major cause of coronary artery plaque formation. This includes vulnerable plaque (responsible for plaque size/growth, myocardial infarction, unstable angina, etc.), stable plaque, and restenosis following interventional procedures. The source of chronic plaque information is poorly understood. Focal inflammation in malignant tumors is enhanced or initiated by active sympathetic autonomic drive. Sympathetic denervation of the heart, by reducing local inflammation may limit coronary artery plaque formation and hence coronary artery disease with a multitude of its consequences. Such an approach may be advantageous for treating subjects with fewer comorbidities, side effects, fewer cardiac events, and longer patient survival than existing therapeutic approaches.

In aspects, local coronary treatment may be used for limiting or eliminating chest pain. Angina pectoris can be debilitating and uncontrollable in a substantial number of heart patients. Refractory angina represents a significant clinical problem that is debilitating and has massive impact for a negative lifestyle and extremely poor quality of life since even minor activities are frequently accompanied by severe pain. In addition, angina at rest often prevents such patients from carrying on any semblance of a normal life. Afferent neural activity conveying pain response travels in part through the coronary arteries. Treatment, and/or ablation of these nerves may result in substantial, marked, or complete elimination of anginal pain in a subject.

In aspects, local coronary treatment may be used for preventing coronary vessel spasm. Spasm of the coronary arteries is a potentially lethal condition whereby neurologically mediated traction of the coronary arteries cause marked reduction or even cessation of blood flow through the coronary artery. Lack of blood flow in a coronary artery can cause severe pain, ischemia, scar formation in muscle, lethal arrhythmias, and death. Affected individuals with recurrent coronary artery spasm are at very high risk for substantial morbidity and mortality. Even in normal individuals coronary artery spasm can play a role in the genesis of heart attack, ischemia, myocardial infarction and associated symptoms including chest pain arrhythmias and death. Autonomic innervation of the coronary vessels contributes to contraction, dilation, and spasm. Such spasm is particularly associated with neuroplastic changes in autonomic innervation (i.e., local neural sprouting associated with damage caused by trauma, local ischemia, plaque formation, receptor density changes, and the like). Local monitoring of associated neural traffic and/or treatment of coronary autonomic nerves may thus have substantial impact on vessel spasm, associated pain, and heart attack thus positively affecting patient life span, quality of life, and the like.

In aspects, local coronary nerve treatment may be used for treating myocardial infarction and unstable angina pectoris. Myocardial infarction and its mechanisms related to coronary artery initiation are poorly understood. It is well known that it is a capricious illness that may occur at any time whereby plaque on the coronary artery interacts with blood flow to cause the clot that obstructs the vessel. It is quite conceivable that coronary artery spasm induces or contributes to the formation of the clot by making an already plaque-narrowed lumen become completely or near-completely obstructed. Moreover, enhanced sympathetic tone locally and systemically is a source of enhanced platelet aggregation, a potent source of increased coronary artery thrombosis. Local identification of aberrant neural traffic and/or treatment of autonomic coronary nerves may thus have substantial impact on myocardial infarction thus positively affecting patient life span, quality of life, and the like.

In aspects, one or more devices, systems, and methods each in accordance with the present disclosure may be used to treat one or more cardiac arrhythmias. Sympathetic beta blockade is a well-known pharmacologic strategy to reduce or eliminate cardiac arrhythmias. These include atrial arrhythmias (e.g., atrial fibrillation, supraventricular ectopy, supraventricular tachycardia) and ventricular arrhythmias (e.g., ventricular ectopy, ventricular tachycardia, ventricular fibrillation). Local, feedback sensing based ablations for treating such arrhythmias may allow for treatment without the need for long term systemic medication, reduction in side effects, patient co-morbidities, and the like.

In aspects, one or more devices, systems, and methods each in accordance with the present disclosure may be used to treat congestive heart failure. A mainstay therapy of congestive heart failure involves beta receptor blockade. Chronic sympathetic stimulation of the ventricular myocardium and heart failure results in a weakening of the heart muscle and very clearly reduces patient survival. Cardiac denervation in accordance with the present disclosure may provide a procedurally-based elimination of sympathetic stimulation which will more exactly, permanently and efficiently eliminate or markedly reduce sympathetic activity in the heart for patients with impending or advanced heart failure.

In aspects, one or more devices, systems, and methods each in accordance with the present disclosure may be used to treat hypertension or alter blood pressure waveforms. Hypertension is a detrimental mismatch between peripheral vascular resistance, cardiac stroke volume, and ejection period. Each of these are controlled in large part by a balance of sympathetic and parasympathetic neural drive. Early evidence also suggests feedback/crosstalk between the renal nerves and cardiac sympathetic nerves. Selective denervation of cardiac structures may thus substantively impact blood pressure. Such an approach may be combined with other therapies to provide a complimentary approach to reducing blood pressure, to cost effectively reduce blood pressure, or the like.

Thus, selectively sensing and ablating the cardiac autonomic nervous system at strategically located sites (such as may be identified with a high fidelity sensory feedback system, device, catheter, sensing tip, sensing element or the like in accordance with the present disclosure), may have a substantial impact toward disease limitation or elimination. A cornerstone of cardiovascular disease treatment utilizes autonomic neural inhibition in the form of sympathetic and parasympathetic neural inhibition. The sympathetic nervous system is inhibited by pharmacologic beta blockade, cornerstones of modern cardiology therapy. Beta blockade is a strategy used to treat chest pain (angina pectoris), congestive heart failure, coronary artery disease, hypertension, and multiple other sympathetic mediated ailments.

In aspects, ablation of nerves within the artery wall may require special design for certain vascular beds. Many vascular beds respond to luminal injury with prolific neointimal thickening, a process causing restenosis after the injury of percutaneous intervention and stenting. The reason for neointimal formation is vascular injury to the media and denotes physiologically by injury to the internal elastic lamina. Implications are significant in that attempted neural ablation in the coronary artery bed, for example, can easily injure the artery and result in unwanted effects of vascular compromise and stenosis. This will occur with heating, RF energy, cryotherapy, microwave, laser, etc., and certain ultrasonic ablation that heat the medial wall.

The present disclosure describes systems, devices, delivery systems, tissue access systems, methods, and compositions in order to treat such coronary tissues with limited risk of vascular injury. Generally speaking, a valid ablation technology should kill only cells in the adventitia. A sensing system in accordance with the present disclosure is configured so as to monitor the neural ablation process, thus allowing for substantially a minimally effective kill, so as to perform the ablative procedure without causing substantial collateral damage to surrounding tissues, the media, endocardium, etc.

In aspects, such a delivery system may include a needle with a fixed stop distally, equal to roughly the medial thickness so as to permit needle deployment whereby the distal needle penetrates into or near the adventitia. In such an arrangement, the proximal needle is without holes, so the ablation fluid deposition pattern is primarily into the adventitial region with minimal fluid delivered into the medial layer of the vessel wall.

In aspects, the patterns and size of holes in the needles may be arranged such that when 3 or more needles are inserted into the media of the vessel wall, delivery of an ablative composition there through may form a substantially complete circumferential linear lesion, and substantially ablate neural activity from crossing this linear lesion. In aspects, a pattern of highly precise and spatially distributed ablations may be formed in the wall of the vessel so as to treat a proportion of it, such as less than 90%, less than 75%, less than 50%, less than 25%, or the like. In aspects, a variable pressure magnitude applied during delivery of boluses of the therapeutic substance may be used to change the size/width of the resulting linear lesion, with more pressure, in general, resulting in a wider lesion.

Alternatively, longitudinal lesions along the length of the vessel may be generated by making exit holes in the needle along the vessel axis rather than perpendicular to it.

This method of making lesions is applicable to making lesions in various arterial supplies to organs within the body.

Some non-limiting examples of ablation applications include but are not limited to, heart based applications as listed herein, pancreas based applications (augmentation of pancreatic blood supply (Celiac/SMA) for treating cancer, to limit or eliminate pain, to favorably impact metastasis and/or tumor progression, etc.), lung based applications (e.g., treatment of pulmonary arteries, denervated to favorably impact vascular resistance (lessen), reduce pulmonary hypertension, etc.), treatment of bronchi (so as to reduce bronchospasm, asthmatic attacks/symptoms, etc.), treatment of the kidneys (to reduce hypertension, change glomerular filtration rates, etc.), treatment of the bladder (to treat neurogenic bladder, LUTs disorders, reduce overactive bladder spasm, pain, urge incontinence symptoms, etc.), treatment of the carotid body (to reduce blood pressure, limit activity, reduce sensitivity to blood pressure changes, etc.), treatment of the adrenal glands (to reduce corticosteroid sensitivity/secretion and the like), treatment of adipose tissue (to alter metabolic function, inflammatory function, etc.), treatment of the spleen (to influence inflammatory function, etc.), treatment of the extremities (to reduce ulcer formation, treat reflex sympathetic dystrophy, etc.), treatment of the stomach (to reduce gastrin/stomach acid secretion, etc.), treatment of the gastrointestinal system, the duodenum, the colon, the small intestine (e.g., so as to affect receptor density distribution, to disrupt gastrointestinal signaling, to treat inflammatory bowel disease, autoimmune bowel disease, autoimmune ulceration, irritable colon, etc.), combinations thereof, and the like.

In aspects, a system, device, surgical tool, interventional tool, catheter, or guidewire in accordance with the present disclosure may be used to access, monitor, and/or to treat one or more neurological pathways, ganglia, and/or sensory receptors within a body: Ampullae of Lorenzini (respond to electric field, salinity, temperature, etc.), baroreceptors, chemoreceptors, hydroreceptors, mechanoreceptors, nociceptors, osmoreceptors (osmolarity sensing), photoreceptors, proprioceptors, thermoreceptors, combinations thereof, and the like. Such receptors may be associated with one or more organs and/or physiologic processes within the body (i.e., a regulatory process, feedback systems, pain receptors, etc.).

In aspects, a sensing device in accordance with the present disclosure may be used to interface with one or more neural structures, perform a diagnostic procedure, or the like. Several descriptions of such devices are included herein, as well as in the applications incorporated by reference below. An example of such a device is an interventional tool (e.g., a microsurgical tool) configured for monitoring electrophysiological activity within the vicinity of a lumen, the microsurgical tool including a one or more distinct sensing and/or actuating elements, e.g., in the form of microfingers, having a substantially elongate structure configured so as to bias a region thereof against a wall of the lumen upon deployment within the lumen, and a sensing tip electrically and mechanically coupled to the microfinger in the vicinity of the region, configured to interface with the wall of the lumen, the sensing tip configured to convey one or more electrophysiological signals associated with the activity. Such devices are further described in PCT application serial no. PCT/US2014/031962, published as WO 2014/160832 and titled "Neurological Traffic and Receptor Evaluation and Modification: Systems and Methods," the disclosure of which is incorporated herein by reference. Other such devices for which sensing function is suitable for performing one or more of the procedures herein include, but are not limited to those devices described in: PCT application serial no. PCT/US2013/023157, published as WO 2013/112844 and titled "Controlled Sympathectomy and Micro-Ablation Systems and Methods"; PCT application serial no. PCT/US2013/042847, published as WO 2013/181137 and titled "Endoscopic Sympathectomy Systems and Methods"; PCT application serial no. PCT/US2013/045605, published as WO 2013/188640 and titled "Devices, Systems, and Methods for Diagnosis and Treatment of Overactive Bladder"; PCT application serial no. PCT/US2013/067726, published as WO 2014/070999 and titled "Systems, Methods, and Devices for Monitoring and Treatment of Tissues Within and/or Through a Lumen Wall"; and PCT application serial no. PCT/US2013/073844, published as WO 2014/089553 and titled "Systems and Methods for Regulating Organ and/or Tumor Growth Rates, Function, and/or Development," the disclosures of which are incorporated herein by reference.

In aspects, one or more systems in accordance with the present disclosure may be coupled with one or more imaging modalities including computer assisted imaging computed tomography (CT), magnetic resonance imaging (MRI), positron emission tomography (PET), magnetoencephalography (MEG), functional MRI, stereotactic surgery, or the like before, during, and/or after a surgical procedure. Such imaging modalities may be used to provide visualization of a target tissue, of advancement of one or more aspects of the system towards the target tissue, confirmation of placement of one or more aspects with respect to the target tissue or surgical site, etc. Use of such imaging modalities may be performed prior to/after surgery, and/or intraoperatively.

In aspects, one or more probes in accordance with the present disclosure may include a fiber optic coupled to a light source and/or a laser (e.g., fiber optic guided radiation to a target tissue), a cryotherapy unit, a heat circulation unit (i.e., a unit for heated wire thermal therapy), an ultrasonic generator, or the like for treatment and/or monitoring of target tissue. For purposes of discussion, the majority of non-limiting examples discussed herein are directed to electrical interfacing with tissues and chemical delivery aspects of such therapies.

A system and/or tool in accordance with the present disclosure may include an elongate member with a proximal end and a distal tip, at least a portion of which may be configured for placement within the lumen of a body, the elongate member including one or more conduits each conduit providing a channel for connecting a more distal aspect of the elongate member to a more proximal aspect thereof. The elongate member may include and/or interface with one or more probes, at least a region of one or more of the probes slide-ably coupled to the elongate member so as to advance from the elongate member in a direction towards an associated lumen wall (e.g., radially, circumferentially, axially, combinations thereof, or the like). At least one probe may include an electrode, a needle, a fluid delivery aspect, combinations thereof, or the like.

In aspects, one or more probes may be arranged so as to pass through one or more of the conduits. In aspects, one or more of the probes and/or conduits may be coupled to a fluid source at a proximal end thereof and configured to provide a fluid there through to a distal tip thereof, to one or more tissue sites in the vicinity of the distal tip, etc.

In aspects, a probe and/or elongate member may include one or more microelectrodes for monitoring local electrophysiological activity, one or more of the microelectrodes may have an area of less than 1 mm$^2$, less than 0.1 mm$^2$, less than 100 µm$^2$, or the like. In aspects, a probe and/or elongate member may include a stimulating and/or ablating electrode for stimulating and/or treating a local tissue site in the vicinity thereof. In aspects, one or more of the stimulating and/or ablating electrodes may have an area of more than 0.25 mm$^2$, more than 1 mm$^2$, more than 2.5 mm$^2$, more than 50 mm$^2$, or the like.

In aspects, one or more of the probes may include a plurality of electrodes (e.g., microelectrodes, stimulating electrodes, and/or ablating electrodes) each in accordance with the present disclosure. Such sensory elements and electrodes may be coupled with one or more delivery elements, the delivery elements configured to deliver one or more substances to a tissue site of interest within a subject.

In aspects, the tissue ablating agent may include an alcohol, ethanol, isopropyl alcohol, benzyl alcohol, phenol, ethanolamine, athanolamine oleate, sodium tetradecyl sulfate, a chemotherapeutic agent, combinations thereof, or the like. In aspects, the tissue ablating agent may perform at least a portion of the function of a vehicle for delivery of the composition to the tissue site.

In aspects, a composition in accordance with the present disclosure may include a toxin, a neurotoxin, paclitaxel, etc. The paclitaxel may interfere with axonal function and neural regrowth in the vicinity of the injection site, thus assisting with the durability of the therapy. In aspects, the composition may incorporate ethyl alcohol (or an alternative ablating agent), in combination with paclitaxel.

In aspects, a composition in accordance with the present disclosure may include one or more of amiodarone, hydralazine, perhexiline, drugs used to fight cancer, cisplatin, docetaxel, paclitaxel, suramin, vincristine, combinations thereof, or the like.

In aspects, a composition in accordance with the present disclosure may include chloroquine, isoniazid (INH), metronidazole (Flagyl), nitrofurantoin, thalidomide, combinations thereof, or the like.

In aspects, a composition in accordance with the present disclosure may include etanercept, infliximab, leflunomide, combinations thereof, or the like.

In aspects, a composition in accordance with the present disclosure may include an analgesic to affect local neural traffic during the delivery process.

In aspects, a composition in accordance with the present disclosure may include one or more of dapsone, an anticonvulsant (phenytoin), an anti-alcohol drug (disulfiram), a combination thereof, or the like.

In aspects, a composition in accordance with the present disclosure may include one or more of didanosine (Videx®), stavudine (Zerit®), zalcitabine (Hivid®), arsenic, colchicine, gold, combinations thereof, or the like.

In aspects, a system in accordance with the present disclosure may include a sensory subsystem in accordance with the present disclosure. In aspects, the sensory subsystem may include one or more microelectrodes mounted to the catheter, near the distal tip thereof (i.e., near to the tissue site during a delivery process). The microelectrodes may be configured to capture electrophysiological signals, neural traffic signals, chemical migration margin information, or the like from the delivery site.

In aspects, a system in accordance with the present disclosure may include a processor, the processor coupled to the sensory subsystem, or to signals generated therefrom, the processor configured to condition and/or display one or more signals associated with the delivery process (e.g., margin of the delivered bolus, migration of the composition over time, etc.), physiologic changes, (e.g., changes in pH, salinity, water content, changes in a systemically measured surrogate marker for the procedure, blood pressure, glucose levels, renin levels, noradrenalin spillover, etc.), electrophysiological changes (e.g., changes in neural traffic, changes in nerve function, changes in one or more nerve signals, changes in the character of nearby action potentials, changes in the phasic character of the action potentials, biphasic to monophasic transitions in such action potentials, etc.).

In aspects, the processor may include a function to determine the proportion of signals measured from the nerves associated with group I, group II, group III, and/or group IV nerve types. In aspects, the processor may be configured to deliver energy and/or the substance to the tissues until a significant drop in group IV traffic is determined by the function from one or more of the sensory signals.

In aspects, a method in accordance with the present disclosure may include determining the proportion of signals measured from the nerves associated with group I, group II, group III, and/or group IV nerve types, the ablating and/or defunctionalizing dependent upon the proportion. In aspects, the step of ablating and/or defunctionalizing may be adapted so as to stop based upon a substantial drop in group IV traffic (e.g., such as by halting delivery of the substance, by delivering a neutralizing substance, by delivering an antidote, by withdrawing the delivery element, etc.). In aspects, the determination of group traffic may include analyzing the shapes and/or propagation characteristics of action potentials as measured amongst a plurality of electrodes in accordance with the present disclosure.

In aspects, the method may include monitoring the extent of effect that a composition or ablation method has on the group I, group II, or group III traffic as measured near to, or coupled to the tissue site. In aspects, the method may include halting delivery of the composition if the traffic changes are not as desired for the given therapy (i.e., if the changes in group I or group II traffic are sufficiently higher than accepted).

In aspects, the method may include ablating and/or defunctionalizing one or more nerves associated with group III or group IV, while substantially preserving one or more nerves associated with group I or group II. Such ablation and/or defunctionalization may be achieved through selection of active substances in a composition in accordance with the present disclosure, and precise delivery and optional monitoring of the effect of the composition to the tissue site in the body.

According to aspects, there is provided a system, a composition, and a method each in accordance with the present disclosure for treating one or more classifications of nerves, muscles, and/or receptors at sites within a body to alter a neuroendocrine, neural, or cardiac function thereof. The method includes selecting a composition in accordance with the present disclosure, the composition being selective to the target nerve, muscle, or receptors, delivering the composition to the sites within the body, and optionally monitoring one or more of nerve traffic, a physiologic surrogate parameter related to the nerve traffic, or the like to determine the extent of treatment. The composition may be delivered, and optionally the effects monitored with a system in accordance with the present disclosure.

According to aspects, there is provided a method for determining the extent of a treatment at a site within a body, the method including administering a composition in accordance with the present disclosure to the site, and monitoring a change in neural traffic in the vicinity of the site, the neural traffic changing with the extent of the treatment, and analyzing the change in neural traffic to determine if the treatment is substantially complete. In aspects, the analyzing may include analyzing one or more action potentials in the neural traffic to determine the type of nerves affected by the treatment, analyzing the action potentials to determine a change in spectral composition thereof as effected by the treatment, analyzing the propagation velocity of one or more action potentials to determine the extent of the change therein as caused by the treatment.

The step of analyzing the action potentials may include analyzing a change in the rise time of the action potential, a change in the pulse width of the action potential, a change in the spectral content of the action potential, a change in the periodicity of similar action potentials (as measured at one or more monitoring sites around the treatment site), a change in the number of similar action potentials per unit of time, a change in the polarity of action potentials (e.g., a change in the number or percentage of positive polarity action potentials, a change in the number or percentage of negative polarity action potentials, a change in the polarity of the aggregate traffic measurement, etc.).

In aspects, a delivery system in accordance with the present disclosure may include a needle, through which a composition may be delivered to a tissue surface, or volume, the needle shaped, and configured to shape the composition (e.g., as a spherical shape, a line, a ring, along a pathway, a fence, bell shapes, elliptical shapes, etc.). In aspects, the needle may include one or more ports through which a composition may be delivered.

According to aspects, there is provided an injection device for delivering a composition in accordance with the present disclosure to one or more tissue sites in a body, the injection device including a needle, the needle including one or more lumens for delivering the composition. The needle may be configured with an occluded tip, or an open tip, may include one or more ports along a wall thereof, may be shaped so as to pattern the composition into a shaped pattern along a tissue surface, or into a three dimensional volume of tissue, shaped so as to adjust an injection rate, size, shape, dose, or distribution of the pattern, etc.

Such a configuration may be used to control a pattern of injection: spherical, linear, ellipsoidal, or other two-dimensional/three-dimensional shape, which may be advantageous for treating a tissue, a region of tissue, a pattern of tissue along a wall, to deliver a medicament to a specific site along a wall of an organ, through a vessel, into a region of tissue beyond a vessel, along a region of muscle, to isolate a region of muscle, to treat a neuromuscular interface, etc.

In aspects, a delivery system/an injection device in accordance with the present disclosure may include one or more sensing components, the sensing components configured to monitor one or more of neural activity, autonomic nervous system activity, afferent nerve traffic, efferent nerve traffic, sympathetic nerve traffic, parasympathetic nerve traffic, electromyographic activity, smooth muscle activity, cardiac muscle electrophysiological activity, intracardiac activity (myopotentials, His-Purkinje pathways), transition between different types of tissue (e.g., such as by impedance measurement, local stiffness measurement, light scatter measurement, etc.), combinations thereof, or the like. In aspects, the sensing component may include one or more electrodes, each electrode configured to sample the activity locally around the tip of an injection device, near to an injection site to determine the margins of the effect of the injection, at a remote site to determine the effect of a delivered composition, etc. One or more of the sensing components may be applied along a needle, a plurality of sensing components may be patterned along and around the needle, etc. In aspects, a plurality of sensing components may be applied along a length of a needle, the sensing components coupled with microelectronics so as to measure impedance, Nernst potentials, biopotentials, etc. there between. Such microelectronics may be configured to determine when one or more sensing components have passed into a lumen wall, is in contact with a fluid (such as blood), has passed from a first tissue type into a second tissue type, etc. Such information may be used to help guide the needle towards a target site, to determine if the needle tip has left the lumen through which it has been guided to the target site, if the needle tip has been guided to a target neural structure, etc.

In aspects, one or more guidewires, surgical systems, methods, or the like each in accordance with the present disclosure may be used to influence, and/or treat cancer progression relating to a perineural invading cancer, such as cancer of the prostate, pancreas, breast, cervix, ovaries, bladder, or combinations thereof. Such treatments may be used to treat pain associated with cancer to slow, to reverse, and/or to prevent perineural invasion of a cancerous tumor into a surrounding neural microenvironment to interrupt, decrease, influence the microenvironment and/or inflammation of tissues in the state of a cancerous tumor, and/or stop neural communication to/from a cancerous tumor and/or the microenvironment surrounding the tumor to a remote site within a body.

In aspects, a system/surgical tool in accordance with the present disclosure may be used to access, monitor, and/or treat one or more neurological pathways, ganglia, and/or sensory receptors within a body: Ampullae of Lorenzini (respond to electric field, salinity, temperature, etc.), baroreceptors, chemoreceptors, hydroreceptors, mechanoreceptors, nociceptors, osmoreceptors (osmolarity sensing), photoreceptors, proprioceptors, thermoreceptors, combinations thereof, and the like. Such receptors may be associated with one or more organs and/or physiologic processes within the body (e.g., a regulatory process, etc.).

In aspects, a surgical tool in accordance with the present disclosure may take the form of a guidewire. The guidewire may be dimensioned and configured for placement within a lumen of a body at and/or beyond a surgical site and/or anatomical site of interest, so as to monitor one or more physiologic signals near the tip thereof. In aspects, the guidewire may provide a pathway for delivery of a second surgical device to the surgical site.

In aspects, a guidewire in accordance with the present disclosure may include one or more energy delivery means for delivering energy to an anatomical site within and/or beyond the wall of a lumen into which the guidewire tip has been placed.

In aspects, a guidewire in accordance with the present disclosure may include one or more sensors (e.g., as located on a micro-tool-tip, a clamp, a hook, a wire element, an electrode in a matrix, etc.) near to the tip thereof. One or more sensors may include a pressure sensor, a tonal sensor, a temperature sensor, an electrode (e.g., to interact with a local tissue site, provide a stimulus thereto, measure a potential therefrom, monitor current to/from the tissues, to measure a bioimpedance, measure an evoked potential, an electromyographic signal [EMG], an electrocardiographic signal [ECG], an extracellular potential electrode, a mechanomyographic signal [MMG], etc.), an acoustic sensor, an oxygen saturation sensor, or the like.

In aspects, a guidewire in accordance with the present disclosure may include one or more analyte sensors, configured to measure one or more analyte concentrations or concentration trends before, during, and/or after a procedure within a body. Such analyte sensors may be provided in an electrochemical form, a fluorescent form, an electro-optical form, a swelling responsive gel, etc.

A sensing guidewire in accordance with the present disclosure may be advantageous for accessing very small anatomical sites within a body, accessing adjunct arteries and/or arteriole pathways along a blood supply to a target organ, accessing a plurality of vessels coupled to an organ, accessing the parenchyma of an organ, for highly localized interaction with a tissue site, for accessing otherwise challenging lumens (e.g., a lumen with substantially small diameter, with substantially tortuous shape, etc.). In aspects, a guidewire in accordance with the present disclosure may provide a means for directing one or more additional tools to a surgical site within a body. In aspects, a guidewire in accordance with the present disclosure may be configured to sense physiologic parameters from and/or to treat tissues within such miniature lumens as part of a procedure (e.g., a surgical procedure, a diagnostic procedure, an ablation procedure, etc.).

In aspects, one or more of the sensors included on the guidewire and electronics associated therewith may be configured to elucidate a range of key physiologic aspects during a procedure. The following description outlines some non-limiting approaches in this respect.

Bioimpedance between one or more electrodes situated on the surgical tool (and optionally a remote electrode), may be used to determine the degree of contact between one or more of the electrodes and an adjacent anatomical site, a tissue state near to one or more of the electrodes, water content of tissues in the vicinity of one or more of the electrodes, and/or potentially estimate the bias force between the electrode and the anatomical site. Additionally, alternatively, or in combination, bioimpedance measurements between one or more electrodes may be useful in determining when adequate contact has been made with the wall of a lumen against which the sensor has been biased as well as how much current may be applied to an anatomical site during a surgical procedure (e.g., ablation, RF ablation, etc.). Additionally, alternatively, or in combination bioimpedance between one or more electrodes may be used to determine the status of tissue positioned there between. In aspects, the bioimpedance spectrum between two or more electrodes arranged along the surgical tool or between coordinating tools may be used to map the local tissue impedance. Such information may be useful to elucidate where such tissue has been completely ablated, where tissue has yet to be ablated, etc.

In aspects, bioimpedance measurements may be correlated with nerve damage data, obtained during prior surgeries, during development of the procedure, and/or obtained during specific testing procedures, such that changes in local bioimpedance data may be used during a surgical procedure to determine the extent of the ablation procedure. Such a configuration may be advantageous in the case that the surgical procedure itself overwhelms the local electrophysiological activity to the extent that neurological monitoring may be hindered for a prolonged period of time after the procedure has been completed.

Mechanomyographic information may be obtained from one or more sensing tips in accordance with the present disclosure during a procedure as determined by slight changes in an associated strain measurement, tip vibration, and/or contact force measurement (e.g., via direct force measurement between the tip and the local anatomy, and/or via changes in the deformation of the surgical tool tip as measured by an associated micro strain gage attached thereupon). Mechanomyographic information may be related to local nervous activity either naturally occurring or in response to a stimulus (e.g., optionally applied by one or more sensory tips, locally, remotely, during and/or via a local RF pulse, etc.). The tip of a surgical device in accordance with the present disclosure may be equipped with a piezoresistive strain gauge, a piezoelectric microtransducer, an interfacial pressure sensing membrane or the like to detect mechanomyographic signals. In aspects, the surgical tool tip may be coated with a micro or nano coating of a piezoresistive and/or piezoelectric material (e.g., a piezoelectric polymer, an electret, a nano-particulate filled elastomer, etc.). In aspects, the mechanomyographic tip may be configured so as to measure one or more aspects of the tissue compliance of the local tissues (e.g., so as to identify calcified material, cancerous tissues, etc.).

In aspects, electrophysiological monitoring at or between one or more electrodes integrated into the surgical tool, may be used to monitor and/or to map nervous response, electromyographic response (EMG), evoked potential, single or multi-unit neural traffic, etc. along the wall of the local anatomy (e.g., vessel wall, the outside of a vessel wall, within an associated tubule, ureter, artery, vein, arteriole, venule, within the parenchyma of an organ, etc.). Such information may be advantageous for selecting tissues on which to perform a surgical procedure (e.g., an ablation procedure, a biopsy, a drug delivery procedure, a selective ablation procedure, etc.), to follow and/or map a nerve along the length of the surgical site (e.g., along the wall of an artery, a vein, a tubule, etc.), to monitor electrophysiological function before, during, and/or after a surgical procedure, or the like. In aspects, local electric field potentials (EFP) may be monitored before, during and/or after a surgical procedure as a means for monitoring local nervous activity. EFP signals may thus be used as feedback for monitoring the extent of a denervation procedure.

In aspects, one or more electrodes may be configured to monitor local electrical fields during an ablation procedure in order to better determine the current flow path through the adjacent anatomy, connected to a warning system to indicate to an operator when the ablation field is insufficient for achieving the intended goal, etc. Such a configuration may be advantageous for avoiding unnecessary damage to the tissues during a misfired ablation session, etc.

In aspects, the tone (e.g., mechanical properties, wall stiffness, elastic spectral response, mechanical impedance, physiologic properties, etc.) of the adjacent tissues may be determined by combining strain and/or force measurement of sensors integrated into the surgical tool while applying movement (optionally cyclical or oscillatory movement) to one or more sensor tips while biased against the adjacent tissues. Such a surgical tool may include means for applying a local excitation (e.g., such as by a local piezoelectric transducer, a capacitive transducer, an electrochemical transducer, etc.) to one or more of the sensors or globally (e.g., such as by transverse oscillations, axial oscillations, general oscillations of the surgical tool tip, the clamp, the hook, the loop, etc.).

In aspects, one or more surgical tool tips may be interfaced with the associated tissues at an acute angle. By acute angle is meant that the surgical tool tip approaches the associated tissue surface at an angle other than perpendicular thereto. A local excitation may be applied with relatively small amplitude so as not to generate substantial relative movement between the tissue and the tip during the excitation process (e.g., such that the transverse contact forces remain below the slip conditions between the tip and the tissue, such that they move together during excitation). By relatively small is meant an excitation that is sufficiently small in amplitude such that the sensing tip may not appreciably slide along the tissue surface. In aspects, a vibratory exciter included in the sensory tip, or in a structure attached thereto, may be configured to generate the excitation.

Such a tone monitor may be combined with interfacial contact sensing and/or sensor tip strain measurement in order to generate a wealth of local tissue information during a surgical procedure. In aspects, the local tissues may stiffen during an ablation procedure. By monitoring local tissue tone, a stiffness level may be used to characterize when a suitable degree of ablation has been applied so as to irreversibly damage the tissues. Monitoring of a local tissue tone at a monitoring site significantly removed from the surgical site such that the surgical procedure does not directly affect tissues in the vicinity of the monitoring site (e.g., does not directly cut, heat, ablate, abrade, the tissues, etc.) may also be advantageous for determining an effect of the surgical procedure on one or more physiologic parameters of a tissue (e.g., a vessel wall stiffness, change in nerve activity, change in local blood perfusion, etc.) adjacent to the monitoring site.

Such tone measurement may be useful in determining the local stiffness of tissues (and/or overall wall stiffness of an adjacent vessel, organ, etc.) in contact with an array of surgical tool tips (e.g., so as to determine the type of tissue adjacent to one or more tips, to locate transitions between one tissue type and another, to locate regions of excessive wall thickness, to locate a cancerous tumor, etc.). Tone measurement may further be used to characterize the type of tissue with which the tip is interfacing (e.g., muscle, nervous tissue, plaque, cancerous tissue, etc.). Such information, possibly in combination with bioimpedance data, may be used to determine how much RF energy to apply locally during an RF ablation procedure.

In aspects, relating to a method for RF ablating tissue, the local tissue tone may be measured before, during, between individual RF pulses, and/or after a train of RF pulses. As the local tissue tone changes during application of the RF pulses, the tonal changes may be used to determine the extent of the therapy. As the RF ablation process is applied to the adjacent tissues (via one or more sensing tips, an ablation electrode, etc.), the tonal measurements (as determined by one or more sensing tips, via the same tip through which the RF signal may be applied, etc.) may be monitored as the tonal measurements may not be significantly affected by the local RF currents.

Electrophysiological stimulation and/or sensing from one or more electrodes arranged along the surgical tool may be used to monitor and/or stimulate nervous and/or physiologic function within a local anatomical structure (e.g., a vessel wall, along a nerve, an organ wall, a duct, etc.). Such information may be used to hunt for target tissues (e.g., nerves), select tissues for a surgical procedure, to determine the degree of progression of a surgical procedure (e.g., a degree of ablation or neuromodulation during surgery, etc.). In aspects, directional stimulation and sensing may be used to selectively treat only nerves that are configured to send signals in the preferred direction (e.g., to selectively target primarily efferent nerve bundles, afferent nerve bundles, etc.).

In aspects, one or more of the electrodes may be configured to apply/receive an RF or microwave current to/from the surrounding tissue. The current may be provided locally between two of more electrodes, or alternatively between one or more electrodes and a macroelectrode placed elsewhere on the body (e.g., on a large skin patch over the surgical site, an electrode placed on another organ, as selected from multiple patches placed over the body, in an associated catheter electrode, etc.). In a non-limiting example where current is restricted to being applied between electrodes, the path for current flow may be well controlled, yet may be highly localized. Alternatively, in an example where current is passed between one or more electrodes and one or more remotely situated macroelectrodes, the current flow may be more challenging to control, but may be used to access tissues more remote from the surgical tool (e.g., farther into the adjacent tissues, etc.).

In aspects, network impedance measurements between one or more electrodes and one or more macroelectrodes (e.g., as attached to the body of the patient), may be monitored prior to and/or during application of an RF ablation current. Each surgical tool electrode and/or macroelectrode may include an impedance control circuit that may be adjustable such that the overall current flow through the network formed from all the elements is controlled there through. Such a configuration may be advantageous to better control the local ablation process, thus targeting the local tissues with more accuracy and confidence than less controlled approaches.

In aspects, a plurality of electrodes may be engaged with the flow of current during an ablation process. In such a non-limiting example, the local impedance of each pathway (i.e., through the surgical tool and each associated electrode) may be monitored and/or controlled so as to better optimize the current delivered thereto. Additionally, alternatively, or in combination, the local current flow through each electrode may be monitored so as to determine the path of the current flow, to ensure no leakage currents are detected, etc. Such information may be used to better control the delivery of ablation and/or stimulation currents to the local anatomy during an ablation/stimulation procedure.

Optionally, before, during and/or after the ablation or stimulation current is applied to the surrounding tissues, one or more sensors arranged on the surgical tool may monitor a physiologic parameter (e.g., water concentration, tone, blood oxygen saturation of local tissues, evoked potential, stimulation/sensing of nervous activity, EMG, temperature, analyte level, etc.) to determine the extent of completion of the intended surgical procedure.

In aspects, the tip of the surgical tool may be equipped with an optical microsensor (e.g., a micropackage including a light source and/or a complementary metal-oxide semiconductor (CMOS) photosensor). During a surgical procedure, the optical microsensor may be positioned against or near to the local tissues for analysis before, during and/or after an ablation procedure.

In aspects, an optically configured sensor (or group of tips) may be configured to locally assess blood perfusion, renin concentration, tissue colorimetric properties, and/or blood oxygenation in the tissues adjacent thereto. The system may be configured to automatically adjust and/or halt the surgical procedure based upon changes (or lack thereof) in this signal. Alternatively, additionally, or in combination, the system may alert a user (e.g., a surgeon, an attendant, etc.) to a change in this signal before, during, and/or after a surgical procedure. Such a configuration may be useful for assessing local tissue health before, during, and/or after a surgical procedure.

In aspects, one or more optically configured sensors may be configured to monitor for changes in the colorimetric properties of tissues adjacent thereto, such as during an ablation procedure. Such colorimetric property changes may be indicative of a change in tissue state caused by the procedure (e.g., local tissue damage, denervation, etc.).

In aspects, one or more optical sensors may be configured so as to be biased towards the tissues of the vessel in the vicinity of the surgical site or distally therefrom. The optical sensors may include one or more light sources (e.g., light emitting diodes, fiber optic tips, etc.) configured to deliver narrow, multiband, and/or wideband light to the adjacent tissues. The optical sensors may include one or more photodetectors (e.g., a photodetector, a phototransistor, OCT fiber bundle, a fiber optic tip, etc.) to receive and/or analyze the light reflected from the adjacent tissues. The received light may be related to that emitted by one or more of the light sources, or may be received from an ambient light source, located to the exterior of the vessel, or the exterior of the subject's body.

In aspects, one or more of the sources may be configured to emit light at predetermined wavelengths such that different absorption characteristics of the adjacent tissues, dependent on the wavelengths, may be observed during the surgical procedure. The photodetectors may be configured to receive at least a portion of this light, so as to assess the absorption characteristics with the system (e.g., via a pre-amplification system in accordance with the present disclosure, in an attached electronics unit, etc.). The photodetected signals may be used to determine an oximetry value or a signal related thereto.

In aspects, the optical sensors may be biased towards a site on the lumen wall before, during, and/or after the surgical procedure. Alternatively or in combination, the optical sensors may be held in a predetermined orientation with respect to the lumen wall (such as via being attached to a collar of known size, attached to a structure of known width, as part of a structure that is expanded to a known radius, onto the inner surface of a hook element, etc.). The bias between the sensors and the wall may be controlled by sensors and actuators both in accordance with the present disclosure. Changes in the optical signals detected by the photodetectors (due to changing bias force) before, during and/or after a surgical procedure may be related to changes in the bias force with which the sensors are held against the vessel wall. Such a configuration may be advantageous for determining a change in sympathetic tone and/or vasodilation before, during and/or after a surgical procedure.

In aspects, one or more of the optical sensors may be coupled with one or more strain and/or interfacial force measurement methods, to give a more precise reading of the bias force between the sensing tip(s) and the adjacent tissues.

In aspects, the optical sources may be selected such that the penetration of the light into the adjacent tissues may be controlled. In aspects, a blue wavelength and a red wavelength may be emitted into the tissues. The blue wavelength may provide information relating to the deformation and absorption near the to the surface of the tissues, while the red wavelength may penetrate more deeply into the adjacent tissues, providing a signal that changes in response to deformation of tissues farther from the contact site(s) between the sensor(s) and the tissue. The photodetectors or equivalent optical detection pathway may include filters, polarized windows, or the like to separately assess the different spectra during an analysis. Comparison between the photodetected signals in the blue spectrum with those obtained from the red spectrum may be used to determine tone and/or elastic modulus of the tissues of the vessel in the vicinity of the optical sensors. Such a configuration may be advantageous for assessing sympathetic tone and/or vasodilation, vessel wall stiffness, and/or local tissue stiffness before, during and/or after a surgical procedure. Changes in such properties may be indicative of the degree of completion of the surgical procedure.

In aspects, an externally placed (e.g., onto the body of the subject) energy source (e.g., infrared, near infrared, visible, microwave, radiation, etc.) may be directed into the body towards the surgical site. The energy source may optionally be modulated to provide a more easily detected signal within the subject. One or more optical sensors arranged upon the surgical tool may be configured to sense light emitted from the energy source. The mapping of received light may be used to locate anatomical features such as nerves near to one or more of the optical sensors.

One or more externally placed light sources may be used to help locate the anatomical sites of interest during the procedure. An external light source may include a narrow band light source, a broad band light source, light sources spaced apart from each other, and/or combinations thereof. The light sources may be modulated so as to be more easily detectable by sensors located in or near to the anatomy of interest. In one non-limiting example, a plurality of light sources may be aimed at the surgical site from distinct vantage points within the body (i.e., as accessed via an endoscopic procedure, etc.) or externally to the body (i.e., as positioned at locations on the body).

In aspects, an endoscopic camera may be placed near to the anatomy during a procedure to observe both the anatomy, as well as placement of the surgical tools in the vicinity of the anatomy. In one non-limiting example, the endoscopic camera and/or light source may provide a suitable macroelectrode for RF ablation processes performed during the surgical procedure.

In aspects, one or more optical sensors may be equipped with a corresponding micro-light source (e.g., an organic light-emitting diode (oLED), a light-emitting diode (LED), etc.). The micro-light source may be used to direct light into the adjacent tissues. One or more optical sensors may be configured to detect light emitted from the micro-light source as back scattered by the adjacent tissues. Such information may be used to detect anatomical features (e.g., nerves, tumors, etc.) in the adjacent tissues.

Such optical configurations may be advantageous for mapping the local tissues before, during and/or after a surgical procedure. They may also be advantageous for implementation into a nerve detection system (e.g., as input to a nerve hunting algorithm, etc.).

In aspects, the surgical tool may include one or more microcircuits interconnected with one or more of the sensors. Such a microcircuit may include signal processing circuitry, a local control circuit, multiplexors, communication hardware, power management, combinations thereof, or the like. In order to substantially reduce the number of signal wires that must be routed to the surgical site during the procedure, a networked array of electrodes arranged within the surgical tool may be multiplexed together with a locally placed control circuit (e.g., an application specific integrated circuit, distributed/interconnected circuit elements, a collection of flexible semiconducting circuit elements, etc.). The control circuit may communicate such signals with an extracorporeal system (e.g., a computer, a control system, an RF ablation controller, a data acquisition system, etc.). The control circuit may communicate with the extracorporeal system via analog and/or digital methods. In one non-limiting example, the communication may be of primarily digital means such that the control circuit may exchange data pertaining to any sensing tip in the array, as well as switch data, control data, RF pulse routing, etc.

In aspects, the networked array of electrodes may be interconnected with distributed electronic elements and flexible electrical interconnects (e.g., as applied to a clamp surface, a hook, a loop, as provided by structural wires, microfingers, wire mesh elements, etc.).

A surgical tool (e.g., a guidewire, a catheter, etc.) in accordance with the present disclosure may include one or more microfingers arranged such that each microfinger may move or interact with local anatomy substantially independently from other microfingers in the tool. Thus if an array of microfingers is placed against a rough or otherwise uncontrolled surface, each microfinger may be able to contact, and substantially maintain contact with the surface during use, even if the microfinger array is dragged along the surface during a procedure. Such independently adjustable microfingers may be advantageous so as to maintain a known interfacial pressure, especially while monitoring, stimulating and/or ablating the tissue with the microfingers.

By microfinger is meant a, potentially curved, finger like member (i.e., optionally with multi-axial curvature). Such microfingers may generally have a characteristic width (although may be of any cross sectional makeup). The microfingers may generally have characteristic widths on the order of approximately 1 mm, 0.5 mm, 0.1 mm, 0.05 mm, 0.01 mm, or the like. In aspects, one or more microfingers may include a nitinol structure (e.g., a wire, a ribbon, etc.) with characteristic width of approximately 50 μm.

In aspects, one or more of the microfingers may be selectively coated with an isolation layer (e.g., an oxide layer, a dielectric coating, a polymer layer, a lubricious layer, etc.). Such isolation may be selectively applied to regions of the microfingers (i.e., so as to create isolated regions and sensitive regions thereof).

The microfingers may be configured so as to bias against the adjacent tissues during a procedure and may be used to sweep the local anatomy, both sensing and ablating during a surgical procedure. The microfinger dimensions and structure may be designed so as to provide substantially uniform and predictable bias forces on the adjacent tissues over a wide range of movements and dimensional variation.

In aspects, one or more microfingers may include a spring-like wire element (e.g., nitinol, spring steel, etc.) or may include composite structures including a spring-like element to provide a bias force so as to push the tip of the microfinger towards the wall of a vessel, an organ, and/or a tissue site of interest.

In aspects, a microfinger may include a nitinol structure, optionally configured for passage of current flow, to and from the surrounding tissues. The nitinol structure may be configured such that, when an RF pulse is applied there through towards the surrounding tissues, the nitinol structure may retreat from the tissues after a predetermined amount of energy has passed there through. Thus the nitinol structure may provide an inherently controlled method for applying a bolus of RF energy to the surrounding tissues. Such a configuration may be adapted for use simultaneously, additionally, alternatively and/or in combination with the other aspects described in this disclosure.

In aspects, one or more of the microfingers may be formed slightly off axis, such that relative axial movement of an overlying sheath may be used to retract the microfingers into the sheath or deploy the microfingers outwards so as to interface with the anatomical site.

Such a configuration may be advantageous for simultaneously mapping and selectively ablating an anatomical site during a surgical procedure.

In aspects, one or more microfingers may be provided with a highly miniaturized and flexible structure so as to more easily access hidden and/or difficult to access anatomical sites within the body.

In aspects, one or more of the microfingers may include a sensor in accordance with the present disclosure for capturing information from an adjacent anatomical site.

In aspects, a system in accordance with the present disclosure may include a coolant delivery system (e.g., a saline delivery system) in order to cool the microfingers and/or surrounding tissues during and/or after an ablation procedure. Such coolant delivery may be advantageous for minimizing char and excessive damage associated with an ablation procedure. In aspects, such a coolant may be provided to maintain one or more of the microfingers in a first state (i.e., a delivery state). When the coolant flow is stopped, the associated microfingers may transition to a second state (i.e., a deployed state). Such a configuration may be advantageous for delivering a guidewire tip in accordance with the present disclosure deep into a target lumen before deploying one or more zones of the guidewire so as to interface with the walls of the lumen as part of a procedure.

In aspects, one or more of the microfingers may include an exposed electrode area arranged so as to primarily interface with the walls of the adjacent anatomy upon deployment. Such a configuration may be advantageous for minimizing current flow into the adjacent tissues and to better control RF current flow in the vicinity of the electrodes, etc.

The microfingers may include one or more active material elements. Control signals delivered to the active material element may help to bias the microfingers towards the intended surgical site, actively control the contact forces between finger tips and the surgical sites, etc. Some non-limiting examples of active materials that may be suitable for application to one or more microfingers include shape memory materials (e.g., shape memory alloys, polymers, combination thereof), electroactive polymers (e.g., conjugated polymers, dielectric elastomers, piezoelectric polymers, electrets, liquid crystals, graft elastomers, etc.), piezoceramics (e.g., amorphous piezoceramics, single crystals, composites, etc.). In addition, the active material may be used as a vibratory exciter and/or mechanical probe, for use in monitoring the tone of the adjacent tissues (see above), alternatively, in addition or in combination, to cause vibratory/ultrasonic ablation and/or local heating to the tissues. In aspects, such active material elements may be configured for simplified deployment of one or more aspects of an associated guidewire towards the walls of a lumen into which it is inserted during a procedure.

In aspects, one or more electrodes may include a conjugated polymer to interface with the adjacent tissues. Some non-limiting examples of suitable conjugated polymers include polyaniline, polypyrrole, polyacetylene, poly(3,4-ethylenedioxythiophene), and the like.

In aspects, one or more of the microfingers may include an electrical shield such that the associated microfinger tips are effectively shielded from other currents flowing through an associated surgical tool (such as a catheter), the body, etc. during a procedure.

In aspects, a surgical tool may include or interface with a bi-directional switching network, microcircuit amplifier array, etc. in order to amplify sensed signals as close as possible to the anatomical interface, as well as to switch the function of a microfinger tip between sensory, stimulatory, and/or ablation functions, etc.

A bidirectional switching network may be used to enable multi-functional stimulation/sense capabilities in one or more microfingers, tool tips, etc. The switching network may be included in a local amplifier array, included in a flexible circuit on one or more microfingers, attached along the surgical tool, as part of the electrical routing along a finger, etc. or alternatively as an extracorporeal element included in a surgical system in accordance with the present disclosure.

A micro amplifier array may be used to preamplify the signals obtained from one or more sensory aspects of the microfingers, so as to improve the noise signature, etc. during use.

In aspects, one or more of the microfingers may be provided such that they are sufficiently flexible so as to buckle, or change orientation during back travel (e.g., configured and dimensioned so as to prolapse), so as to prevent puncture of the local anatomy. A configuration as outlined in this example may be advantageous for providing contact with the local anatomy without significant risk of damaging the adjacent anatomy (e.g., puncturing a vessel wall, etc.) which may be a concern with stiffer, more traditional structures.

In aspects, one or more of the microfingers may be sufficiently hyper elastic (e.g., formed from a memory alloy material, a superelastic material, etc.) so as to effectively deploy from a very small deployment tube and expand outward to larger tissue areas over which to monitor. Such a configuration may be advantageous in so far as a small number of unit sizes may be suitable for treating a wide range of anatomical structures. In addition, the designed curvature and form of a microfinger may be substantially chosen so as to further enable a wide deployable range of movement.

In aspects, a surgical tool including a plurality of microfingers in accordance with the present disclosure may be employed so as to determine physiologic response more remotely from an intended surgical site than may be available within a single array. Any of the above concepts may be employed along the same lines by extending interactions between microfingers within an array, to inter-array interactions.

A system in accordance with the present disclosure may be used to monitor physiologic activity associated with a surgical site prior to, during and/or after a surgical procedure is applied thereto. In aspects, a system in accordance with the present disclosure may be configured to provide a surgical procedure, optionally in conjunction with the monitoring. Some suitable examples of surgical procedures include RF ablation, Argon plasma coagulation, laser ablation, water jet ablation, ultrasonic ablation, cryoablation, microwave ablation, abrasion, biopsy, delivery of a substance (e.g., a chemical, a drug substance, an acid, a base, a chemotherapy drug, etc.), etc. The local physiologic activity (e.g., nervous activity, blood perfusion, tonal changes, muscular sympathetic nerve activity, local field potentials, etc.) may be monitored with one more sensors and/or associated stimulators. Additionally, alternatively, or in combination, a technique for assessing the properties of an associated surgical site may be employed. Such techniques may include assessing values and/or trends in bioimpedance, blood pressure, tissue oxygenation, tissue carbon dioxide levels, local temperatures and changes thereof, etc.

In aspects, the system may be configured to deliver a substance such as a therapeutic agent (e.g., a neuroblocking agent, ethyl alcohol, botulinum toxin, etc.) to the anatomical site of interest or a treatment site.

In aspects, a system in accordance with the present disclosure may include a substrate onto which one or more sensors may be coupled. Such a substrate may be formed from a clamp face, a hook interface, a mesh, an interwoven ribbon array, a cloth, rolled film, etc. The substrate may include stretchable and/or flexible electronic materials.

In aspects, a procedure in accordance with the present disclosure may be used to treat one or more sites along an organ wall (e.g., a bladder, a urethra, a ureter, a prostate, a testicle, a heart, a liver, a stomach, a bowel, a biliary tract, a pancreas, a kidney, an artery, a vein, a vessel, a lymph node, a bone, a periosteal space, a lung, a bronchial tract, a gland, a ganglion, a region of the limbic brain, an ovary, a uterus, cardiac muscle, cardiac ganglia, etc.). In aspects, the composition may include a contrast agent in accordance with the present disclosure, such that an operator may visualize where the composition has been delivered along the organ wall, where it has migrated to, etc.

In aspects, a sensory component in accordance with the present disclosure may be used to determine the ischemic border zones/the isthmus for ischemic myocardium using one or more sensors on the tip of a delivery system or injection device in accordance with the present disclosure. Once the border zone is detected, the delivery system or injection device may deliver one or more boluses of a composition in accordance with the present disclosure to treat the border. Optionally, the sensory component may be configured to monitor the effect of the composition on the electrophysiological activity along the border, so as to determine when the treatment has been completed.

In aspects, the composition may be configured to perform a cryoablative procedure on tissues in the vicinity thereof (i.e., by delivery of a super-cooled composition, a composition for providing a localized endothermic reaction, etc.). In aspects, such cryoablative compositions may include one or more metal complexes, a metal complex in combination with a salt solution, etc. In aspects, the composition may be configured as a two part solution, the two parts mixed before, during, and/or after delivery to the tissue site.

In aspects, a composition, a delivery system, or a method each in accordance with the present disclosure may be applied to treatment of several tissues or disease states within a body, such as the gastrointestinal system, the cardiac system, the neuroendocrine system, the renal system, the ANS (autonomic nervous system), the CNS (central nervous system), a peripheral nerve, a neuromuscular junction, a cancerous tumor, a cosmetic procedure (i.e., combined botox and bulking applications, etc.), and the like.

Some non-limiting examples of treatments for the gastrointestinal system include, treatment of electrical storm in a bowel, treatment of an autoimmune disorder, treatment of LUTS, overactive bladder (e.g., treatment of receptors in the bladder muscle, in the neural pathway between the bladder and local ganglia, along a muscle wall of a urethra, etc.), incontinence (e.g., urinary or fecal incontinence, adjustment of sphincter tone, etc.), treatment of ulcerations (e.g., via injection of growth factors, topical application thereof, etc.), or the like.

Some non-limiting examples of cardiac applications are for the treatment of atrial arrhythmias (AFib, SVT, APCs, AVNRT, WPW/Accessory tract, AVN Ablation), treatment of aFib in specific patterns (e.g., 'dots' or spherical patterns, linear patterns, two-dimensional or three-dimensional shapes, combined with contrast agent to visualize the injected pattern under fluoroscopy, x-ray, MR, or ultrasound-based imaging technologies, etc.). In MR applications, the composition may include one or more ferromagnetic components (e.g., an iron or iron oxide complex, a gadolinium complex, etc.), configured to assist with visualization of the placement of composition into a tissue site, etc.

Such applications may be further improved with combination of a sensing component in accordance with the present disclosure to assess/avoid regions of the esophagus (for example, induce a swallow and sense esophageal EMG within the heart wall prior to injection, to ensure adequate margins, etc.).

Some additional cardiac applications include treatment of ventricular arrhythmias (VT, VF, PVCs), such as may be accomplished by sensing regions of slowed conduction and ablate selectively with a composition in accordance with the present disclosure, follow this region with further sensing to ablate the entire affected zone. Such treatments may be enhanced with combination of a composition in accordance with the present disclosure and a sensory component in accordance with the present disclosure (such as may be unipolar, bipolar, multipolar, etc. configured to determine epicardial activity during treatment, to determine the extent of the composition treatment, to assist with determining the next site to treat, etc.).

Some additional cardiac applications include treatment of one or more autonomic plexi in the vicinity of the heart or coupled thereto. Such structures related to aFib and other arrhythmogenic foci that are autonomic dependent include ganglia, vagal (hypervagotonia, etc.) and dysautonomias, POTS, etc. Such structures may be targeted along/near a vein of Marshall, along the epicardium, along the pericardium, etc.

Some non-limiting applications related to neuroendocrine remodulation include renal nerve treatments, renal artery treatment, treatment of renal accessory vessels, adrenal arteries, carotid sinus, carotid body, autonomic ganglia (e.g., celiac, carotid, etc.), and the like.

Some additional non-limiting applications include treatment of one or more neuroendocrine aspects of congestive heart failure, hypertension, metabolic syndrome (MSx), hypogonadism, inflammatory diseases, infiltrative diseases, infection, chronic wounds, Sjogren's syndrome, Gaucher disease, Parkinson's disease, epilepsy, depression, tumors, stroke, diabetes, cancer, pancreatitis, islet cell tumors, nephrotic syndrome, kidney stones, lower urinary tract disorders, urinary incontinence, urinary tract infection, neurogenic bladder disorders, male or female fertility, impotence, premature ejaculation, prostate cancer, ovary cancer, uterine cancer, gastrointestinal ulcers, acid reflux disorders, celiac disease, irritable bowel syndrome, gastrointestinal cancers, tuberculosis, cystic fibrosis, pulmonary hypertension, chronic obstructive pulmonary disease, lung cancer, coronary artery disease, arrhythmias, and chronic renal failure. Treatment of abnormalities of hormonal secretion such as increased catecholamine, renine and angiotensin II levels, increased blood pressure due to peripheral vascular constriction and/or water and sodium retention, renal failure due to impaired glomerular filtration and nephron loss, cardiac dysfunction and heart failure due to left ventricular hypertrophy and myocyte loss, stroke, and diabetes. Additional treatments may include augmentation of function or a disease state associated with a vessel, an artery, a vein, a tubule, a renal artery, an arteriole, a venule, a duct, a chamber, a pocket, a tubule, a bowel, a urethra, an organ, a combination thereof, or the like.

In aspects, applications include treatment or alteration of function of one or more organs, some non-limiting examples of which are a kidney, a prostate, a testicle, a pancreas, a liver, a lung, a bowel wall, a stomach wall, a gland, a neural body, a carotid body, a gall bladder, a small intestine, a large intestine, a spleen, a pancreas, a bladder, an adrenal gland, a uterus, lymph node, a ganglion, combinations thereof, and the like. Treatment of one or more symptoms, neurological, and/or neuroendocrine contributions to lower urinary tract symptoms (LUTS) secondary to benign prostatic hyperplasia (BPH), chronic prostatitis (CP), hypogonadism (HG), nocturia, prostate cancer (PrCa), and erectile dysfunction (ED), micturition, incontinence, frequency, pain, bladder capacity, and/or configured to modulate neural activity in at least a portion of the bladder wall, or the like.

Such compositions, delivery systems, and/or methods in accordance with the present disclosure may be used for treatment so as to affect the growth rate, hormone secretion rates, or development of an organ (e.g., a prostate, a testicle, etc.), or a tumor (e.g., a prostate cancer tumor, a perineural invading cancerous tumor, lymphatic invading tumors, etc.), lymphatic ducts, lymphatic nodes, or the like, to alter functions including a sensation (e.g., a hunger sensation, an urge to urinate, pain, etc.), a tremor, altering release/secretion of a chemical substance (e.g., acid, hormones, toxins, bile, enzymes, surfactants, sebum, renin, etc. from a secretory cell), altering smooth muscle tone, or the like. Such a composition, system, or method may be used to treat a disease of the gall bladder, renal system, metabolic functions, gastrointestinal function, to augment hunger sensation, reduce tone, combinations thereof, and the like.

In aspects, some non-limiting examples of medical conditions that can be treated according to the present disclosure include genetic, skeletal, immunological, vascular or hematological, muscular or connective tissue, neurological, ocular, auditory or vestibular, dermatological, endocrinological, olfactory, cardiovascular, genitourinary, psychological, gastrointestinal, respiratory/pulmonary, neoplastic, or inflammatory medical conditions. Further, the medical condition can be the result of any etiology including vascular, ischemic, thrombotic, embolic, infectious (including bacterial, viral, parasitic, fungal, abscessal), neoplastic, drug-induced, metabolic, immunological, collagenic, traumatic, surgical, idiopathic, endocrinological, allergic, degenerative, congenital, or abnormal malformational causes.

The present systems and methods also encompass enhancing the therapeutic effects of other therapies, such as methods and systems working in conjunction with a pharmaceutical agent or other therapies to augment, enhance, improve, or facilitate other therapies (adjunctive therapies) as well as reducing/minimizing and counteracting side effects, complications and adverse reactions for any therapies involved in treating the above-mentioned medical conditions.

In aspects, liver function which may be augmented by a treatment and/or monitored in accordance with the present disclosure include glucose storage/release, metabolic sensing (and related signal traffic to the brain related thereto), glucoregulatory function, afferent vagal activity reaching the brain, chemoreceptor function (or related signal traffic associated therewith), lipid sensing/synthesis, regulation of hepatic insulin sensitizing substance, afferent traffic augmentation associated with glucosensors (i.e., primarily in the region of the portal vein, etc.), protein sensing, GLP-1, leptin, CCK, FFA, PPAR alpha and gamma, glycogenolysis, gluconeogenesis, VLDL secretion, ketogenesis, hypoglucemia sensing, or the like.

In aspects, one or more compositions, delivery systems, and/or methods in accordance with the present disclosure may be used to treat cancer of the prostate, pancreas, breast, cervix, ovaries, bladder, bone, combinations thereof, pain associated therewith, or the like. Such applications may include delivery of compositions to slow, to reverse, and/or to prevent perineural and/or lymphatic vessel invasion of a cancerous tumor into a surrounding neural and/or lymphatic microenvironment, to interrupt, decrease, and/or stop neural communication to/from a cancerous tumor and/or the microenvironment surrounding the tumor to a remote site within a body, etc.

In aspects, one or more systems, methods, or compositions in accordance with the present disclosure may be used to treat one or more conditions of the central nervous system, the enteric nervous system, the limbic brain, etc. Some non-limiting examples, include treatment of seizure foci, hyperactive neurological regions, neuroendocrine/GI structures, pancreas/b-islet cells for DM, production of ghrelin and other GI hormones, combinations thereof, or the like.

In aspects, one or more non-limiting applications in oncology include sensing and ablation of CNS tumors with chronic release (e.g., CNS tumor with absence of electrical signals indicative of a tumor region, etc.). In aspects, the tumor margin may be determined by monitoring the electrical signals associated with the electrophysiologic activity of nearby cells, the activity changing across the margin of the tumor. In aspects, the tumor margin may contribute to considerable neural sprouting, the electrical signals measured by a device in accordance with the present disclosure may change considerably (i.e., as compared with normal tissue electrophysiologic activity), in the vicinity of the neural sprouting region.

In aspects, a delivery system or injection device in accordance with the present disclosure may take the form of a guidewire or a catheter. The guidewire may be dimensioned and configured for placement within a lumen of a body at and/or beyond a surgical site and/or anatomical site of interest, so as to monitor one or more physiologic signals near the tip thereof. In aspects, the guidewire may provide a pathway for delivery of a second surgical device to the surgical site.

In aspects, a guidewire in accordance with the present disclosure may include one or more energy delivery means for delivering energy to an anatomical site within and/or beyond the wall of a lumen into which the guidewire tip has been placed.

In aspects, a guidewire in accordance with the present disclosure may include one or more sensors (e.g., as located on a micro-tool-tip, a clamp, a hook, a wire element, an electrode in a matrix, etc.) near to the tip thereof. One or more sensors may include a pressure sensor, a tonal sensor, a temperature sensor, an electrode (e.g., size, oriented, and configured to interact with a local tissue site, provide a stimulus thereto, measure a potential therefrom, monitor current to/from the tissues, to measure, dependent on configuration and design, a bioimpedance, measure an evoked potential, an electromyographic signal [EMG], an electrocardiographic signal [ECG], an extracellular potential from a nearby neural structure, a local field potential, an extracellular action potential, a mechanomyographic signal [MMG], local neural traffic, local sympathetic nerve traffic, local parasympathetic nerve traffic, afferent nerve traffic, efferent nerve traffic, etc.), an acoustic sensor, an oxygen saturation sensor, or the like.

In aspects, the catheter or guidewire may be equipped with a substance eluting element, configured to deliver energy or a composition in accordance with the present disclosure, a substance, a medicament, a denervating substance, or the like into the target organ, into the tissues surrounding the wall of the lumen, etc.

In aspects, the energy and/or substance/composition is delivered to interrupt and/or augment neural traffic along one or more nerves coupled to the target organ. In aspects, the energy and/or substance is provided so as to block nerve traffic to and/or from the organ along the lumen into which the distal tip has been inserted.

In aspects, the substance may include a neural agonist or neural antagonist. The substance may be delivered to a site whereby the active agent (agonist/antagonist) may be released into the target neural structures, so as to augment neural function over a prolonged period of time. Such an approach may be advantageous to selectively treat neural structures without releasing significant amounts of the agonist/antagonist into the general blood stream of a subject (i.e., so as to treat a target site with maximum efficacy while minimizing systemic levels of the agonist/antagonist).

In aspects, a system in accordance with the present disclosure may be used to treat pain, pain associated with perineural invasion of a cancerous tumor, or the like. Such a system may be advantageous for treating such pain durably and with minimal side effects. Furthermore, such a system may be directed to treat nerves in the vicinity of the tumor without affecting ganglia or CNS structures, thus reducing the chances of side effects, complications, and the like.

In aspects, a system, device, and/or method in accordance with the present disclosure may be used to treat and/or slow the progression of a cancerous tumor. Some non-limiting examples of such cancer that may be treated include cancer of the prostate, pancreas, breast, colon, skin, liver, esophagus, cervix, bone, urogenitals, lung, and the like. In aspects, the progression may be slowed by blocking of neural and/or lymphatic pathways as may otherwise provide conduits for metastasizing tumor cells.

In aspects, a system, device, and/or method in accordance with the present disclosure may be used to slow, hinder, and/or prevent perineural or peri-lymphatic invasion of a cancerous tumor into a surrounding nerve or lymphatic structure.

In aspects, a system, device, and/or method in accordance with the present disclosure may be used to interrupt, decrease, and/or stop neural communication to a cancerous tumor and/or the microenvironment surrounding the tumor (i.e., to interrupt nerve traffic to/from a cancerous tumor or the tissues thereby to the rest of the body).

In aspects, a system, device, and/or method in accordance with the present disclosure may be used to decrease pain signals communicated by nerves in the vicinity of the organ and/or tumor to one or more neural circuits, ganglia, etc.

In aspects, a system, device, and/or method in accordance with the present disclosure may be used to block, deaden, and/or to destroy nerves in the vicinity of a tumor and/or surrounding tissues.

In aspects, a system, device, and/or method in accordance with the present disclosure may be used to slow or even halt tumorigenesis of cancerous tissue.

In aspects, a composition and/or delivery method in accordance with the present disclosure may be configured to form a physical barrier (i.e., lesion, a collagen block, etc.) along a neural structure and/or a lymphatic structure in a body.

In aspects, the composition may include an antibody drug conjugate (ADC), a chemotherapeutic agent, a toxin, a neurotoxin, etc. In aspects, the ADC may be configured to affect the function of a region or tissue type within the vicinity of the organ alternatively to the other tissues within the vicinity thereof. In aspects, the composition may include a sugar attached to a therapeutic agent to mask the therapeutic agent, such that it is to be taken up by the region of tissue (i.e., appear as a sugar, a friendly protein, etc.). Such a configuration provides a method for delivering a highly potent medicament directly to a tissue of interest (i.e., directly into a tumor), so as to enhance the bioavailability thereof, and to minimize the systemic dosage required in order to achieve significant therapeutic concentrations thereof within the region of tissue.

In aspects, the composition may be delivered at a rate of less than 1 mg/sec, 1 mg/min, 1 mg/hr, 0.01 mg/hr, less than 1 µg/hr, or the like. Such a configuration may be important so as to minimize local stress and damage caused by the introduction of the composition into the microenvironment of the tissue of interest.

In aspects, the composition may be formulated such that the ablative agent is released from a delivered bolus (e.g., such as a 25 µg bolus, a 100 µg bolus, a 600 µg bolus, a 1 mg bolus, etc.) into the surrounding tissues at a rate of less than 500 mg/sec, less than 50 mg/sec, less than 500 mg/min, less than 100 g/hr, or the like. In aspects, a slow release formulation may be used so as to functionally disable a tissue site in a body without causing local cell death. Such a configuration may be advantageous for performing a substantially durable and reversible treatment of tissues in a body. In aspects, an active agent may include a phenol, an alcohol, etc. and the composition may include a metabolically cleavable bond (e.g., a sugar, a cellulose chain, etc.) to which the active agent may be bound. Such slow metabolic cleavage of the bonds may allow for exceptionally slow release of the active agent into the surrounding tissues. Such a configuration may be advantageous to control ethanol elution in time and space near to a target tissue site in a body over a period of seconds, minutes, hours, days, weeks, or even longer.

In aspects, a delivery system in accordance with the present disclosure may include a catheter and/or a guidewire configured for percutaneous access to the arteries, veins, or lumens, of a body, for delivery through one or more arteries of the body to the vicinity of the target organ.

In aspects, one or more energy delivery elements, sensing elements, a diameter of the catheter, guidewire, or the like may be sized and arranged such that it may be placed within an artery, vein in a region near the target organ, within the parenchyma of the target organ, into a vessel in the periosteal space of a bone, and/or through a foramen of a bone. In aspects, the delivery elements and/or sensing elements, catheter, guidewire, etc. may be sized and dimensioned such that a characteristic diameter thereof is less than 2 mm, less than 1 mm, less than 0.75 mm, less than 0.5 mm, less than 0.3 mm, or the like.

In aspects, a method in accordance with the present disclosure may be used to treat prostate cancer, pancreatic cancer, breast cancer, colon cancer, cervical cancer, ovarian cancer, bladder cancer, bone cancer, or the like.

In aspects, a system in accordance with the present disclosure may include a substance delivery aspect, configured for elution of a substance into the vicinity of the target.

In aspects, the micro-tool tip may include a substance delivery needle for providing a drug substance to one or more of the nerves to perform the ablation.

In aspects, the micro-tool tip may include an energy delivery means, for providing an ablating current, ultrasound energy, high intensity focused ultrasound (HIFU), MR guided HIFU, thermal energy, microwave energy, cryogenic change, etc. to one or more of the nerves.

In aspects, the delivery system may include a signal conditioning circuit and a processor for identifying the presence and/or characterizing one or more of the nerves, to generate a feedback signal therefrom, and to coordinate the energy or substance delivery based upon the feedback signal.

In aspects, the micro-tool tip may have a characteristic diameter of less than 2 mm, less than 1 mm, less than 0.5 mm, less than 0.25 mm, or the like to facilitate placement into the vessel.

In aspects, the micro-tool tip may include one or more electrodes in accordance with the present disclosure. One or more of the electrodes may be sized and dimensioned to measure the signal, and/or one or more of the electrodes may be sized and dimensioned to stimulate and/or ablate one or more of the nerves.

In aspects, the micro-tool tip may include a plurality of electrodes, each electrode configured for sensing an electrophysiological signal in accordance with the present disclosure in the vicinity thereof, the electrodes electrically isolated from each other such that the collection of locally collected signals may be used to determine activity over region of tissues in the vicinity of the vessel.

Figure 1B:
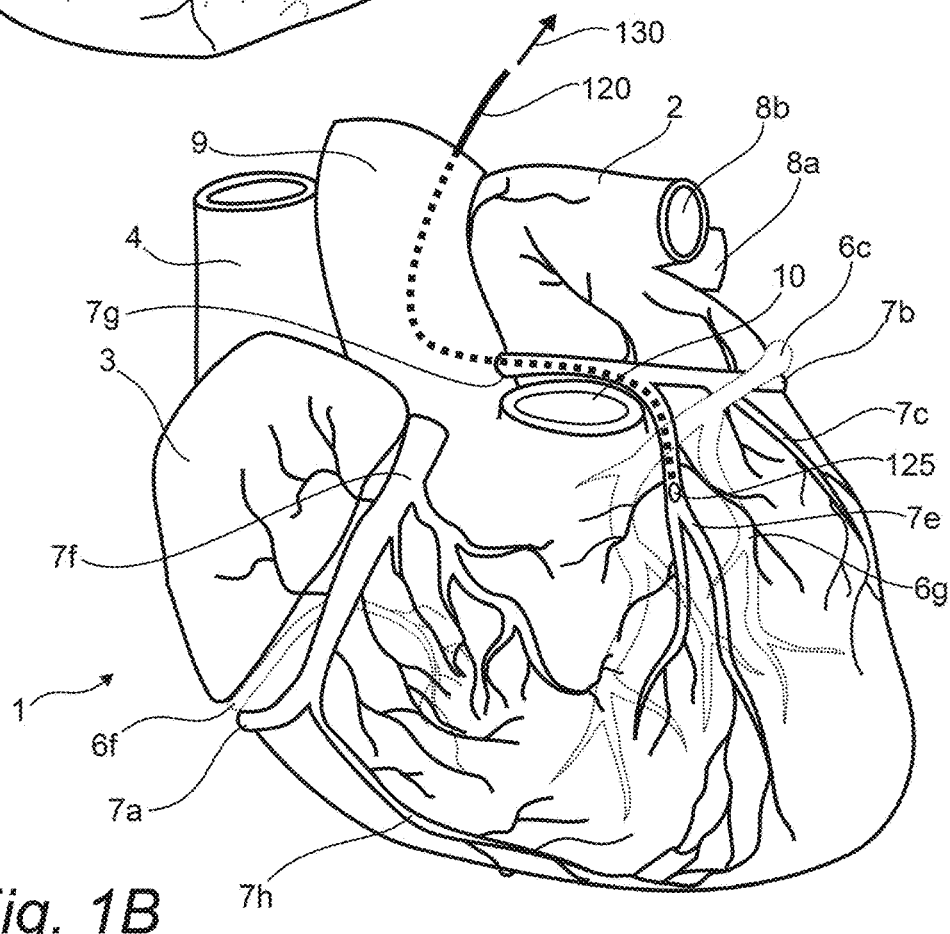

FIGS. 1A and 1B show catheter access routes into various coronary vessels of a human heart 1. The coronary vessels are arranged around the heart along with autonomic innervation, thus allowing access to the innervation for methods and devices in accordance with the present disclosure. Thus the coronary vessels may provide a pathway to reach diseased sites of innervation around the heart, so as to provide treatment with an associated interventional device. FIG. 1A shows the heart 1 with a left atrium 2 coupled to four pulmonary veins 8a-d, a right atrium 3 coupled with a superior vena cava 4 and an inferior vena cava 5. The coronary sinus 6a may be accessible through the right atrium 3 and connects to other coronary veins including a small cardiac vein 6f, a middle cardiac vein 6d, a left posterior ventricular vein 6b, a great cardiac vein 6c, an oblique vein 6e of the left atrium 2, and a left marginal vein 6g (shown in FIG. 1). Also shown is the circumflex branch of the right coronary artery 7a, the posterior interventricular branch of the right coronary artery 7i, the posterior left ventricular branch of the left coronary artery 7c, the circumflex branch of the left coronary artery 7b, and the posterior interventricular branch of the left coronary artery 7d. A device 100 in accordance with the present disclosure is (e.g., a sensing catheter, a delivery catheter, a combination thereof, etc.) is shown with an effector 105 placed within the coronary sinus 6a, and in communication with an external controller 110. The effector 105, may include one or more sensing elements, one or more delivery needles, one or more secondary sensors, etc. each in accordance with the present disclosure. The effector 105 may include one or more radiopaque markers to assist with locating the effector 105 in relation to other features on the heart 1.

In aspects, the effector 105 may include a delivery element in accordance with the present disclosure, the delivery element configured so as to be deployable through the wall of the coronary vein in which the effector 105 is placed, so as to deliver a substance, energy, etc. to a nearby tissue, a vein wall, adventitia around the vein, a region of tissue, a muscle, a region of tissue on the left atrium 2, a diseased region, a lesion, or the like.

In aspects the effector 105 may include one or more sensing elements in accordance with the present disclosure, each sensing element configured to measure a local electrophysiologic signal to assist in the localization of therapeutic targets, localize sympathetic, parasympathetic, or somatosensory nerves, assess local neural traffic, assess local smooth muscle function, assess local cardiac function, map functionality, map neural interconnectivity, assess interconnection of neural traffic, find local ganglia, apply signals, substances, form a blockage, or the like for one or more diagnostic tests, support therapy and confirm delivery of therapy, or the like. In aspects, the sensory catheter may be integrated with a therapeutic modality in accordance with the present disclosure to provide a full feedback integrated device.

Such a system may be advantageous for providing ultra-high spatial and spectral fidelity mapping of the local neural structures, and functional interface with the cardiac nerves for diagnostic, and therapeutic purposes.

In aspects, a coronary venous approach may be advantageous for accessing one or more sensory nerves, one or more parasympathetic nerves, or the like along the outer surface of the heart. Such nerves may be treated with a device in accordance with the present disclosure to reduce cardiac pain, augment local coronary vein vasoconstriction/vasodilation, assess local neural function, apply one or more stress tests to a local coronary vein, or the like.

FIG. 1B illustrates a heart 1 coupled with an ascending aorta 9, a left coronary artery 7b and a right coronary artery 7f coupled thereto. The left coronary artery 7b is shown coupled to the anterior interventricular branch 7e and the left marginal branch 7c coronary arteries. The right coronary artery 7f is shown coupled to the right marginal branch 7h and the posterior interventricular branch 7a. Also shown are coronary veins including the small cardiac vein 6f, and the great cardiac vein 6c. As shown, the left coronary artery 7b emerges from the aorta 9 and passes between the right atrium 2 and the pulmonary trunk 10. Alternatively, the right coronary artery 7f passes along the right atrium 3 before branching and heading down towards the ventricles. Access to one or more neural structures such as autonomic ganglia along may be made with one or more devices in accordance with the present disclosure through the walls of these vessels.

Also shown is a device 120 in accordance with the present disclosure, passing through the aorta 9 and into the left coronary artery 7b and down into the anterior intraventricular branch 7e thereof. The device 120 is coupled proximally with an operator 130, and includes an effector 125, the effector 125 including one or more sensory elements, sensing tips, delivery elements, electrodes, sensors, combination thereof, or the like in accordance with the present disclosure.

In aspects, the effector 125, may include a delivery element in accordance with the present disclosure, the delivery element configured so as to be deployable through the wall of the coronary vein in which the effector 125 is placed, so as to deliver a substance, energy, etc. to a nearby tissue, the artery wall, an adventitial space around the artery, nearby adipose tissue, functional tissues of the heart, a muscle, nearby sympathetic nerves, somatosensory nerves, a region of receptors, a diseased region of tissues, or the like.

In aspects the effector 125 may include one or more sensing elements in accordance with the present disclosure, each sensing element configured to measure a local electrophysiologic signal to assist in the localization of therapeutic targets, localize sympathetic, parasympathetic, or somatosensory nerves, assess local neural traffic, assess local smooth muscle function, assess local cardiac function, map functionality, map neural interconnectivity, assess interconnection of neural traffic, find local ganglia, apply signals, substances, form a blockage, or the like for one or more diagnostic tests, support therapy and confirm delivery of therapy, or the like. In aspects, the sensory catheter may be integrated with a therapeutic modality in accordance with the present disclosure to provide a full feedback integrated device.

Such a system may be advantageous for providing ultra-high spatial and spectral fidelity mapping of the local neural structures, and functional interface with the cardiac nerves for diagnostic, and therapeutic purposes.

Figure 2A:
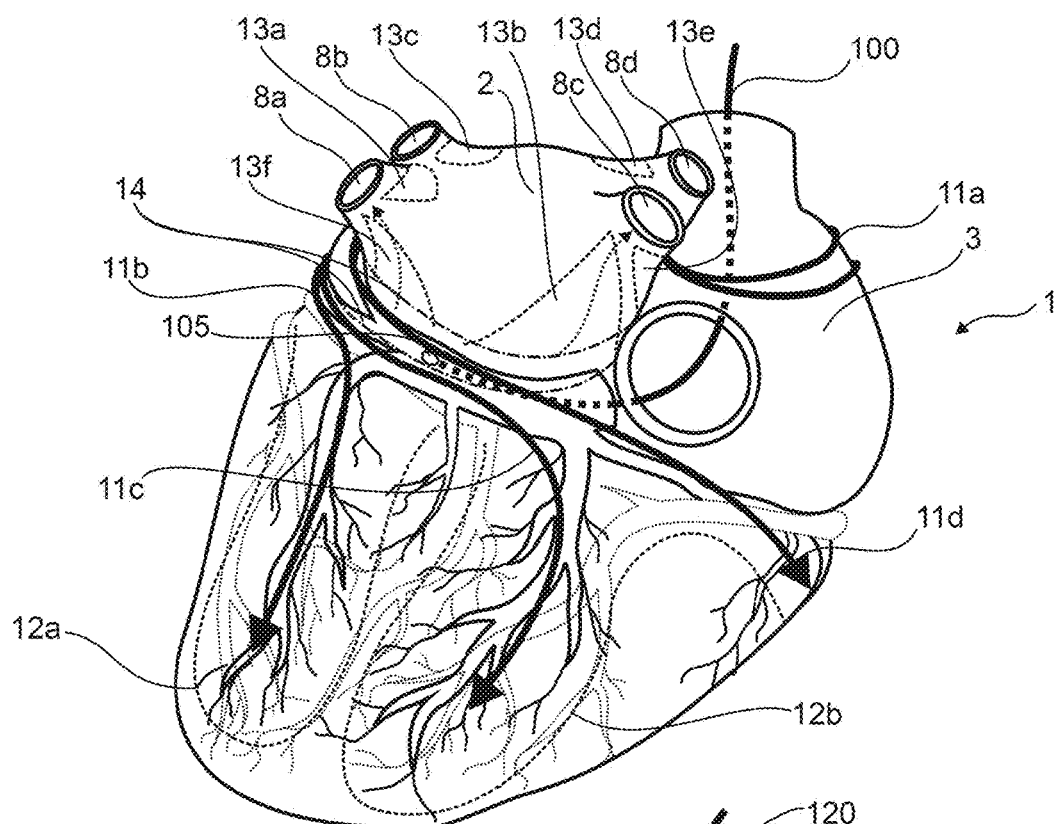
FIGS. 2A and 2B illustrate autonomic neural pathways overlaid on the coronary vessels and major anatomical features of a human heart.
Figure 2B:
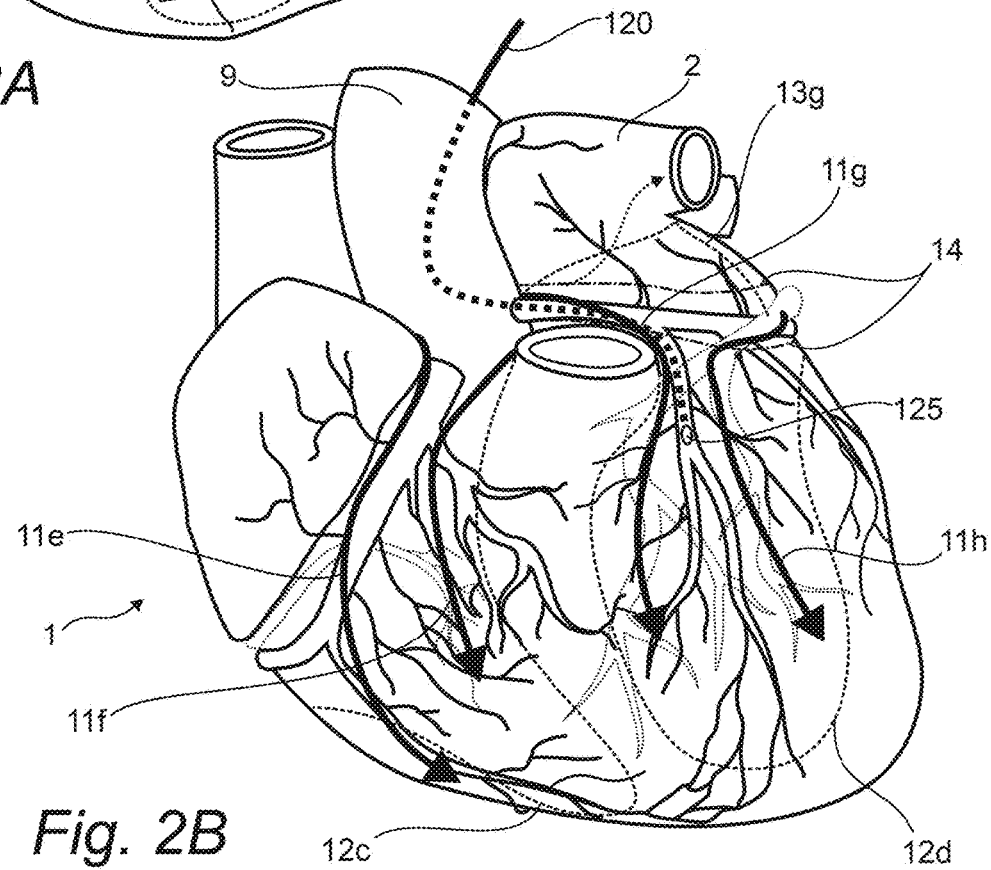

FIGS. 2A and 2B illustrate autonomic neural pathways overlaid on the coronary vessels and major anatomical features of a human heart 1. FIG. 2A illustrates pathways for various autonomic plexuses 11a, passing over the right ventricle 3, and other autonomic plexuses 11b-d passing along the coronary arteries and veins. The neural plexuses 11b-d generally continue along with the coronary vessels over the ventricles and spider outwards innervating the vessel walls, adipose tissue, and muscle. In aspects, access to various regions 12a,b of the autonomic innervation of the heart may be made via the corresponding coronary vessels. Networks of autonomic nerves also travel over various regions 13a-f of the left atrium 2 and to/from the pulmonary veins 8a-d.

In aspects, a method for isolating the left atrium 2 may include treating tissues in a zone 14 in the vicinity of the coronary arteries and veins traveling between the left atrium 2 and the ventricles of the heart 1. In aspects, isolation of other heart chambers may be achieved by treating tissues with a device in accordance with the present disclosure via access provided along one or more coronary arteries or veins. Such an approach may be advantageous to establish a durable left atrium 2 isolation without excessive damage or scarring to the heart tissues, or the need to dissect regions of the heart to access the target tissues, etc. In addition, one or more regions along the right/left atrium septum, along the inferior vena cava, the superior vena cava, and/or the ascending aorta may be targeted as part of such a therapy.

The device 100 shown in FIG. 2A is arranged in the coronary sinus 6a with the effector 105 positioned so as to interface with tissues of the left atrium 2, the walls of the coronary sinus 6a, or the like. In aspects, the effector 105 may include a delivery element configured so as to be oriented such that a therapeutic substance (e.g., a composition, an ablative agent, etc.) may be delivered locally into the walls of the left atrium 2 in accordance with the present disclosure. Such an approach may be advantageous to treat the tissues of the left atrium 2 while minimizing risk of damage to surrounding tissues, etc. The effector 105 may include one or more sensory elements to identify regions to be treated, monitor the treatment process, evaluate stress response of tissues, and evaluate the continuity of the treatment (e.g., gaps in the block, distance between an already treated site and the next site for treatment, etc.), a combination thereof, or the like.

FIG. 2B illustrates an anterior view of the heart 1 illustrating how various neural plexuses 11e-h pass along the aorta 9, around the coronary arteries and veins, and following the vessels down into the ventricles of the heart 1. As shown, a device 120 in accordance with the present disclosure, may be directed towards one or more target regions 12c,d of nerves via the corresponding coronary arteries, so as to perform one or more treatments in accordance with the present disclosure thereupon. As evident from FIGS. 2A and 2B, a range of vessels may be used by a device in accordance with the present disclosure to find diseased regions of the heart 1, assess regions of the heart 1, and to treat various regions of the heart 1 in a very spatially localized way.

In aspects, the effector 125 of the device 120 may include one or more sensory elements in accordance with the present disclosure, the sensory elements configured so as to monitor one or more electrophysiologic signals at a nearby region of the heart 1. In aspects, the sensory elements may be locally coupled with a high fidelity amplifier (i.e., arranged nearby in the body of the device 120), so as to extract one or more broadband neural signals, a region of interest, perform an ultralow noise recording of the nearby tissue, or the like. Such an approach may be advantageous to measure small neural signals, heterogeneously distributed neural signals, or the like, which may be masked by the larger myocardial action potentials, movement noise, or the like.

In aspects, the sensors or nearby amplifiers may be coupled with one or more movement artifacts, or spaced so as to help eliminate a large myocardial signal, such that the amplifier gain may be greatly increased. Further, the amplifier may be equipped with an analog to digital converter (ADC), optionally with oversampling functionality, the ADC configured so as to oversample the signal so as to further drop the noise floor thereof. In aspects, such a technique may be advantageous for dropping the noise floor more than 1 dB, more than 3 dB, more than 6 dB, more than 9 dB, more than 12 dB, or the like so as to enhance the quality of the captured signal (i.e., in circumstances wherein the signal is sufficiently small to warrant such resampling). Such an approach may be advantageous to simultaneously remove unwanted characteristics of a signal, while further dropping the noise floor so as to enhance the signal capture therefrom. In aspects, the ADC may be configured with greater than or equal to 8 bit precision, greater than or equal to 10 bit, greater than or equal to 12 bit, greater than or equal to 16 bit, or the like. The ADC may be configured with the oversampling function so as to effectively increase the precision by 1 bit, greater than 1 bit, greater than 2 bits, greater than 3 bits, or the like. Such an approach may be advantageous to reduce the size of the ADC while providing sufficiently high signal capture of neural signals in the vicinity of one or more of the sensing elements.

In aspects, the amplifier may be configured so as to amplify a broadband signal nearby a sensing element in accordance with the present disclosure. The amplifier may be configured with one or more stages, and with a pass band of greater than 1 mHz to 40 kHz, including 100 mHz-3 kHz, specifically 100 mHz-1 kHz, or the like. The amplifier may include functionality so as to be configurable in terms of gain and/or bandwidth. Thus during a measurement session, the amplifier may be first configured in a broadband mode, so as to capture as much of a signal as possible. Upon analysis of the captured signal, the amplifier may be adjusted so as to hone in on key information in the signal (e.g., such as high frequency content thereof, a movement artifact, a low bandwidth signal, so as to optimize the capture of a particular neuronal action potential train, to optimally capture a low frequency potential, to remove one or more components of a signal, etc.).

Figure 3A:
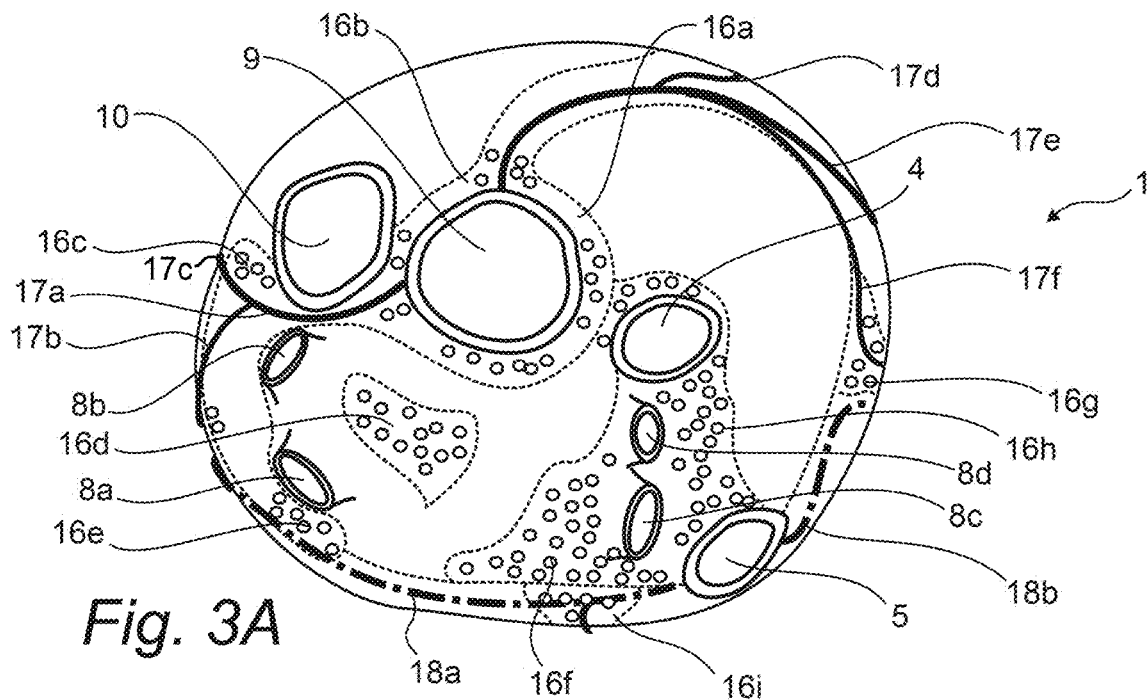
FIGS. 3A and 3B illustrate the approximate locations of various autonomic ganglia in relation to various coronary vessels and major anatomical features of a human heart.
Figure 3B:
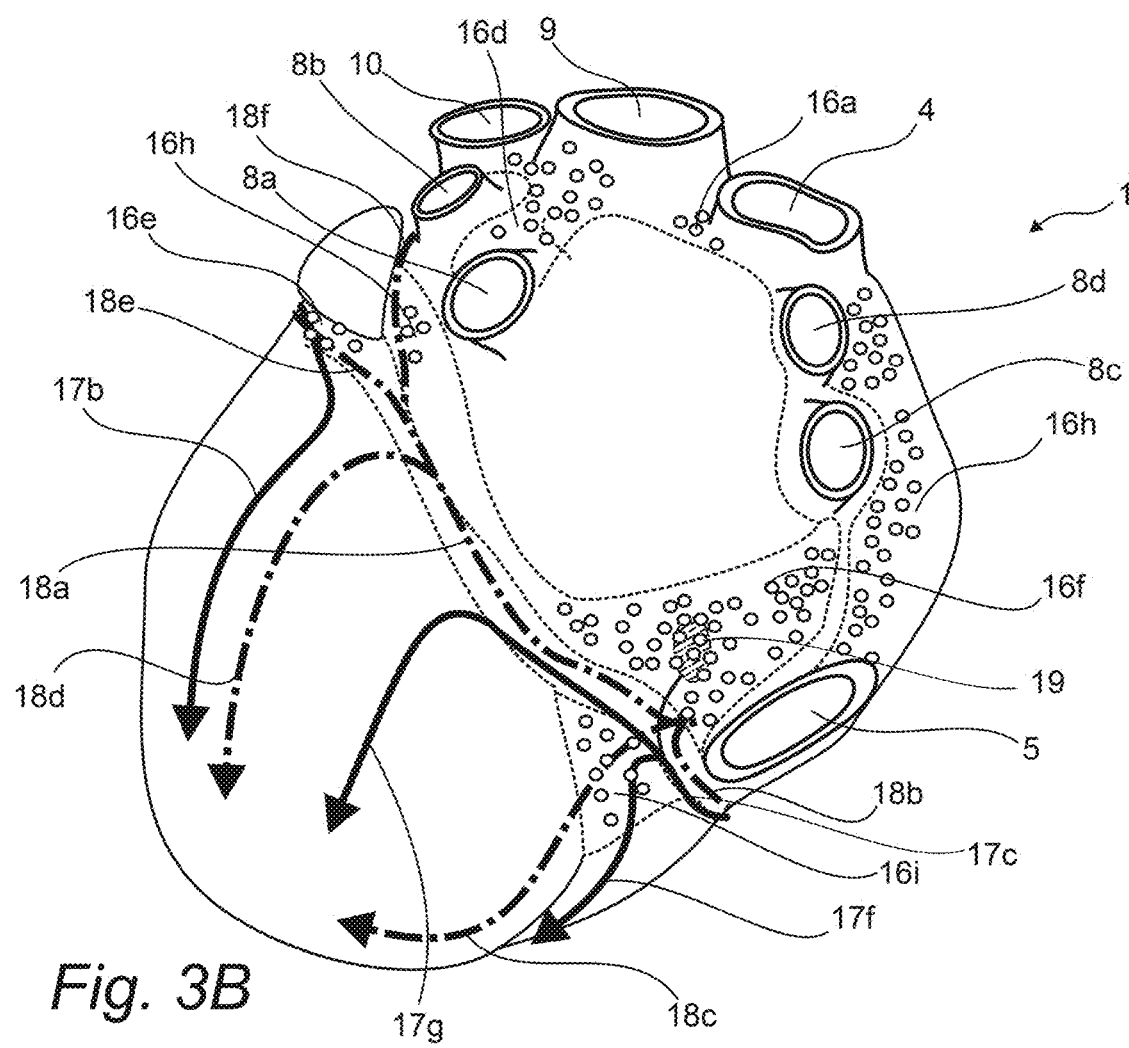

FIGS. 3A and 3B illustrate the approximate locations of various autonomic ganglia in relation to various coronary vessels and major anatomical features of a human heart. FIG. 3A shows a superior view of a heart 1, while FIG. 3B shows a posterior view, each illustrating a range of ganglia 16a-i arranged around the major vessels 4, 5, 8a-d, 9, 10 of the heart 1. As visible in the views, the ganglia 16a-i are generally situated around the regions around which the major vessels 4, 5, 8a-d, 9, 10 connect with the heart 1 and along the coronary arteries 17a-g and coronary veins 18a-f. Such arrangements and positioning of ganglia 16a-i are highly variable from subject to subject, and as such a sensing tool in accordance with the present disclosure may be configured to locate such ganglia, assess inter-ganglia connectivity, or the like during a procedure. In addition, a therapeutic tool, or diagnostic tool may be used to treat ganglia, to break up aberrant signal pathways, or the like alone or associated with one or more sensing elements in accordance with the present disclosure as providing procedural feedback or the like.

FIG. 3B also illustrates the location of the atrioventricular node (AV node) 19 located near the right coronary artery 17c. The sinoatrial node (SA node), not shown for clarity, is often provided with blood from the right coronary artery 17c as well but may be supplied via the circumflex branch of the left coronary artery (roughly 55% right coronary artery (RCA), 43% left coronary artery (LCA)). The AV node 19 is more often supplied by the right coronary artery (roughly 75% RCA, 25% LCA). In general, it has not been reported that such nodes are simultaneously supplied by both coronary arteries.

Some ganglia that may contribute to complex fractionated atrial electrograms (CFAE) may be arranged around the atrial wall and include cardiac ganglionic plexi (GP), such as the superior left atrial GP, posterolateral left atrial GP, posteromedial left atrial GP, anterior descending GP, posterior right atrial GP, superior right atrial GP, and the like. High fidelity sensing may be advantageous for localizing such GP in cardiac tissues so as to guide a diagnostic test, an ablation procedure, a therapy, a mapping procedure, a combination thereof, or the like with a method, sensing catheter, mapping catheter, or the like each in accordance with the present disclosure.

Figure 4:
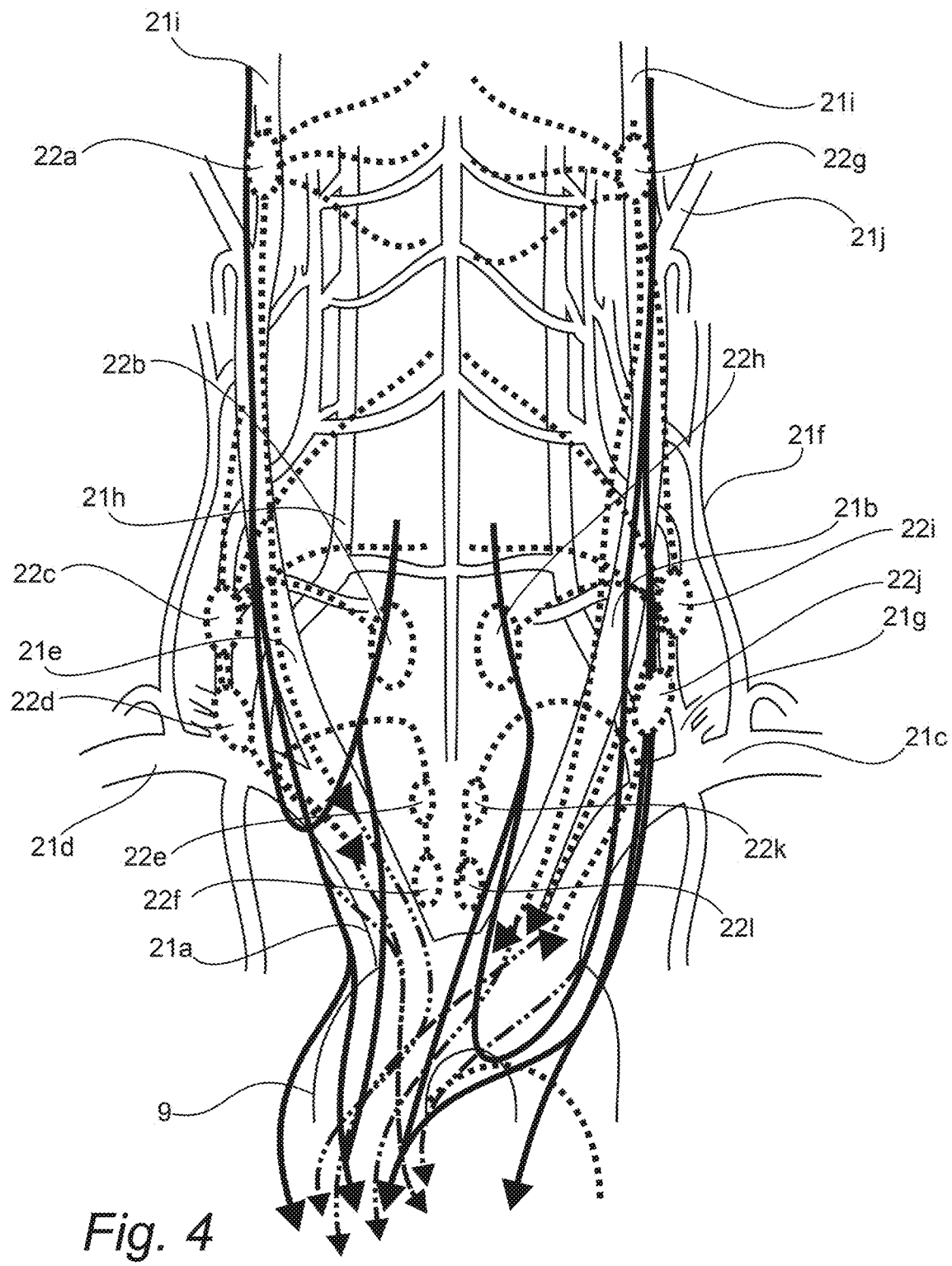
FIG. 4 illustrates the approximate positional relationships between the major arteries of the head, neck, and heart overlaid by autonomic neural plexuses innervating a human heart.

FIG. 4 illustrates the approximate positional relationships between the major arteries of the head, neck, and heart overlaid by autonomic neural plexuses innervating a human heart. The figure shows the ascending and descending aorta 9 coupled with the brachiocephalic trunk 21a, the left common carotid artery 21b, and subclavian arteries 21c, which are in turn coupled with the right subclavian artery 21d, the right common carotid artery 21e, the cervical arteries 21f, the thyroid arteries 21g, the vertebral arteries 21h, the internal carotid arteries 21i, the external carotid arteries 21j, and the like. Overlaid on the arteries are segments illustrating innervation traveling from ganglia 22a-1 and the central nervous system to the heart. Shown are plexuses primarily including parasympathetic nerve fibers (solid lines), plexuses including primarily sympathetic nerve fibers (dotted lines), and mixed plexuses (dot-dash lines). As can be seen, as the plexuses travel along the arteries to the heart, the plexuses become more mixed, such that as the plexuses travel to the heart, primarily entering along the major vessels (including the ascending and descending aorta), they are often of mixed variety.

Generally afferent and efferent fibers are collocated in plexuses. A sensing system in accordance with the present disclosure may be used to locate plexuses along one or more of the arteries shown, engage with one or more nerves or ganglia for purposes of analysis, etc. One or more therapeutic systems, delivery systems, ablation systems, or the like may be configured so as to engage with one or more nerves, plexuses, ganglia, etc. along one or more of the arteries in the head and neck, so as to treat the nerves locally, perform a block, a durable, block, or the like in accordance with the present disclosure.

As seen in FIG. 4, many of these nerves are arranged around arteries connecting the region of the aortic arch to the spine. Such pathways provide natural access to therapeutic targets, such as the carotid body one or more plexuses, etc.

Also shown are nerve plexuses entering along the ascending aorta 9. Thus a plurality of sensory catheters each in accordance with the present disclosure may be configured to map locations along the arterial walls that correspond to aberrant traffic as measured in and around the aorta 9 near the heart. Such nerves also pass along the pulmonary artery, pulmonary veins, etc.

FIGS. 5A-5C illustrate the autonomic innervation into the heart and the innervation around the major vessels coupled with a human heart. FIG. 5A illustrates the basic CNS cardiac control centers and the interconnection between those centers and the heart 1. FIG. 5A shows various parasympathetic plexuses primarily extending from the medulla oblongata 23a, via the vagus nerve 24a, towards the heart 1. The preganglionic sympathetic plexuses 24d,e couple nerves in the spinal cord 23b to sympathetic ganglia 24b,c generally cervical ganglia and superior thoracic ganglia (T1-T4). Sympathetic post ganglionic plexuses 24f and generally travel along with the cardiac nerve (along 24d, through 24b, and 24f), toward the heart 1. Shown are the superior vena cava 4, the pulmonary trunk 10, and the aorta 9 along which many of the plexuses travel as they couple to the heart 1.

FIG. 5B shows a close up illustration of various plexuses along the ascending aorta 9, the pulmonary trunk 10, and the right atrium 3, at the base of the heart 1. The plexuses 25a-e are seen traveling around and among the large vessels, down along the right coronary artery 7f, and the like. One or more methods or devices in accordance with the present disclosure may be configured to access such nerves directly and locally at these sites, for purposes of mapping, treating, ablating, etc. A ganglion 25c is shown among the neural plexuses.

FIG. 5C shows a close up of the ascending aorta 9, the left atrium 2, and the pulmonary trunk 10 illustrating the plexuses 25f-j traveling among the major vessels and into the left coronary artery 7b, and the great vein 6f. Such vessels may be ideal access points for treating target nerves in the vicinity of these locations on the heart 1. Treatment of such nerves may be performed so as to treat a range of rhythm disorders, re-route neural pathways, disconnect one or more local ganglia, isolate a ganglion, limit neuroplastic growth, perform a local sympathetic neural blockade, or the like in accordance with the present disclosure.

Figure 6:
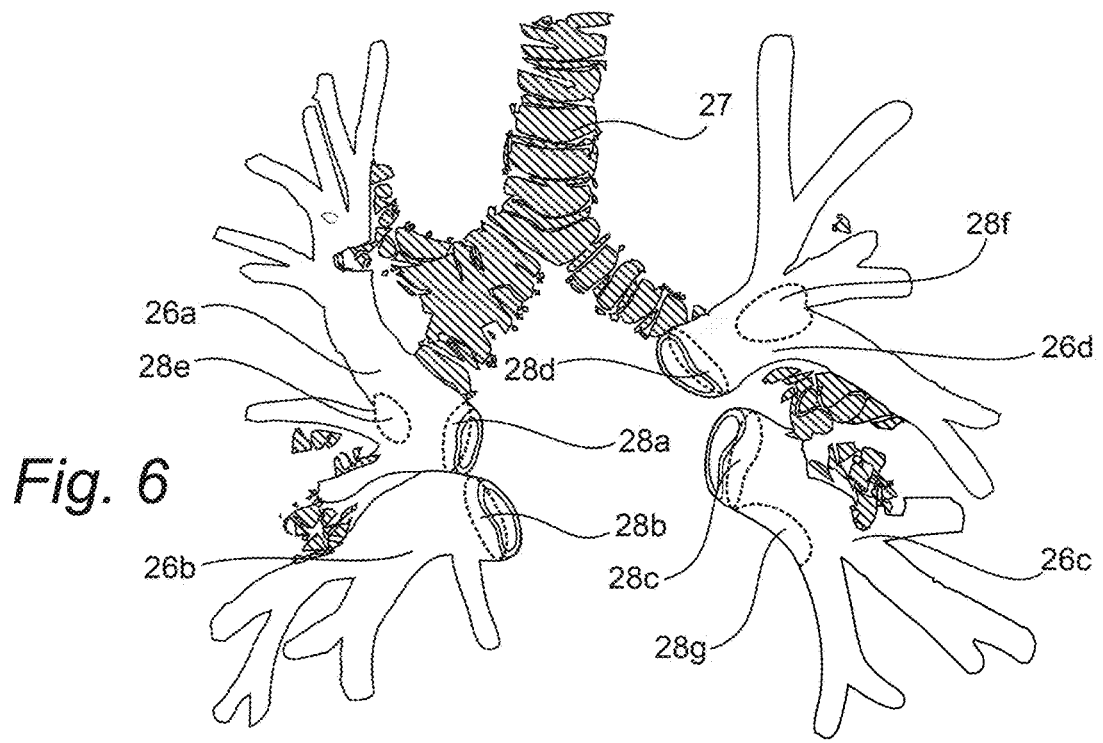
FIG. 6 illustrates regions of the pulmonary veins and target therapeutic zones.

FIG. 6 illustrates regions of the pulmonary veins and target therapeutic zones. FIG. 6 shows pulmonary veins 26a-d and the bronchial tree 27. Overlaid on the pulmonary veins 26a-d are some non-limiting examples of target treatment zones 28a-g. The treatment zones 28a-g may be the targets of a neural ablation procedure, a neural block, a parasympathetic block, a stem cell therapy, a neural growth factor therapy, or the like in accordance with the present disclosure. Such procedures may be used to regenerate damaged tissue, repair damaged tissue, isolate diseased tissues, remodel diseased tissues, perform a pulmonary vein isolation procedure, a combination thereof, or the like. A sensing system in accordance with the present disclosure may be suitable for accessing, locating, functionally evaluating, testing, coordinating therapy, confirming therapy, confirming therapy extents, confirming therapy efficacy, or the like on one or more of the target sites (or one or more alternative sites). The pulmonary veins 8a-d, 26a-d may be accessed via the heart (left atrium), via an external approach, or the like.

In aspects, one or more treatment zones may be out in the pulmonary vein ostium 28e-g, where a diseased tissue site, aberrant neural plexus, or positive neural feedback loop is located. Furthermore, a therapy for causing a continuous ablation for pulmonary vein isolation without excessive tissue damage, charring, necrotic tissue, or the like is present, thus allowing for treatment without as many adverse events, etc. The treatment zones 28a-d show a formed continuous ablation around the bases of the pulmonary vein 26a-d, left atrium 2 interfaces. In aspects, a high fidelity neural sensing system in accordance with the present disclosure may be used to detect the regions in need of treatment 28a-g. In aspects, an ultra-precise chemical ablation system in accordance with the present disclosure may be used to treat the regions in need of treatment 28a-g. In aspects, the high fidelity sensing system may be used to determine the extent of ablation, determine if finished, identify other targets, and monitor changes in the neural traffic flow and neural feedback after completion of an ablation/neural block, combinations thereof, or the like.

Figure 7A:
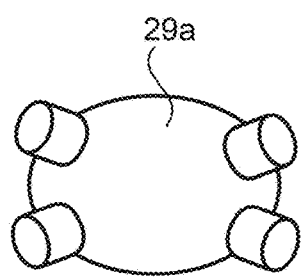
FIGS. 7A-7F illustrate the human left atrium and common anatomical variations encountered in practice.
Figure 7B:
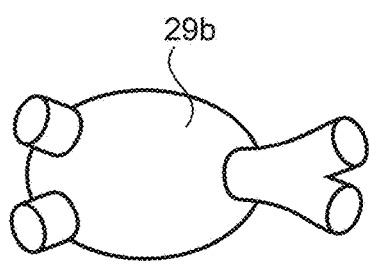
Figure 7C:
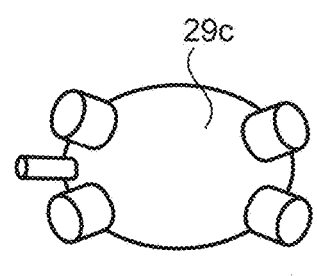
Figure 7D:
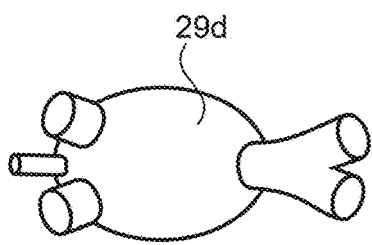
Figure 7E:
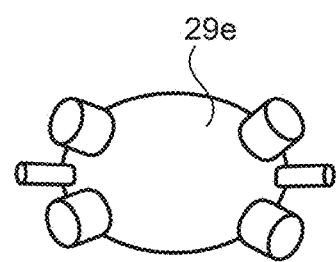
Figure 7F:
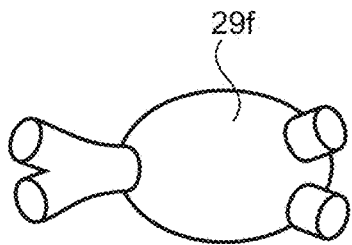

FIGS. 7A-7F illustrate the human left atrium and common anatomical variations encountered in practice. A treatment may be directed to one or more sites along the left atrium wall 29a-f, along the perimeter of the left atrium, along the interface between the atrium and one or more vessels, at sites out into the vessel ostia, etc. FIG. 7A illustrates the most common human anatomical variant, while FIGS. 7B-7F illustrate other common anatomical variants that may be encountered during a treatment, mapping, or diagnostic procedure in accordance with the present disclosure.

In aspects, one or more electrodes may be used to stimulate tissues during monitoring, after ablation, to test a temporary block, etc.

Figures 8A, 8B:
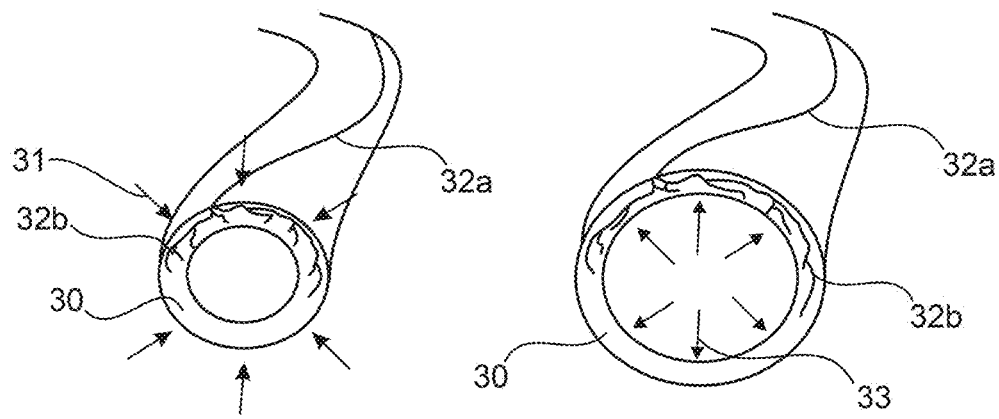
FIGS. 8A and 8B show a coronary vessel during contraction and dilation.

FIGS. 8A and 8B show a coronary vessel during contraction and dilation. FIG. 8A shows a coronary vessel 30 contracting 31 in response to neural traffic from fibers 32a,b located in the walls and surrounding adventitia thereof. Such nerves 32a,b may be directly innervating the smooth muscle of the vessel 30 directly, may interface with one or more sites in the adventitia (i.e., surrounding adipose tissue), may be related to neuroplastic changes in sensitivity, receptor quantity, etc. in the vicinity of the site, etc. FIG. 8B shows the coronary vessel 30 dilating 33 in response to neural traffic from fibers 32a,b innervating the vessel 30. In states of health, such innervation contribute to healthy tone of the coronary vessels, contraction, dilation, receptor function, sensitivity, long-term tone, and the like. In states of disease, such neural circuits may be damaged contributing to aberrant activity of the vessel (e.g., spasm, plaque growth, etc.). Monitoring and/or treatment of this traffic may allow for highly localized treatments, without the systemic side effects of pharmacologic treatment options.

Such contraction and dilation are at least partially influenced by autonomic innervation and neural traffic. Furthermore, the functional relationships between neural traffic and vessel response is complicated by inter-functional relationships between circulating hormone levels, circulating peptides, circulating neurotransmitters, and neuroplastic changes in local tissue receptor density, changes in neural ingrowth to the region, neural sprouting in response to damage, denervation caused by ischemia, neural ingrowth after ischemia, and the like. Thus a sensing system in accordance with the present disclosure may be suitable for testing the local functional relationships in a region, and determining the state of the functionality, whether a therapy is needed or not, what type of therapy will be most effective, etc. In aspects, a delivery system in accordance with the present disclosure may be used to apply a therapy to tissues in the vicinity of the coronary vessel, within the walls of the coronary vessel, along the coronary vessel, to drive neural regrowth to a vessel wall, to adjust the receptor density in the vicinity of a region of the vessel, to stop a neural sprouting process, to alter local neural growth factor levels, to denervate local tissues, to prevent restenosis of a vessel, etc.

Figure 9:
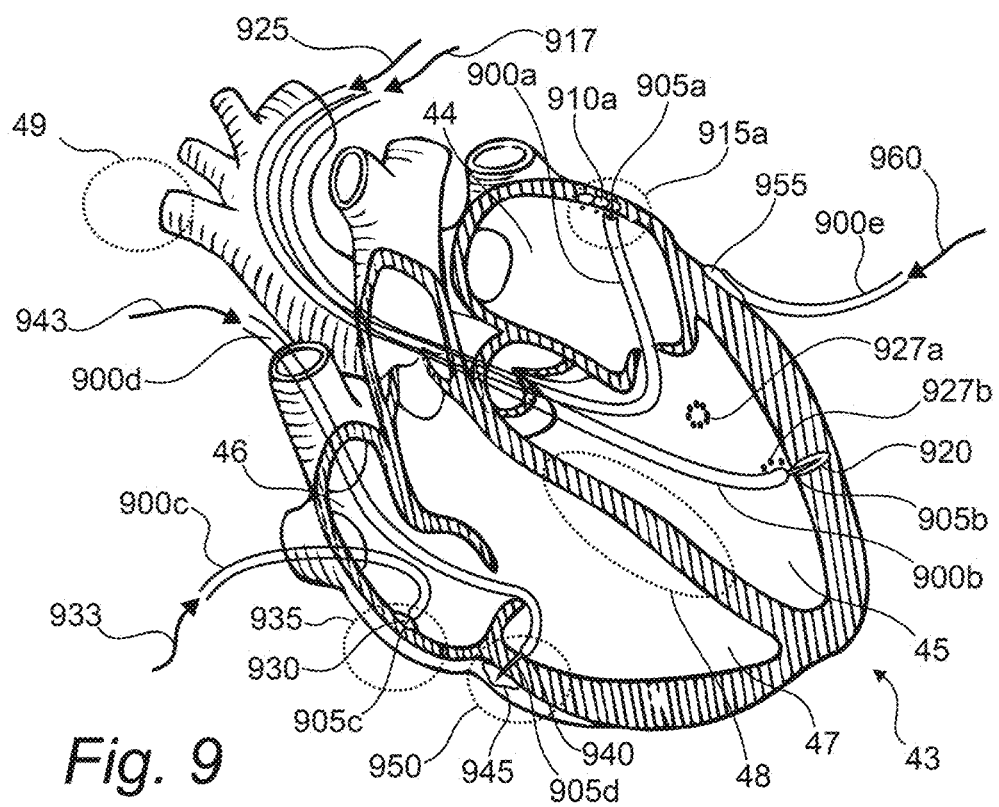
FIG. 9 illustrates internal structures of a human heart and systems and methods for accessing and treating regions thereof in accordance with the present disclosure.

FIG. 9 illustrates internal structures of a human heart and systems and methods for accessing and treating regions thereof in accordance with the present disclosure. FIG. 9 illustrates a heart 43 of a subject, and the placement and interaction of delivery tools 900a-e with cardiac tissues of the heart in accordance with the present disclosure. A delivery tool 900a in accordance with the present disclosure is shown accessing the left atrium 44 of the heart 43 through the aorta, the delivery tool 900a coupled to the wall of the left atrium 44, a needle-like delivery tip 905a in accordance with the present disclosure interfacing with the wall, a plurality of boluses 910a of a composition in accordance with the present disclosure delivered 917 through the delivery tool 900a and deposited into the wall of the left atrium 44 around a desired treatment zone 915a. In aspects, the delivery tool 900a may include tissue capture mean so as to limit the treatment zone 915a to just the wall of the left atrium 44 (so as to limit collateral damage to nearby organs, to prevent perforation of the esophagus, etc.).

A delivery tool 900b is shown coupled with the wall of the left ventricle 45 of the heart 43, the delivery tool 900b including a delivery tip 905b penetrating into the wall of the left ventricle 45, a bolus 920 of a composition in accordance with the present disclosure delivered 925 through the delivery tool 900b and into the wall of the left ventricle 45 (such as forming a pattern in accordance with the present disclosure). A plurality of previously injected delivery sites 927a,b are shown in the left ventricle, demonstrating patterning of the boluses so as to treat zones of the tissue in accordance with the present disclosure. In aspects, the delivery tip 905b may be advanced into the pericardium of the heart 43 so as to treat neural structures, cardiac muscle, etc. in that region (i.e., passing from the interior of the heart through the wall and into the external tissue sites).

A delivery tool 900c in accordance with the present disclosure is shown interfacing with the right atrium 46 of the heart 43, the delivery tool 900c advanced through the inferior or superior vena cava (entering the body through the basilic vein, the femoral vein, etc.), a delivery tip 905c biased against the wall of the right atrium 46, a bolus 930 of a composition in accordance with the present disclosure having been delivered 933 to the wall, the composition dwelling against the wall so as to treat a site thereof within a treatment zone 935 along the wall.

A delivery tool 900d in accordance with the present disclosure is shown interfacing with the right ventricle 47 of the heart 43, the delivery tool 900d advanced through the inferior or superior vena cava (entering the body through the basilic vein, the femoral vein, etc.), the tip thereof biased against the wall and a delivery tip 905d advanced into the wall, such that a tip is placed near to the pericardium of the heart, so as to interact with an autonomic nerve, a pericardial site, etc. One or more sensing elements 940 (sensors, electrodes, etc.) may be incorporated into the delivery tool 900d, or delivery tip 905d, in accordance with the present disclosure, to guide the tip for delivering 943 a bolus 945, to monitor electrophysiological activity before, during, and/or after delivery of the bolus 945, to assess the margin of the bolus 945, etc. in the vicinity of a treatment zone 950.

A delivery tool 900e in accordance with the present disclosure may be delivered to the pericardial sac or space of the heart 43 (e.g., such as endoscopically, transcutaneously, during surgery, etc.). The delivery tool 900e may be aligned with a treatment site and a bolus 955 of a composition in accordance with the present disclosure may be delivered 960 thereto to treat one or more tissues sites on or near the pericardium of the heart.

In aspects, a delivery tool 900a-e in accordance with the present disclosure may be used to access one or more treatment sites along, into, or in the vicinity of the vein of Marshall, the septum 48, a carotid sinus 49, a carotid body, the posterior left atrium, the great cardiac vein, the coronary sinus, the left superior cardinal vein, the oblique vein, the venous valve of Vieussens, etc.

A delivery tool 900a-e may include a sensor, an electrode, etc. in accordance with the present disclosure to assess the effect of the treatment, to assist with guiding the delivery tool 900a-e to the neural targets (e.g., via measuring local neural traffic, via stimulation of local tissues, etc.), assist with the assessment of margins of the bolus (e.g., by assessing impedance changes around the sensors, assessing the neural, and/or epicardial traffic around the sensors, etc.).

In aspects, a delivery tool in accordance with the present disclosure may include a plurality of tips, one or more deployable tips or tip arrays, etc. so as to treat a wide swath of tissues, to rapidly form a treatment pattern, etc. in the tissues.

In aspects, a device in accordance with the present disclosure may be placed at one or more sites in the heart 43 to generate a pacing signal (one or more pacing signals, at one or more sites in the heart 43) so as to alter overall heart function, as a stress test, a method for evaluating one or more regions of the heart, to evaluate a partial inter chamber block, or the like. In aspects, a simple pacing algorithm for lowering blood pressure may include direct A-V stimulation at a very low P-R interval (e.g., around 50 msec or so, etc.). Such an approach may also be applicable to covering early premature ventricular beats, or the like.

Such an approach may be advantageous to alter local sympathetic, peripheral sympathetic, MSNA, activity, or the like. Such pacing may be advantageous for testing the response of the sympathetic nervous system to heart stress, etc. In aspects, a first pacing electrode may be placed in the right atrium and a second pacing electrode in the left ventricle. Upon pacing, an altered operational characteristic of the heart may be established, thus changing blood pressure, systolic blood pressure, pressure waveforms, etc. Such changes may have a strong influence on afferent and thus efferent sympathetic outflow, be useful in determining the functional activity of one or more regions of the sympathetic nervous system, determine the ideal degree of ablation needed to treat a local site in the heart, etc.

In aspects, a reference electrode may be placed in the coronary sinus for sensing and electrocardiac mapping applications. Other locations for a reference may also be used and apparent to one skilled in the art upon reading this disclosure.

Other such methods for multi-chamber pacing of the heart which may be suitable for performing stress tests, altering heart function, or the like in accordance with the present disclosure herein include, but are not limited to those methods, approaches, and devices described in U.S. Pat. No. 8,428,729 titled "Cardiac Stimulation Apparatus and Method for the Control of Hypertension," United States Patent Application Publication No. 2005/0222640 titled "Heart Muscle Stimulator and Pacing Method for Treating Hypertension," and U.S. Pat. No. 8,086,315 titled "Cardiac Stimulation Apparatus and Method for the Control of Hypertension", the disclosures of which are incorporated herein by reference.

Figure 10A:
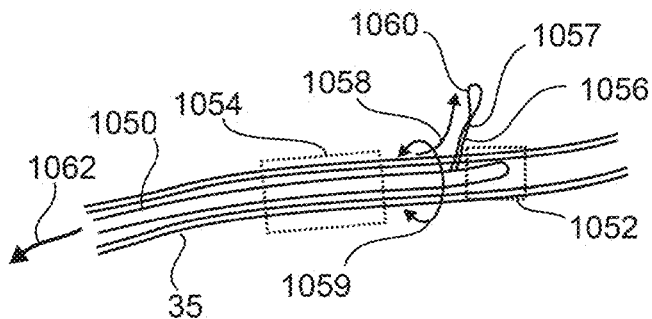
FIGS. 10A-10C illustrate aspects of delivery devices in accordance with the present disclosure.
Figure 10B:
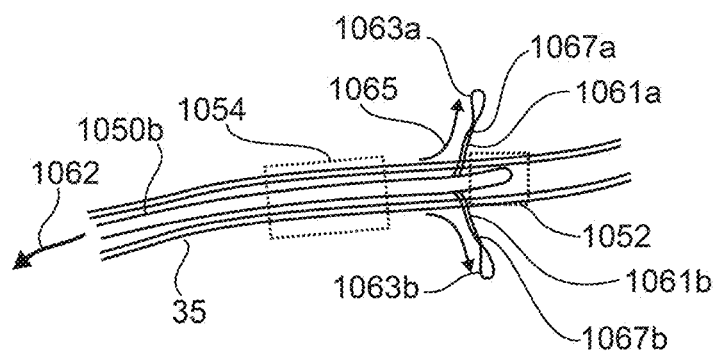
Figure 10C:
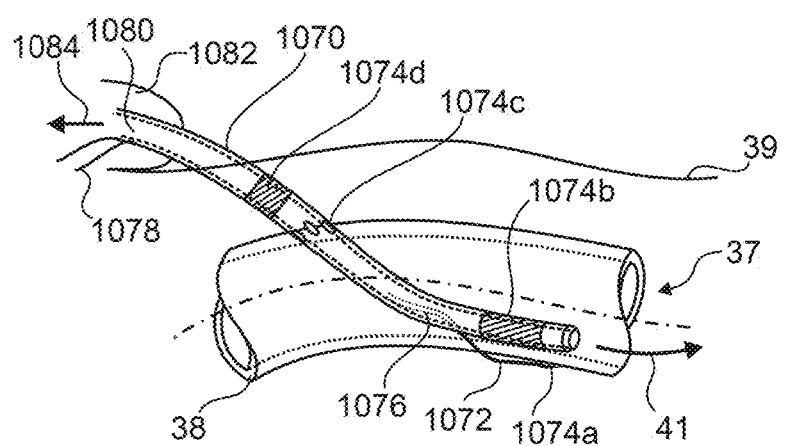

FIGS. 10A-10C illustrate aspects of delivery devices in accordance with the present disclosure. FIG. 10A illustrates aspects of a guidewire 1050 in accordance with the present disclosure placed within a lumen 35. The guidewire 1050 may be sized with sufficiently small tip diameter so as to reach a substantially small coronary vessel, with diameter of less than 2 mm, less than 1.5 mm, less than 1 mm, less than 0.75 mm, less than 0.5 mm, less than 0.35 mm, or the like. The guidewire 1050 may include one or more zones 1054, 1052 in accordance with the present disclosure. The guidewire 1050 includes a sensing zone 1054 located along the length thereof for interfacing with the lumen wall proximally to a treatment site. The guidewire 1050 includes a sensing tip 1052 located at the distal tip thereof for interfacing with the lumen distally to a treatment site. The guidewire 1050 includes one or more microneedles 1056, which may be advanced from the body of the guidewire 1050 into the wall of the lumen 35 into which it has been placed as part of a procedure. Such needle advancement or retraction 1058 may be coordinated by an operator, a controller 1062, etc. In aspects, the microneedles 1056 may provide a means for delivering a chemical agent 1060 into the tissues surrounding the lumen 35. In aspects, the microneedles 1056 may include one or more electrodes 1057 to monitor and/or interface (e.g., stimulate, ablate, etc.) the local tissues upon deployment therein. In aspects, the guidewire 1050 may be configured so as to deliver the microneedles 1056 into the adventitia of the lumen 35, or optionally directly into the parenchyma of an organ to be treated. Such a configuration may be advantageous to provide a substance, a composition, a neurotoxin, a cancer treating agent, a neuroblocking agent, a neurostimulating agent, etc. into the target tissues as part of a treatment procedure in accordance with the present disclosure.

In aspects, the guidewire 1050 may be torque-able 1059 so as to orient the microneedle 1056 with respect to a target site within the wall of the vessel 35, or a nearby target tissues site. Once oriented in the desired direction, the microneedle 1056 may be deployed into the target tissue. Such an arrangement may be advantageous to treat tissues in a wall of a chamber (such as the left atrium), from within an adjacent vessel (such as a coronary artery or vein), while minimizing tissue damage thereto and limiting damage to tissues between the access vessel and the target site.

In aspects, the guidewire 1050 may include a plurality of microneedles 1056 arranged along a length thereof, the microneedles 1056 arranged to one side such that upon deployment, a linear region along the length of the lumen 35 may be treated simultaneously. Such an arrangement may also be advantageous to form a controlled wall with substantially continuous treatment zone without causing excessive damage to surrounding tissues (such as for performing an atrial isolation from a coronary vessel access point).

In aspects, one or more of the microneedles 1056 may include a stop, such that the depth of the penetration of the needle tip into the surrounding tissues may be easily controlled.

FIG. 10B shows a guidewire 1050b with similar structure to guidewire 1050. The guidewire 1050b includes a plurality of microneedles 1061a,b arranged such that multiple boluses of a substance 1063a,b may be substantially simultaneously delivered to tissues in the vicinity of the lumen (i.e., in a circumferential pattern). In aspects, the microneedles may be deploy-ably 1065 pushed through the lumen wall to access one or more target sites, to form a thin ring of treatment around the lumen 35, etc. In aspects, the microneedles 1061a,b may be fashioned with one or more sensing tips 1067a,b in accordance with the present disclosure.

FIG. 10C shows aspects of a system for monitoring electrophysiological signals in the wall 38 of a lumen 37 in accordance with the present disclosure (e.g., such as within a coronary vessel wall, through a major vessel wall, or the like). In aspects, one or more probes 1072 in accordance with the present disclosure may be embedded into a sheath introducer. The sheath introducer may include a cannula 1070, along which electrical wiring 1078 and/or one or more of the probes 1072 may be arranged. The cannula 1070 may include one or more channels 1076 to accommodate one or more of the probes 1072, electrical wiring, or the like. The cannula 1070 may include one or more electrode bands 1074b,d and/or microelectrodes 1074c, configured for measurement within the wall 38 of the lumen 37, and/or for use as reference electrodes. The sheath introducer may include an embedded circuit and/or connector for interfacing with one or more of the electrodes 1074a-d, probes 1072, etc.

In aspects, one or more of the probes 1072 may include one or more electrodes 1074a in accordance with the present disclosure.

In aspects, one or more probes 1072 may be inserted into the lumen 37 of the subject, one or more of the probes 1072 may be inserted into the wall 38 of the lumen. In aspects, one or more of the probes 1072 may be anchored to the lumen wall 38, and/or one or more readings may be made from an electrode 1074a situated on the probe 1072 and/or on the cannula 1070 of the sheath introducer, to assist with placement, to read electrophysiological activity from the wall 38 of the lumen (i.e., to read activity within the smooth muscle of the media of the lumen wall), etc.

As part of a surgical procedure, the sheath introducer may be placed into the lumen 37 of a vessel through a skin 39 of a subject. The sheath introducer may provide a path for additional surgical tools to be introduced into the lumen 37 and progressed 41 there along to a target site (optionally remotely positioned from the entry point into the lumen). In aspects, one or more surgical tools (guidewires, catheters, balloon catheters, ablation catheters, etc.) may be introduced into the lumen 37 of the vessel via the sheath introducer.

In aspects, the sheath introducer may include a housing 1082 for placement against the skin 39 of the subject. The housing 1082 may include a valve coupling 1084 connected to the channel 1080 within the cannula 1070 of the sheath introducer, through which one or more tools may be advanced, removed, or exchanged during a surgical procedure. In aspects, the housing 1082 may include one or more connectors for interfacing electrically and/or mechanically with one or more of the electrical wiring 1088, electrodes 1074a-d, the probe 1072, or the like. In aspects, the connector may include an actuation mechanism (e.g., a sliding mechanism, a rotary mechanism, etc.), movement of which may be used to deploy the probe 1072 from within the channel 1076 into the lumen wall 38.

Such a configuration may be advantageous for use during a surgical procedure, to monitor electrophysiological activity from the vessel, for monitoring of smooth muscle activity before, during, and/or after the procedure, etc. Such a configuration may be advantageous for conveniently monitoring such activity while providing an access port for one or more of the surgical tools introduced during the procedure.

FIGS. 11A-11I illustrate aspects of sensing devices in accordance with the present disclosure. FIGS. 11A-11I show aspects of sensing tips, and/or zones associated with a sensing guidewire in accordance with the present disclosure. Generally speaking, the figures show non-limiting examples of sensing guidewires each including one or more sensors or electrodes located at the distal tip thereof. In aspects, the electrodes may be arranged in patterns around the circumference of the tip so as to contact a lumen wall if the guidewire is introduced deep enough into the lumen so as to bottom out (i.e., as the lumen diameter shrinks distally heading into the organ). The electrodes may be connected to a controller, a preamp (optionally embedded in the guidewire near the electrodes), a microcircuit (optionally embedded in the guidewire near the electrodes), a connector, or the like in accordance with the present disclosure. Such interconnection may be provided by one or more leadwires arranged along the length of the guidewire. In aspects, one or more of the leadwires may be integrated into the walls or jacket of the guidewire. In such configurations, the leadwires may be helically integrated, and/or braided into the walls or jacket, or equivalently threaded, coextruded, plated, shrink wrapped, or pultruded within the walls of the guidewire (i.e., or equivalently threaded through one or more microlumen within the wall of the guidewire).

The electrodes may be formed in accordance with the present disclosure. In aspects, the electrodes may be formed directly from the tips of the one or more leadwires. The tips of the leadwires may be formed into microelectrode elements, with predetermined exposed areas and tip profiles, suitable for monitoring electrophysiological activity at the site of interest. In aspects, the predetermined exposed areas may be designed so as to lean towards single unit recordings (e.g., electrode area less than 250 $\mu m^2$, less than 150 $\mu m^2$, less than 100 $\mu m^2$), multi-unit recordings (e.g., electrode area of greater than 500 $\mu m^2$, greater than 1000 $\mu m^2$, greater than 2000 $\mu m^2$), and large area or reference field recordings (e.g., electrode area greater than 10,000 $\mu m^2$, or the like). In aspects, the electrodes may be treated so as to alter the impedance thereof, during use. In aspects, the electrodes may be processed so as to increase the capacity thereof such as via conversion to, plating of, or augmentation with an electric energy storage (EES) material, an intercalating material, surface area increasing process, a plating process, combinations thereof, or the like. In aspects, each electrode may be configured with a profile suited for accessing the anatomy of interest (e.g., a needle-like structure, an embossed structure, a whisker like structure, a dendritic structure, etc.).

FIG. 11A shows aspects of a sensing tip of a guidewire 1126 in accordance with the present disclosure. The guidewire 1126 includes a microbasket electrode array 1128 including an array of micofingers 1129, each arranged in a bowed shape so as to extend out from the axis of the lumen into which the device is placed. Aspects of a single microfinger 1129 in the array is shown in the detailed view A. The microfinger 1129 includes one or more sensors or electrodes 1129a, each in accordance with the present disclosure. In the example shown in FIG. 11A, the electrode 1129a is shown patterned so as to face radially outwards from the center of the lumen into which the sensing tip is deployed (so as to embed and optionally isolate the electrode 1129a from the blood upon deployment). The electrode 1129a may be formed in accordance with the present disclosure. One or more regions of the microfinger 1129 may be isolated from the surroundings with an insulating layer (e.g., a passivated layer, a dielectric layer, a polymer, PTFE, parylene, etc.). In aspects, the microfinger 1129 may be configured so as to deploy to reach the shape shown in FIG. 11A during a predetermined procedure (e.g., actuation, sheath retraction, core extension, biodegradation of a restraint, etc.). In aspects, the microbasket array 1128 may be deployed during use so as to interface with the walls of a lumen, in accordance with the present disclosure. One or more microfingers 1129 and/or sensors or electrodes 1129a may be coupled with a connector or a controller 1127, preamp, microcircuit, circuit, a connector, or the like each in accordance with the present disclosure.

FIG. 11B shows aspects of flexible multi-electrode guidewire tips 1121, 1101 in accordance with the present disclosure. FIG. 11B shows monolithic guidewire tips 1101 including one or more tines 1103, each tine including one or more sensors and/or microelectrodes 1105 each in accordance with the present disclosure configured for interfacing with an anatomical site of interest within a body. The guidewire tip 1101 may be at least partially formed or coupled to a flexible substrate in accordance with the present disclosure configured and dimensioned to interface with the tines 1103 as well as provide electrical interconnection of components placed there upon, or integrated into the substrate.

In aspects, the substrate may include a flexible polymer, polyimide, PET, PEN, an elastic material, a silicone, an elastomer, an electroactive polymer, or the like known in the field of flexible electronics.

In aspects, the guidewire tip 1101 may include one or more microcircuits in accordance with the present disclosure. The microcircuits may be configured to perform one or more functions such as signal routing, multiplexing, demultiplexing, preamplification, signal amplification, filtering processes, differential coupling to a reference electrode, signal conditioning function, analog to digital conversion, communication, power management, combinations thereof, and the like. The substrate may include one or more conducting traces placed so as to interconnect the sensors and/or electrodes with the microcircuits. In aspects, the microcircuit may have a width of less than 2 mm, less than 1.5 mm, less than 1.1 mm, less than 1 mm, less than 0.75 mm, less than 0.5 mm, less than 0.36 mm, or the like. In aspects, a plurality of microcircuits may be embedded into the guidewire tip 1101 so as to interface with a large number of electrodes 1105, etc.

In aspects, the substrate may include one or more of the conducting traces, the conducting traces may include a metal, a meandering metal trace (i.e., so as to improve the flexibility or stretch capability thereof), an organic conductor, a printed structure, a physically deposited structure, or the like.

In aspects, one or more microelectrodes 1105 may be formed at the extreme tip of a tine 1103. Such formation may be achieved by routing one or more traces to the tip and severing the tip so as to expose only the most distal part of the trace so as to form the interconnect for the microelectrode 1105. The interconnect may be plated with an interfacing material, such as a metal, platinum, a composite, a conjugated polymer, etc. so as to form the microelectrode 1105 and so as to enhance coupled between the microelectrode 1105 and a surrounding anatomical site of interest.

The substrate may include interconnects for coupling with power and signal lead wires. The microcircuit may be configured to communicate with an outside communication module, a controller, or the like (not explicitly shown). In aspects, communication may be in the form of a bus protocol such as I²C, 1-wire, SPI, serial, etc. In aspects, the lead wires may be configured and interconnected to power management hardware configured so as to provide power and signal communication along the same leads. Such a configuration may be advantageous to minimize the number of lead wires within the guidewire.

After attachment of components (e.g., sensors, microcircuit(s), lead wires, etc.) the substrate may be rolled to form a completed guidewire tip. A non-limiting example includes a guidewire tip with an integrated jacket coupled to the tip so as to reinforce the electrical interconnection of the substrate, the lead wires, and/or the microcircuits. In aspects, the jacket may also provide increased electrical isolation between the microcircuits, the traces, the lead wire interconnects, and the surroundings.

FIG. 11B illustrates a non-limiting example of a guidewire tip 1121 with deployable tines 1103. The tines 1103 may be deployed from within a jacket 1123 by retraction 1127 of the jacket 1123, advancement 1125 of the tines 1103 or a combination thereof. Such action will lead to deployment 1115 of the tines 1103 so as to monitor a physiologic parameter during a procedure in accordance with the present disclosure.

Two non-limiting examples of deployed configurations are shown in FIG. 11B, a configuration where the tips of the tines 1103 are free and the set shape of the tines 1103 results in a flower like formation upon deployment from the jacket 1123. In aspects, the interconnects 1131 on the substrate 1107 may be dimensioned and/or encapsulated so as to form a soft seal against the jacket 1123. Such a configuration may be advantageous to minimize fluid ingress to the guidewire during a procedure.

In aspects, the lead wires 1131 may be coupled with a controller 1130 in accordance with the present disclosure.

Another example of a deployed configuration is shown in FIG. 11B, a configuration where the tips of the tines 1103 are held together with a restraining tip 1135 so as to form a basket shape upon deployment 1125. The basket may be retained in a jacket 1139 of the device before deployment 1125. In aspects, the restraining tip 1135 may include an additional pull wire 1132 configured such that relative movement of the pull wire may provide the forces necessary to deploy 1125 the tines 1103 (i.e., to convert the tines 1103 from a collapsed shape to a basket-like shape).

In aspects, one or more of the tines 1103 may be coupled with a microcircuit 1137 in accordance with the present disclosure. The microcircuit 1137 may be embedded into the device substantially near to the tines 1103, within 400 mm thereof, 100 mm thereof, within 20 mm thereof, within 5 mm thereof, etc.

FIG. 11C shows a guidewire 1140 in accordance with the present disclosure. The guidewire 1140 includes a tip for interfacing with target tissues in a vessel, the tip including a cage 1143, the cage including a plurality of electrodes 1144 coupled to an embedded microcircuit 1147 in accordance with the present disclosure via substrate 1145. The guidewire 1140 includes abridge 1148 coupled with the microcircuit 1147 and a controller 1150, so as to provide proximal communication between the microcircuit 1147 and external hardware of the controller 1150 during use. The guidewire 1140 also includes an optional thin flexibility adjusting sheath 1149 configured so as to adjust the stiffness of the bridge 1148 (e.g., so as to adjust the push ability of the tip, allow for deployment of a spiral based ablation catheter over the bridge 1148 during use, etc.). The guidewire 1140 further includes a guide tip 1141 coupled with the cage 1143 via a guide ring 1142, the guide ring 1142 optionally connected or slidingly coupled to the guide tip 1141 so as to allow for diameter adjustment of the cage 1143 during use. Such an arrangement may be advantageous for engaging the electrodes 1144 of the guidewire with the walls of a small vessel, threading the cage 1143 through a tortuous vessel, or the like. In aspects, such a catheter may be suitable for accessing a coronary vessel, coronary artery, coronary vein, artery, vein, or the like in a subject in accordance with the present disclosure. The deployed cage 1143 diameter may be generally in the range of 0.5-8 mm, particularly 0.5-2 mm, including 0.5-1.5 mm, or the like.

FIGS. 11D-11F illustrate a non-limiting example of a guidewire 1160 in accordance with the present disclosure illustrating floating cage 1163 embodiment. The floating cage 1163 includes one or more sensory elements, sensors, electrodes, etc. in accordance with the present disclosure. The floating cage 1163 is coupled with a guide ring 1162 and an electronics housing 1165 which are both configured so as to slidingly engage with a guide tip 1161. The guide tip 1161 is fastened to one or more stops 1166a,b, which define a range 1173, 1174 over which the floating cage 1163 may travel during pull back 1172 or push forward 1175 operations of the bridge 1169. In this non-limiting example, the guidewire 1160 includes a coupling 1171 arranged so as to physically and electrically attach the bridge 1169 to an embedded microelectronic circuit 1167 via flexible interconnect 1168. The arrangement may be advantageous to minimize wall stress against the deployed floating cage 1163 during movement along an associated vessel wall. Such an arrangement is suitable for ensuring that the cage 1163 is always in an self-reducing arrangement during such movements (i.e., so as to limit wall stresses during advancement 1175 or withdrawal 1172 of the cage during use). FIG. 11E shows the guidewire 1160 during pullback 1172, and FIG. 11F shows the guidewire 1160 during advancement 1175 along a lumen axis.

FIGS. 11G-11I illustrate a non-limiting example of a guidewire 1180 in accordance with the present disclosure illustrating floating cage 1183 embodiment. The floating cage 1183 includes one or more sensory elements, sensors, electrodes, etc. in accordance with the present disclosure. The floating cage 1183 is coupled with two guide rings 1182 and 1191 both configured so as to slidingly engage with a guide tip 1181. One of the rings is arranged so as to be electrically coupled to one or more sensing elements in the cage 1183 with an associated electronics housing 1185 via a flexible interconnect 1188, the electronics housing 1185 coupled with the guide tip 1181 and associated bridge 1189 so as to communicate with an externally located controller. The arrangement allows for the cage 1183 to float along the guide tip 1181 during pull back 1192 or push forward 1195 operations of the bridge 1189. During such movements, the limits of the cage 1183 movement are generally determined by the size and positioning of the electronics housing 1185. In this non-limiting example, the electronics housing 1185 is arranged so as to physically and electrically attach the bridge 1189 to an embedded microelectronic circuit 1187 embedded there within. The arrangement may be advantageous to minimize wall stress against the deployed floating cage 1183 during movement along an associated vessel wall. Such an arrangement is suitable for ensuring that the cage 1183 is always in a self-reducing arrangement during such movements (i.e., so as to limit wall stresses during advancement 1195 or withdrawal 1192 of the cage during use). FIG. 11H shows the guidewire 1180 during pullback 1192, the cage 1183 movement limited 1193 during the maneuver, and FIG. 11I shows the guidewire 1180 during advancement 1195, the cage 1183 movement limited 1194 during the maneuver, along a lumen axis.

The structures shown in FIGS. 11A-11I may be used for in vessel and through vessel sensing, for chemical delivery, etc. in some embodiments. The structures shown in FIGS. 11A-11I may be used, for example, in neural sensing along arteries, coronary arteries, veins, coronary veins, etc.

Figure 12A:
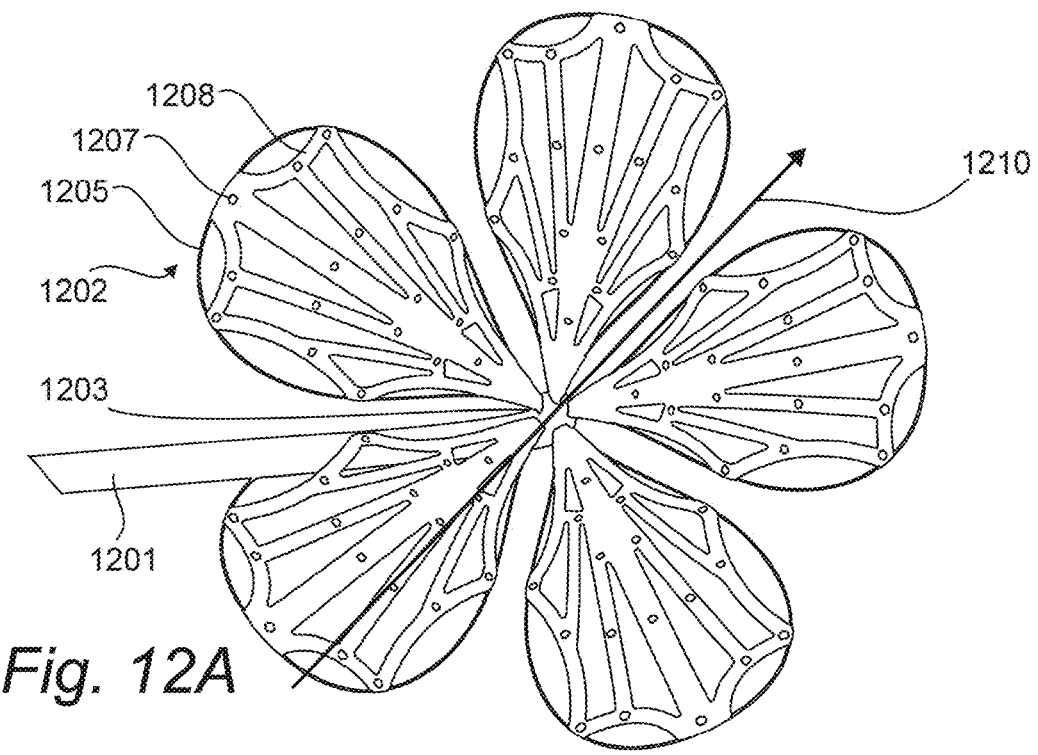
FIGS. 12A and 12B illustrate aspects of sensing devices in accordance with the present disclosure.
Figure 12B:
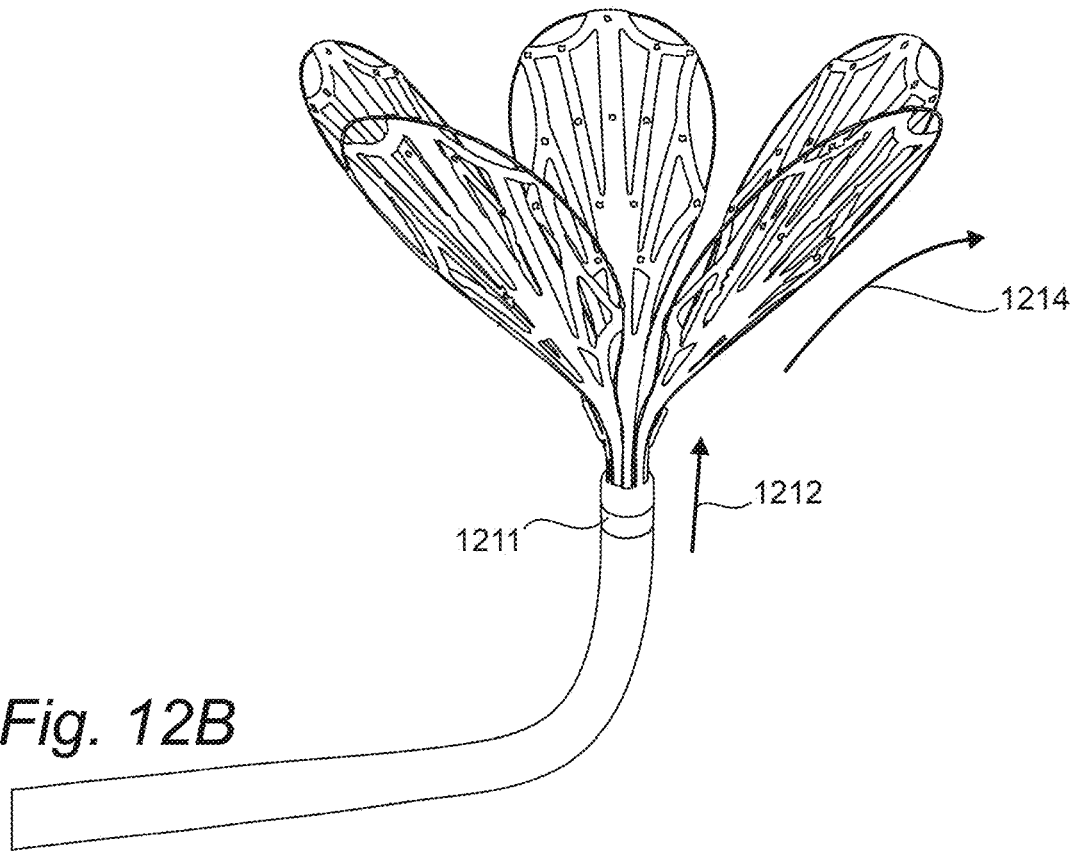

FIGS. 12A and 12B illustrate aspects of sensing devices in accordance with the present disclosure. FIG. 12A shows a view of a pedal based sensing device 1201 with the pedals 1202 deployed (such as against the wall of a large vessel, against a chamber wall of a heart, etc.). Each pedal 1202 is configured so as to softly and confidently bias against the wall of a target region upon deployment from a body 1203 of the catheter 1201. The pedals 1202 may be arranged so as to bias one or more sensing elements, electrodes 1207, or the like against the lumen wall during deployment 1214. As shown, each pedal 1202 includes a framing band 1205 (in this non-limiting example formed from a flexible wire element), and a substrate 1208 webbed around the framing band 1205 so as to form a surface upon which a plurality of sensors 1207 are arranged. In aspects, the substrate 1208 may be formed from a flexible material, a polymer, a liquid crystal polymer, a non-woven, a mesh, a woven wire arrangement, etc. In aspects, the substrate 1208 is formed from a non-woven, the electrodes 1207 connected with a proximally embedded microcircuit in accordance with the present disclosure, via micro wires embedded in the substrate 1208 (not explicitly shown for clarity). In aspects, each pedal 1202 may include a microcircuit coupled with the corresponding substrate 1208. Thus the catheter 1201 may include a plurality of microcircuits so as to manage a large number of sensing elements, electrodes 1207, etc. In this non-limiting example, each pedal is equipped with 17 electrodes 1207, thus the 5 pedals 1202 include 85 electrodes 1207 to generate an ultra high density spatially distributed sensing region defined by the boundary 1210 of the deployed pedals 1202. In aspects, the boundary 1210 diameter may be adjusted by altering the deployment depth 1212 of the pedals 1202, altering the length of the pedals 1202, etc. In aspects, the number of electrodes per petal may be considerably higher than shown in the Figure. In aspects, one or more of the electrodes in each petal may be configured as reference electrodes.

By embedding the microcircuits locally to the recording site, a seemingly limitless number of electrodes may be incorporated into the catheter tip. In one non-limiting example, each petal or equivalent electrode supporting structure may include tens to hundreds of electrodes (i.e., greater than 10 electrodes, greater than 15 electrodes, greater than 63 electrodes, greater 127 electrodes, etc.), so as to obtain exquisite spatial acuity during mapping, sensory recording, characterization of a rotor, of a neural or cardiac ablation target, mapping of changes in electrical activity during an ablation event, etc.

FIG. 12B illustrates how the pedals 1202 may be flexibly biased 1214 against a lumen wall during deployment 1212. Thus the electrodes 1207 may be controllably maintained against the lumen wall during use, thus improving the quality of the recordings derived therefrom, reducing movement noise artifacts, etc. FIG. 12B also shows a markerband 1211, which may be used to assist with positioning of the catheter in the subject. In aspects, the markerband 1211 may double as a reference electrode for one or more electrodes coupled to the catheter.

In some embodiments, the pedals 1202 shown in FIGS. 12A and 12B are used to interface with walls or other end-on surfaces such as the ventricles and atria of a heart from within the chamber, or on the outside of the heart.

Figure 13A:
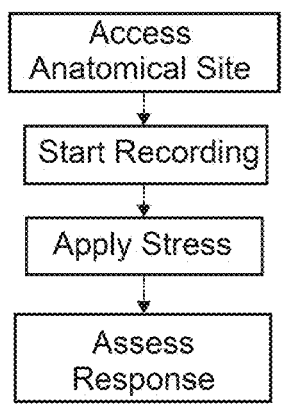
FIGS. 13A-13C illustrate methods for sensing neural traffic and treating tissues in accordance with the present disclosure.
Figure 13B:
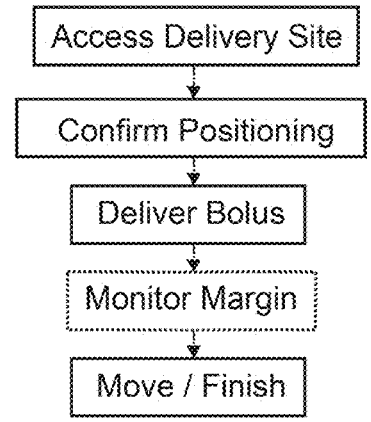
Figure 13C:
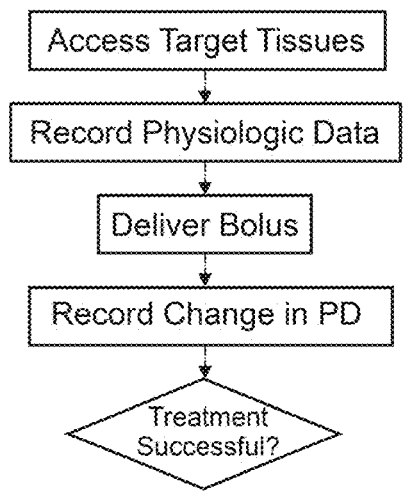

FIGS. 13A-13C shows aspects of methods in accordance with the present disclosure. FIGS. 13A-13C shows aspects of methods for using a delivery system in accordance with the present disclosure. The method of FIG. 13A includes accessing an anatomical site, starting recording of signals, applying a stress and assessing the response. The method of FIG. 13B includes accessing a delivery site, confirming positioning, delivering a bolus, monitoring margin, and moving the delivery system or finishing the method. The method of FIG. 13C includes accessing target tissues, recording physiologic data (PD), delivering a bolus, recording changes in PD and determining if a treatment is successful. Although the methods of FIGS. 13A-13C include aspects for assessing response, monitoring margin, confirming treatment, etc. they may be applied to treatment scenarios without substantial feedback steps.

The method of FIG. 13B includes accessing a delivery site within a body, such as the parenchyma of an organ, a site along or through a vessel wall, or the like. By accessing the delivery site is meant coupling a tip or region of a delivery tool in accordance with the present disclosure with one or more anatomical sites within the body, so as to provide fluid communication between a reservoir and the anatomical sites for which treatment is desired. Such access may include delivery of a tool tip to a desired treatment site, deployment of one or more delivery needles towards the desired treatment site, to penetrate the wall of a lumen to access the treatment site, etc.

The method of FIG. 13B may optionally include confirming placement near the anatomical site, such as by recording physiologic activity from tissues in the vicinity thereof (e.g., with a sensor or electrode, a guidewire, a delivery tool, etc. each in accordance with the present disclosure), and monitoring a trend in the physiologic signal (e.g., during a stimulation event, during a stress test, etc.), making a diagnosis or prognosis based upon the recorded signal (e.g., a diagnosis of a disease state associated with local physiologic activity in the tissues, making a prognosis relating to an outcome of a disease state associated with activity in the tissues or tissues associated therewith, etc.), via direct imaging of the tissues with an imaging system in accordance with the present disclosure, etc. The method of FIG. 13B may include delivering a bolus of a composition in accordance with the present disclosure to the tissues, in the form of a pattern, etc. The method of FIG. 13B may include optionally monitoring the margin of a tissue target near the delivery site, and/or monitor the migration of the composition or a component thereof upon delivery to the tissues. The method of FIG. 13B may include moving the delivery tool, retracting a delivery needle, or otherwise finishing the treatment by decoupling the delivery tool from the treatment site.

In aspects, the method may include one or more additional steps in accordance with the present disclosure. In aspects, the method may include placing an additional tool including one or more sensors and/or electrodes at a remote location (with respect to the organ) in the body and stimulating the local anatomy at either the remote site or within the parenchyma of the organ and monitoring an evoked response within the target tissues or at the remote site respectively. Such a configuration may be advantageous for elucidating information about the connectivity between the two sites (i.e., relevant to determining if a neuromodulation procedure applied there between has been successful, etc.).

FIG. 13C illustrates an additional method including accessing the target tissues (alternatively an anatomical site of interest, a vessel, an artery, a vein, an arteriole, a venule, etc.), and recording and/or mapping the electrophysiological activity in the vicinity of the anatomical site of interest. The mapping may be provided by sweeping a sensory tip in accordance with the present disclosure over the anatomical site of interest, inserting and then withdrawing the sensory tip, deploying the sensory tip and then dragging and/or rotating the deployed tip along/around the lumen wall, combinations thereof, and the like. In aspects, the method may include displaying the mapped physiologic information for a user, constructing an anatomical model therefrom, directing a surgical robot to perform a treatment therefrom, comparing the map with a previously determined map (e.g., as a means for monitoring the outcome of a procedure, tracking a therapy, etc.), combinations thereof, or the like. In aspects, the method may include providing one or more directions to a surgeon and/or a surgical robot to access one or more regions of the mapped anatomy, overlaying the present map with previously generated maps (so as to evaluate changes in functionality, activity, etc.), combinations thereof, and the like.

The method of FIG. 13C may include delivering a bolus of a composition in accordance with the present disclosure to the target tissues, and optionally assessing an anatomical site of interest within the vicinity of the target tissues or coupled thereto, stimulating one or more physiologic systems in the body, and/or monitoring the evoked response at the anatomical site of interest to determine the effect of the bolus on the target tissues. The method of FIG. 13C may include recording a change in PD. The method of FIG. 13C may include assessing the functionality of the anatomical site of interest, the site of stimulation (i.e., if the stimulation is of a localized type), the target tissues, or an anatomical site there between. The method of FIG. 13C may include assessing if the treatment was successful, such as via recording a marked change in neural traffic from affected tissues, a change in the proportion of neural response to a stress test, etc.

In aspects, the method may include ablating one or more anatomical sites within the body.

In aspects, one or more methods in accordance with the present disclosure may be completed, at least in part, with a delivery tool in accordance with the present disclosure.

Additional method targets include: ganglion sites; measuring/evaluating EP and innervation along PV and target sites such as complex fractionated atrial electrograms (CFAE); methods for each procedure; ganglion access; recordings for ganglia localization; methods for each of the therapies; mapping of atria, ventricles, etc.; internal and external approaches; smooth muscle innervation in arteries; sensing directed treatments thereof such as ablation or growth factors dependent on recordings; assessing valves and valve innervation; biventricular stimulation methods as a stress test; single beat chamber mapping through combinations of extreme electrode count and chamber filling electrode arrays; etc.

Figure 14A:
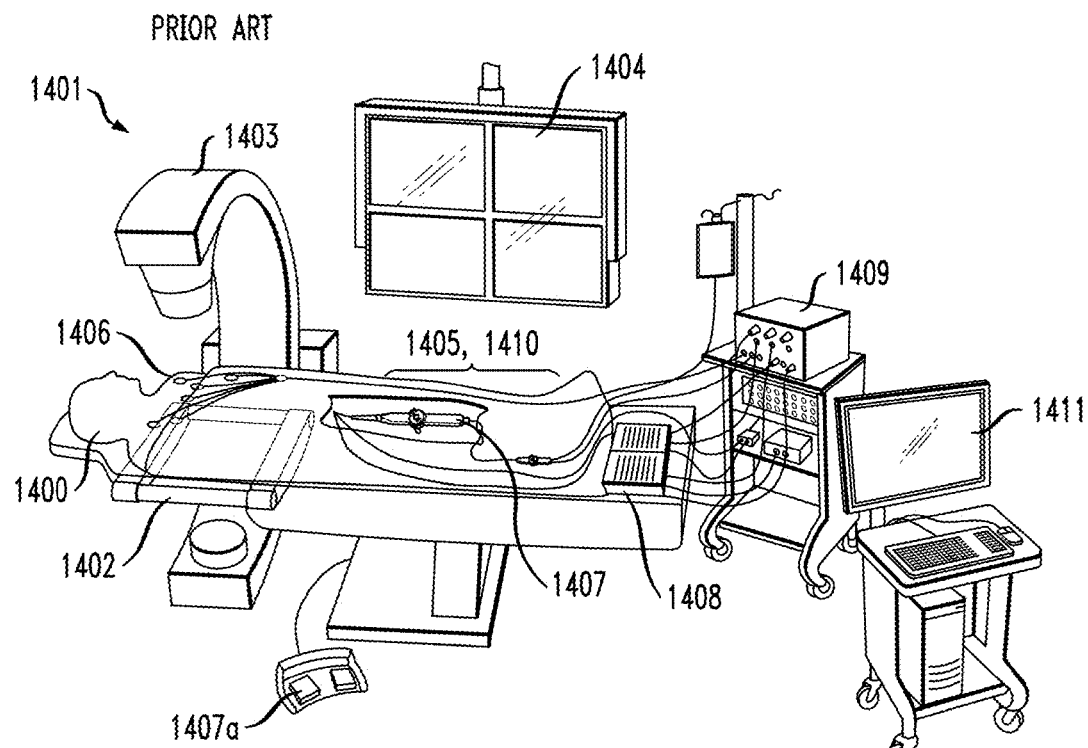
FIGS. 14A and 14B illustrate and compare a prior art system and a mapping system in accordance with the present disclosure.
Figure 14B:
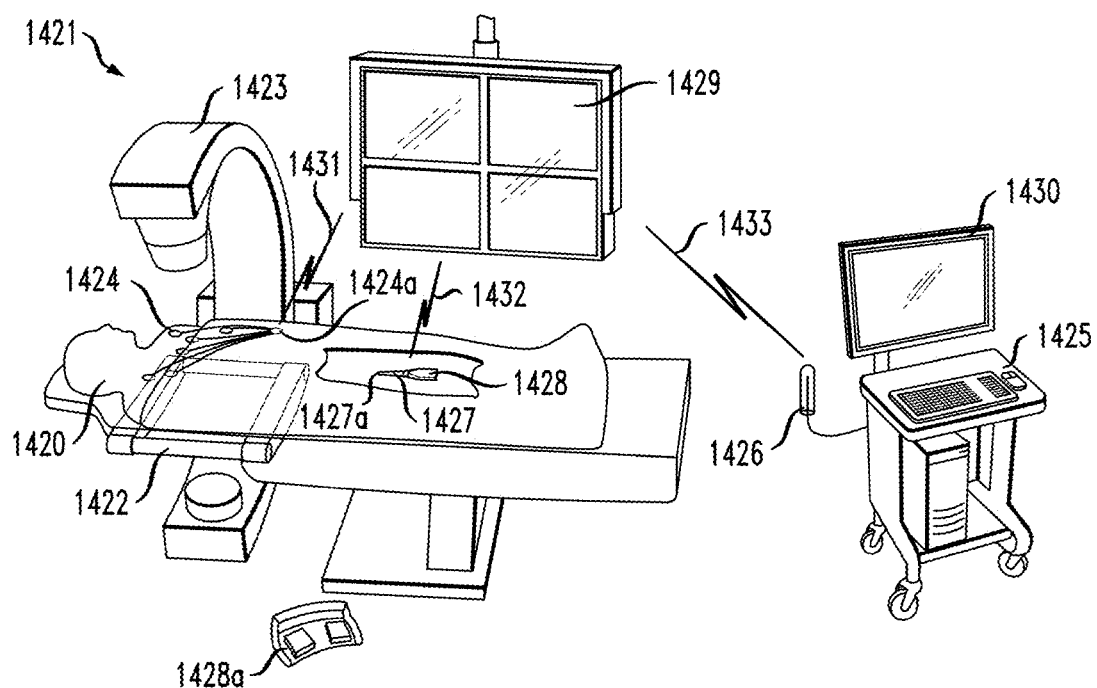

FIGS. 14A and 14B illustrate and compare a prior art system and a mapping system in accordance with the present disclosure. FIG. 14A illustrates a prior art mapping system (Rhythmia monitoring System™) showing a subject 1400 in an interventional suite 1401 and a bed 1402, the suite including an imaging system 1403 and one or more displays 1404. The subject 1400 is coupled to a mapping catheter 1405, and a 12 lead surface ECG lead set 1406, the mapping catheter 1405 coupled with a control handle 1407, the control handle 1407 and lead set 1406 coupled to a connector array 1408 and a signal flow controller 1409. As shown, the control handle 1407 is a wand shape with a dial thereon. Also shown are control pedals 1407a, which may be used for separate functions from the control handle 1407. For example, the control pedals 1407a may be used to start/stop recording, to start/stop ablation of stimulation with a mating catheter, etc. A stimulation catheter 1410 is also shown. As shown, the stimulation catheter 1407 is inside the subject 1400. The signal flow controller 1409 is coupled to a control console 1411 and the display 1404.

FIG. 14B illustrates a mapping and stimulation system in accordance with the present disclosure. A subject 1420 is shown in an interventional suite 1421, on a bed 1422 and an imaging system 1423. The subject 1420 is coupled to a wireless 12 lead surface ECG lead array 1424, the lead array 1424 wirelessly coupled 1431 to a control console 1425 (via wireless communication with an antenna 1426). The lead array 1424 includes optional wireless hardware 1424a to facilitate the wireless communication 1431. Also shown is a mapping catheter 1427 in accordance with the present disclosure coupled to the 1420 subject through a guide sheath, the mapping catheter 1427 coupled with a wireless, battery operated control handle 1428, the control handle 1428 wirelessly coupled 1432 with the control console 1425 (via wireless communication with antenna 1426). The control console 1425 may be coupled with a display 1429, console display 1430, etc. The wireless, battery operated control handle 1428, may include one or more signal conditioning circuits, math processing units, or the like to condition signals obtained from the mapping catheter 1427 before sending the signals and/or associated metrics along to the control console 1425. Also shown are control pedals 1428a, which may be used for separate functions from the control handle 1428. For example, the control pedals 1428a may be used to start/stop recording, to start/stop ablation of stimulation with a mating catheter, etc. The control pedals 1428a may be wirelessly connected to the control handle 1428 or other elements shown in FIG. 14B. The display 1429 and control console 1425 may also be configured for wireless communication 1433 as shown.

The control handle 1428, also referred to herein as a smart torquer, may be small in size such as about the size of an index finger. Thus, the size of the control handle 1428 shown in FIG. 14B is not to scale—the control handle 1428 may be much smaller than depicted relative to the size of subject 1420. FIG. 14B and other figures are not necessarily drawn to scale for clarity of illustration.

In aspects, the mapping catheter 1427 may include one or more integrated circuits, microelectronic circuits, or the like to amplify, and/or convert the measured neural and/or cardiac signals into a useable form. Signals obtained from the surface ECG 1424 may be used for timing the measured signals, or the like. In aspects, the mapping catheter 1427 may include one or more stimulating lines or electrodes, configured so as to stimulate one or more sites in the target tissue, the stimulating electrodes purposefully arranged in the electrode array, or coopted from one or more sensing electrodes in the array. As shown, the mapping catheter 1427 enters subject 1420 through the catheter entry site 1427a at the tip of the mapping catheter 1427.

In aspects, such an arrangement may be advantageous to collect tens, to hundreds, to thousands of simultaneous recordings at sites within the subject 1420 while maintaining a sufficiently small and maneuverable catheter body, a low wire count within the catheter body, or the like. In aspects, the integrated circuits may be coupled with tens to thousands of sensors in an associated sensing array, and with power and one or more digital communication and signal management lines located within the catheter body. In aspects, the catheter body includes 4-20 wires, 3-12 wires, 1-8 wires, or the like, to communicate signals from the integrated circuits to the control handle. Such a configuration may be advantageous to greatly simplify the manufacturing, improve signal conditioning, allow for ultra-miniature electrodes, greatly increase electrode count, and the like associated with the mapping process.

Such a system may be advantageous to perform single beat mapping of cardiac chambers, vessels, and the like during an electrophysiologic mapping procedure, ablation procedure, diagnostic test, therapeutic procedure, etc.

The system shown in FIG. 14B can provide a number of advantages relative to the system shown in FIG. 14A. For example, the system shown in FIG. 14B can be wireless and battery operated, as communication between the catheter 1427 and control console 1425 is wireless and digital. In contrast, the system shown in FIG. 14A utilizes large electrode blocks and amplifier racks as shown in connector array 1408. By going battery operated and wireless, the FIG. 14B system can reduce electromagnetic interference (EMI) for electrodes of the catheter 1427 dramatically, thereby improving performance. In addition, cabling coming off the subject 1420 to connector blocks and amplifier racks can be minimized or eliminated completely. This is of practical importance in real-world settings, as the system of FIG. 14B can limit the amount of equipment bridging a sterile zone of the procedural arena. This provides not only safety advantages, but also cost reduction in reducing the amount of cumbersome and expensive equipment needed such as the connector array 1408 shown in the system of FIG. 14A.

Figure 15A:
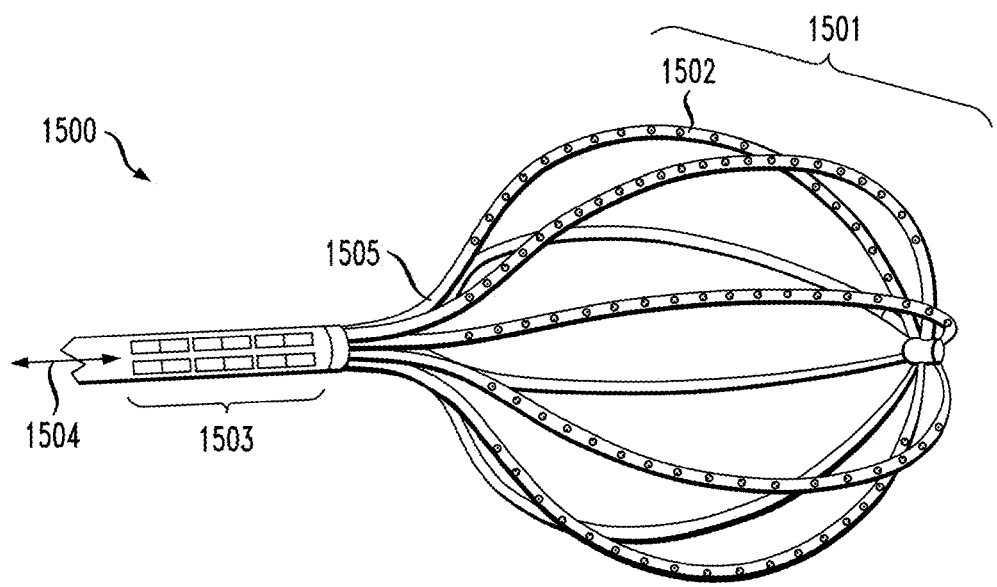
FIGS. 15A-15E illustrate aspects of chamber mapping catheters in accordance with the present disclosure.

FIGS. 15A-15E illustrate aspects of chamber mapping catheters in accordance with the present disclosure. FIG. 15A shows aspects of a basket catheter 1500 including an array 1501 of sensing elements 1502 each in accordance with the present disclosure. The sensing elements 1502 may include electrodes, radiopaque markers, etc. The basket catheter 1500 may include dozens of sensing elements, hundreds of sensing elements, thousands of sensing elements, or the like. The sensing elements 1502 are electrically coupled with one or more embedded microcircuits 1503 each in accordance with the present disclosure placed near to the array. The microcircuits 1503 are coupled with a proximal connector, proximal hardware, or the like. The microcircuits 1503 may also include or be coupled with optional passives such as matching components, bypass caps, etc. The body of the catheter 1500 may include one or more wires, a flexible circuit (i.e., the same flexible circuit as the electrode array, etc.), so as to communicate 1504 between one or more of the embedded microcircuits 1503 and an external control handle, or the like. The communication 1504 may include power and digital communications. The communication 1504 may only need a few wires to communicate electrogram data to an external recorder. Due to the very small wire count needed to support a very large electrode count, the diameter of the wire body can be extremely small.

In aspects, a plurality of microcircuits 1503 are coupled together so as to form a digital network topology, a star network topology, a ring network topology, a bidirectional network topology, or the like in order to communicate between microcircuits 1503, and/or external hardware. In aspects, each of the microcircuits 1503 may be coupled to a subset of the sensing elements 1502, so as to coordinate signal acquisition of electrophysiologic and/or physiologic signals in the vicinity thereof.

Such a configuration may be advantageous for non-contact inter chamber and/or lumen mapping of cardiac and/or neural activity in the vicinity of each sensing element 1502 in the array 1501. If suitably shaped, such a configuration may be suitably deployed in a cardiac chamber, a body lumen, a bladder, an atrium, or the like, so as to map neural activity, cardiac muscle activity, and/or local field potentials at a plurality of sites within the subject overtime. Such mapping may be suitable for determining ablation targets, identifying aberrant traffic from a local ganglion, assess the quality or continuity of a block, and assess changes in electrical activity caused by therapy, a temporary stimulus, a temporary neural block, or the like.

One or more struts 1505 of the cage array may include reinforcement, stiffening elements, or the like in order to assist with maintenance of shape during deployment, maintenance of wall contact during deployment, or the like. In aspects, all the electrical interconnects between the embedded circuits, the proximal connector, the control handle, and/or one or more of the sensing elements 1502 may be made via a monolithic interconnect, a flex interconnect, or the like. Such a configuration may be advantageous for complete or near complete single beat inter chamber mapping of electrical activity of cardiac tissue, during diagnostics, therapies, or the like.

Similar to FIG. 14B discussed above, FIG. 15A is not necessarily drawn to scale. For example, each of the struts 1505, also referred to herein as tines, may have a width in the range of 0.1 mm or less than the width of a human hair. In applications, the width of each strut 1505 may be uniform or variable over the length, and may range from 0.025-2 mm, including 0.05-0.25 mm, and in particular including 0.075-0.125 mm, or the like. The sensing elements 1502 or electrodes formed on the struts 1505 may be even smaller such that, were they drawn to scale, they would not generally be visible in FIG. 15B. FIGS. 15D and 15E, for example, show structures where the sensing elements such as sensing elements 1502 are not visible. The sensing elements 1502 or electrodes are oriented on the struts 1505 so as to be biased against walls of target tissues for recording upon deployment and are thus isolated from the surrounding chamber lumen. This provides significant advantages relative to conventional techniques.

Having a recording front end (e.g., microcircuits 1503) within a few inches of the sensing elements 1502 allows for the use of large numbers of electrodes or sensing elements 1502 placed as desired on the struts 1505 with size and material combinations as desired. Such an arrangement also provides significant advantages relative to conventional techniques, as the spatial density, bandwidth and acceptable input impedance of sources which can be recorded are expanded due to the ability to select the size, numbering, spacing, materials, etc. of the electrodes or sensing elements 1502. For example, hundreds or thousands of electrodes can be practically implemented in a clinical setting for analyzing cardiac and neural signals in the heart and elsewhere. This allows for numerous advantages, such as in mapping rotors with high definition, simultaneously analyzing neural and cardiac traffic in adjacent tissues, precisely determining margins of ischemic tissue, locating the source of an arrhythmia, analyzing the effect of a therapeutic agent on the adjacent tissues, monitoring the effect of stimulation, ablation, or the like on adjacent tissues, as well as other benefits described herein. In addition, the approach allows for unusually soft and compliant struts 1505 to be implemented such that broad and intimate contact between the electrodes and adjacent tissues may be achieved during use, in effect, the device may be constructed soft enough to conform to the target tissues in the body, rather than the devices being sufficiently stiff such that the devices force the tissues to conform to the device profile. Such an approach may be advantageous as it will allow for monitoring the tissues in their natural state, without providing substantial biasing forces or stretch to the tissues, which can alter the electrophysiology and excitability thereof.

By combining the local microelectrodes or sensing elements 1502 and leads with local amplification and conversion through embedded microcircuits 1503, a number of benefits are provided. Conventional approaches, for example, may require a 1:1:1 relationship between electrodes, wires/leads and connectors. The basket catheter 1500 shown in FIG. 15A, however, can use miniaturized microcircuits 1503, such as custom ASIC circuits, each with a 1×2×0.1 mm die size including micro-bumped interconnects to maintain chip level attachment, each to handle 16 channels of electrodes on the front end. Each of the microcircuits 1503 allow for digitally communicating data from the 16 electrodes into a 3 or 4 wire network on the back end (e.g., the wires that run through the catheter body). Such chips can be daisy-chained to scale up the number of electrodes or sensing elements 1502 without having to increase the number of wires on the back end. Thus, hundreds or thousands of electrodes or sensing elements 1502 can be simultaneously monitored with only a comparatively few number of wires communicating the data from the basket catheter 1500. For example, a 3-4 wire bus may be used to support 128 electrodes in some embodiments.

Further, the spatial density of the electrode or sensing element 1502 positioning that can be achieved is not limited by having 1.5 m or longer wires or leads attached to each electrode as required by conventional techniques. A large number of electrodes or sensing elements 1502 can be patterned onto a single flex, to which the chips or microcircuits 1503 are attached, and hundreds or thousands of leads are conveniently completed between the microcircuits 1503 and the electrodes 1502 without an assembler having to manually connect electrode rings to proximal connectors or thread wire assemblies through a catheter body. Such approaches also allow for extremely high density mapping, preferential placement of electrodes or sensing elements 1502 at any desired location on the struts 1505 so as to achieve intimate contact with tissues when the basket catheter 1500 is deployed. Although shown as struts 1505, the approach allows for preferential shaping of the supporting structure(s) as well, which allows for the electrodes to be placed onto any shaped structure so as to optimally mate those electrodes against the target tissues during use.

The advantages in scaling the number of electrodes or sensing elements 1502 using microcircuits 1503 described with respect to basket catheter 1500 may also be realized using other electrodes and sensing elements described with respect to other ones of the figures, including by way of example the structures shown in FIGS. 15B-15E.

Figure 15B:
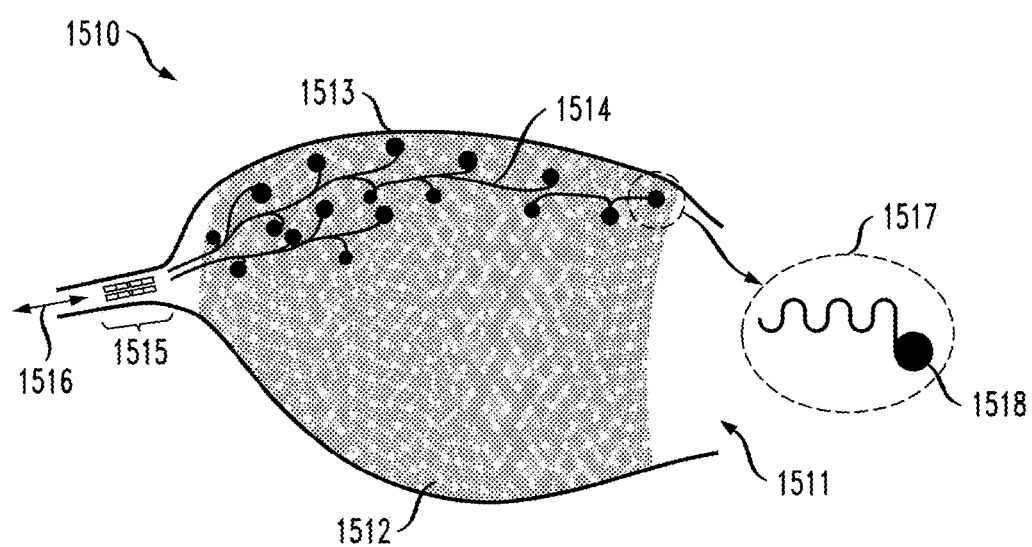

FIG. 15B illustrates a mesh like flexible structure/scaffolding catheter 1510, which may conformably expand upon deployment within a lumen or chamber in the subject. The flexible structure/scaffolding 1511 may be sufficiently porous and/or sparsely arranged with structural elements 1512 so as to allow for substantially unrestricted blood flow there through upon deployment. The scaffolding 1511 may be coupled to one or more sensing elements 1513 each in accordance with the present disclosure. The sensing elements 1513 may be arranged along a meandering flexible substrate 1514, so as to allow for substantially unrestricted deployment of the scaffolding 1511 within the lumen/chamber. The flexible substrate 1514 including one or more interconnects to couple each sensing element 1513 to one or more inputs/outputs of an associated embedded microcircuit 1515. In aspects, the catheter 1510 may include one or more embedded microcircuits 1514, coupled to the flexible substrates 1514 near to the scaffold 1511, such that the lead impedance variation, movement associated lead noise, and the like are minimized during use. Also shown is digital and power communications 1516, which may be similar to communications 1504 described above. Further, FIG. 15B shows a close up view 1517 of the flexible substrates 1514 illustrating an example of the meandering trace coupling to an electrode 1518, which is an example of one of the sensing elements 1513.

In aspects, the mapping catheter 1510 may include one or more embedded microcircuits 1515 each in accordance with the present disclosure each coupled to one or more sensing elements 1513 in the array.

The soft expanding scaffold 1511 may be advantageous for filling a space such as a cardiac chamber, so as to perform a substantially whole chamber single beat cardiac mapping, or the like. The scaffold 1511 may thus provide a deployable support structure that takes the shape of the chamber into which it is deployed.

In aspects, the soft, expandable scaffold 1511 may be formed from a non-woven, a shaped scrim, a braided wire basket assembly, or the like. In aspects, the scaffold 1511 may be formed from a braided polymeric fiber array, so as to form a sufficiently soft yet elastic shell upon which the meandering interconnects or substrates 1514 may be arranged. Such a soft and elastic shell may be repeated over the surface of the scaffold 1511 such that the scaffold 1511 is ultra flexible and can move with the chamber walls during monitoring. In aspects, the interconnects 1514 may be formed from elastic conductive materials, or the like so as to form a sufficiently resilient and flexible structure upon which to interconnect the sensing elements 1513 with the microcircuits 1515, or the like. Such an open network may be advantageous to allow for substantially unrestricted blood flow through the scaffold 1511 during use, etc.

Figure 15C:
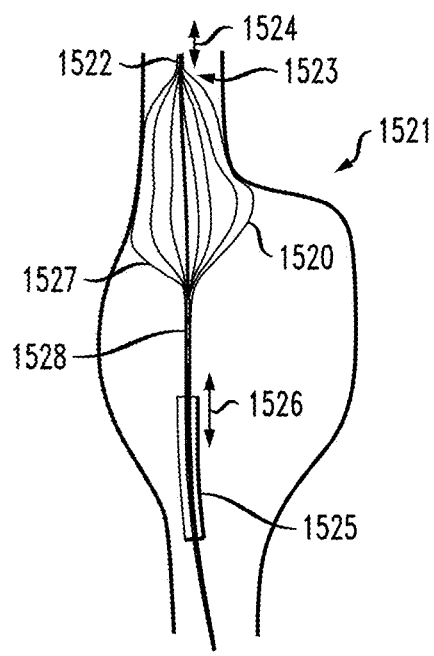
Figure 15D:
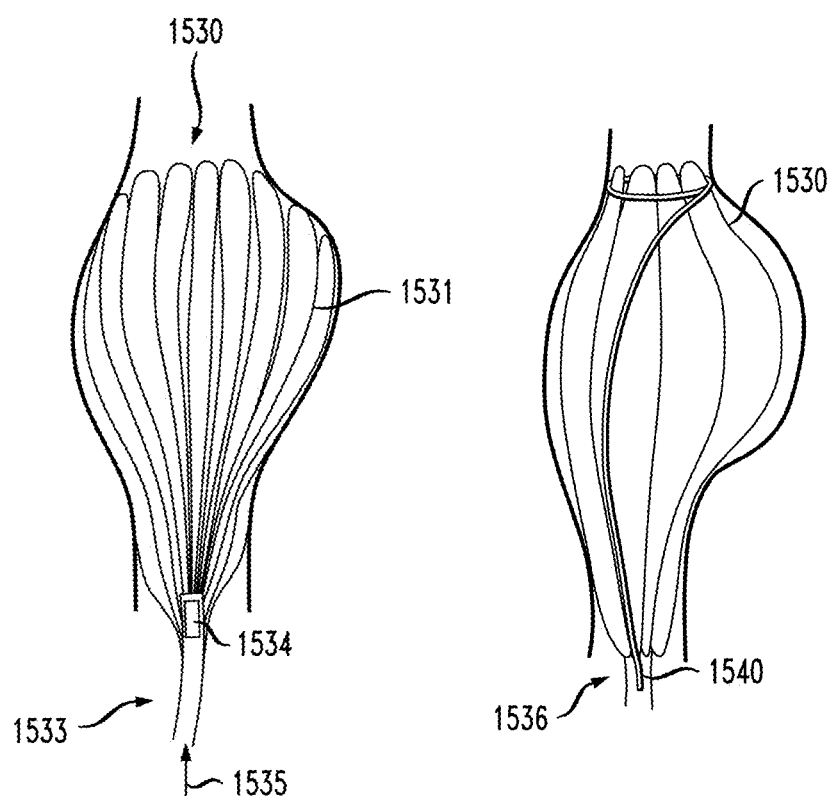
Figure 15E:
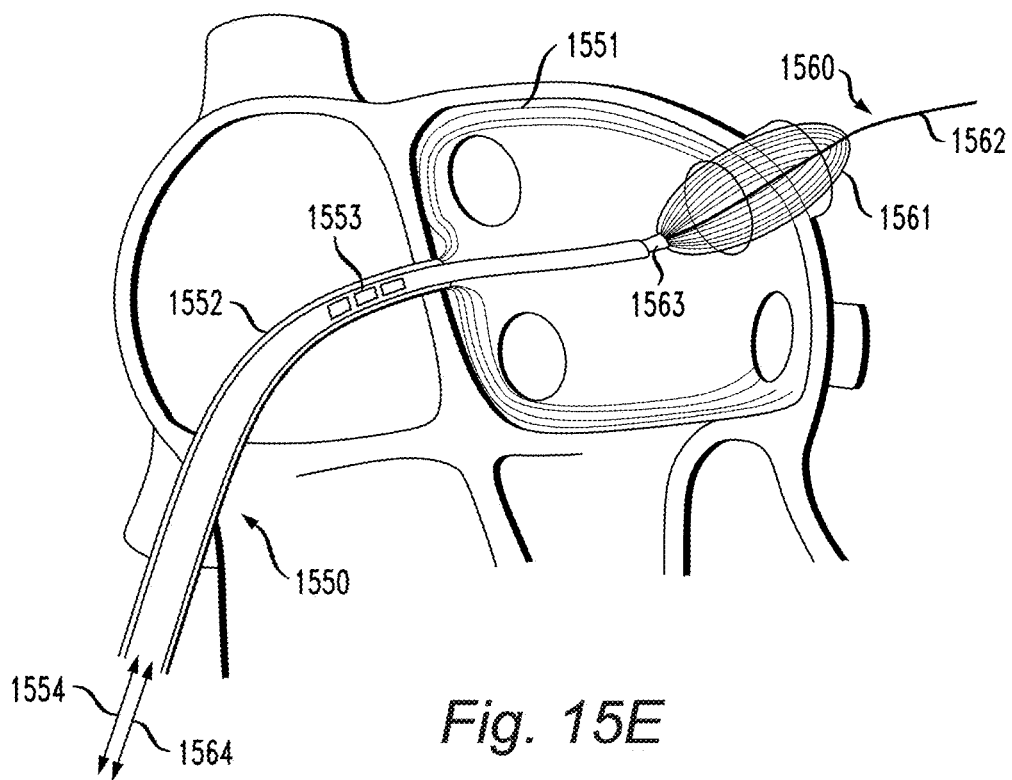

FIG. 15C illustrates aspects of a basket-like sensing element array 1520 placed into the lumen of a vessel 1521 (superior vena cava). Two alternative deployment methods are shown, a first method is achieved by inclusion of an axially extendable member 1522 fixed to the distal tip 1523 of the basket 1520 which may be retracted or pushed in order to affect the radial deployment 1524 of the basket 1520, and an alternative approach achieved by inclusion of a retractable sheath 1525, the sheath 1525 being of sufficiently large diameter such that the basket 1520 can be collapsed into the sheath 1525 prior to delivery, the sheath 1525 being withdrawing so as to deploy 1526 the basket 1520 around a target site, such as a vessel in the body. As shown, the basket struts 1527 are sufficiently flexible so as to gently bias against the lumen wall (in the case that the deployment diameter is larger than the vessel diameter), upon deployment. In aspects, the struts 1527 are made so as to be sufficiently flexible such that, upon deployment, an oversized strut will bias against the vessel wall with a local pressure of less than 30 mmHg, less than 20 mmHg, less than 10 mmHg, or the like. Such low pressure deployment may be advantageous to substantially prevent compression block of nearby tissues during monitoring from the walls of the vessel. Also shown are embedded microelectronics or microcircuits 1528.

FIG. 15D shows aspects of a deployable sock-like basket 1530 including a plurality (e.g., 10s, 100s, 1000s, etc.) of sensing elements 1531 each in accordance with the present disclosure. The sock-like basket 1530 has been deployed so as to interface with one or more regions of the right atrium of a heart. The sock-like basket 1530 is coupled with one or more embedded microelectronic elements 1532, arranged nearby so as to allow for short interconnect length, few wires or interconnects along the body of the catheter, etc. As shown, the basket 1430 is deployed through a channel 1534 of a mapping catheter 1533, configured for digital communication 1535 with an external controller (not shown).

FIG. 15D also shows a cut-away view of the right atrium, illustrating the deployed sock-like basket 1530 along with a lasso-shaped ablation/stimulation catheter 1540, deployed through a lumen 1536 in the mapping catheter 1533 so as to access one or more sites within the chamber without interrupting the monitoring from the sensing elements 1531 in the basket 1530. Such an arrangement may be advantageous for performing substantially whole chamber, beat-by-beat mapping of electrophysiologic data from a range of sites along the walls of the atrium.

In aspects, the density and/or arrangement of the sensing elements 1531 may be strategically provided over the basket 1530, cage, or the like so as to concentrate readings in the vicinity of key areas along the chamber surface, such as near problematic ganglia, etc. such as those shown in FIGS. 1-4.

FIG. 15E shows aspects of a two component mapping catheter 1550 in accordance with the present disclosure, the first mapping catheter including a substantially large, chamber filling basket 1551, the basket 1551 including a plurality of sensing elements, as sufficiently soft and spring-like so as to conform to one or more walls of the left atrium during deployment, the structure of the basket 1551 sufficiently open so as to minimally affect blood-flow there through during use. The chamber filling basket 1551 including an opening in the distal end, through which a second mapping catheter 1560, including a lumen-sized basket 1561 is shown, the second mapping catheter 1561 having been deployed through a lumen 1552 of the first mapping catheter 1550. The second mapping catheter 1560 may include a guidewire 1562. Each catheter 1550, 1560 may include one or more microelectronic elements 1553,1563, embedded near to the sensing sites, so as to minimize noise, catheter size, wiring complexity, or the like. Signals from sensing elements 1551,1561 in both catheters 1550,1560 may be obtained simultaneously during use so as to substantially perform whole chamber single beat localization of neural and/or cardiac signal traffic during use. The catheters 1550, 1560 are configured for digital communication 1554,1564 with an external controller. All local readings from the catheters 1550,1560 may be synchronously read at a recorder or external controller via digital communication 1554,1564. The microelectronic elements 1553,1563 may provide for high fidelity sensing, stimulation, ablation, or the like. Because local sensing is performed electrode sizes of the sensing elements 1551,1561 can be miniaturized such that both electrograms from cardiac tissue and local autonomic traffic may be monitored. A large number of sensing elements 1551,1561 (e.g., thousands) may be placed and assessed using catheters 1550,1560 while requiring only a few digital lines to provide digital communication 1554, 1564 of data outside the body to an external controller.

Such an approach may be advantageous for locating target sites for ablation, verifying treatment, verifying temporary blocks, or the like.

FIG. 16 shows application of a composition, delivery system, and delivery tools 1600*a,b* each in accordance with the present disclosure to treatment of a carotid body 71 (i.e., a target site near to an access lumen such as a ganglion, a tumor, a sensory body, a node, a lymph node, etc.). The delivery tools 1600*a,b* includes one or more needle-like delivery tips 1605*a,b* in accordance with the present disclosure, each delivery tip 1605*a,b* may be tipped with a sensor and/or electrode 1610*a,b* each in accordance with the present disclosure. The delivery tips 1605*a,b* may include a lumen to fluidly couple the distal tip of the delivery tools 1600a,b to the proximal end thereof. The lumen may be coupled with one or more ports in accordance with the present disclosure so as to deliver a composition to the carotid body 71 or a site coupled thereto. The delivery tips 1605a,b may be advanced 1620a,b into the tissues around the carotid bifurcation so as to couple one or more of the sensors and/or electrodes 1610a,b with the carotid body 71 or one or more sites thereabout thus forming one or more target tissues, monitoring sites or treatment sites 73a-d within or around the carotid body 71. The delivery tools 1600a,b may include a jacket to alter the stiffness of one or more segments of the delivery tools 1600a,b, to protect the delivery tips 1605a,b, one of the sensors 1610a,b, etc. In aspects, the delivery tools 1600a,b may include one or more stabilizing members, an anchor, a hook, a balloon, or the like, configured so as to stabilize and/or orient one or more regions of delivery tools 1600a,b near to the intended treatment site. Once stabilized, the delivery tips 1605a,b may be advanced 1620a,b towards the carotid body 71 or an associated treatment site 73a-d. In aspects, the delivery tools 1600a,b or associated delivery tips 1605a,b may include one or more radiopaque markers, or may be constructed with one or more radiopaque materials in order to assist a surgeon with visualization of the surgical site during the procedure. In aspects, the stabilizing members may be configured to limit relative motion between the delivery tips 1605a,b (e.g., the needles, the electrodes 1610a,b, etc.) and the carotid body 71, vessel walls 75, 77, 79, associated treatment/monitoring sites 73a-d, etc. during one or more procedures performed thereon.

In aspects, the delivery tools 1600a,b may be used to monitor one or more sites 73a-d within and around the carotid body 71 to assist in selectively ablating only a region of the carotid body (e.g., an outer layer, a surface, a chemoreceptor, a baroreceptor, etc.). In aspects, the delivery tools 1600a,b may be used to both sense and selectively ablate and/or deliver a composition to regions of the carotid body 71 or a site 73a-d there about. In such procedures, the sensing may be performed with or without stimulation/stress to determine the ideal locations within the carotid body 71 to perform a neuromodulation, chemical denervation, ablation, delivery of a neural agonist, neural antagonist, etc. Upon determining the ideal locations, an RF current, a microbolus of neurotoxin, etc. may be injected into key sites amongst the monitoring/treatment sites 73a-d. Such a procedure may be advantageous for neuromodulating the carotid body 71 while limiting damage to surrounding structures, or to regions of the carotid body 71 that are to be spared in the procedure.

As shown in FIG. 16, the neural body 71 (such as, in this non-limiting example, a carotid body) may be located in the vicinity of a main carotid artery 75, an internal carotid artery 77, or an external carotid artery 79. The delivery tools 1600a,b may be configured for placement in a lumen 75, 77, 79 in the vicinity of the neural body 71 (i.e., in this case a carotid body), neurons coupled thereto (in the vicinity of regions 73a-d), and/or receptors (i.e., in this case baroreceptors lining wall of the internal carotid artery 77). In aspects, one or more elements of the delivery tools 1600a,b may be configured so as to be actuate-ably advanced 1620a,b into the wall of the lumen 75, 77, 79, or into contact therewith so as to be advanced towards a target tissue 73a-d (e.g., one or more regions of the neural body 71, a region adjacent to the neural body 73c,d, nerves and/or nerve plexuses 73a,b coupled to the neural body 71, and/or regions including receptors in the vicinity of the neural body 71 and/or the walls of the adjacent lumens 75, 77, 79, etc.).

In aspects, one or more of the electrodes 1610a,b may be configured to stimulate, and/or treat one or more regions of the carotid body 71, and/or one or more target tissues 73a-d as part of a surgical procedure. Additionally, alternatively, or in combination the delivery system may be configured to deliver a stressing agent (e.g., a hormone, a neurotransmitter, nitric oxide, oxygen, carbon dioxide, etc.) directly into the carotid body 71 to assess a change in the neural traffic assessed in the body 71 or within the vicinity of one or more of the target tissues 73a-d, assess a change in a body response to the stimulus (e.g., a change in heart rate, respiration, heart rate variability, blood pressure, sPO2, sympathetic outflow, mSNA changes, etc.). The region of treatment as well as the extent of treatment may be monitored and/or controlled by a circuit coupled with one or more electrodes on one or more of the delivery tips 1605a,b.

In aspects, one or more electrodes 1610a,b and/or delivery tips 1605a,b may be configured to monitor, to stimulate, and/or to alter (e.g., deaden or block neural traffic, ablate the nerves, etc.), neurological activity in one or more nerve bundles extending from the neural body 71. Changes in neural traffic after a surgical procedure, in response to a stimulus, or the like may be used to assist in controllably treating one or more regions of target tissue 73c-d in or near the neural body 71, or other target tissues 73a-b in the vicinity thereof.

In aspects, an RF current may be applied through one or more of the electrodes 1610a,b in order to treat the carotid body 71 or a target site 73a-d. The current may be passed between one or more of the electrodes 1610a,b and a remotely located electrode (not explicitly shown) or between two or more of the electrodes 2610a,b. Such a method may be advantageous for selectively controlling the current flow to the regions of the carotid body 71 in need of treatment. In aspects, the remotely located electrode may be a gel electrode placed upon the skin of the body (not explicitly shown), a needle electrode, an electrode placed within a nearby vein, or the like.

In aspects, a composition in accordance with the present disclosure may be injected into the carotid body 71. The composition may be formulated such that the ablation zone around the carotid body 71 is less than 5 mm outside the margin of the carotid body, less than 3 mm, less than 2 mm, less than 1 mm. Such adjustments may be made by altering the percentage of one or more excipients in the composition, adding a diluting agent (e.g., saline, water, etc.) to the composition, etc. In general, the composition may include a contrast agent in accordance with the present disclosure so as to visualize the migration of the composition after injection into the carotid body 71, or one or more treatment sites 73a-d coupled thereto.

In aspects, a method for treating such tissues may include injecting a first bolus of a first composition into or near to the carotid body 71, the first composition having an ablation and/or migration characteristic to treat at least a portion of the carotid body 71. The method including injecting one or more additional boluses of a second composition, the second composition having an ablation and/or migration characteristic suitable for treating another region of the carotid body 71, migrating outwards from the carotid body 71, etc.

In aspects, a method for treating a carotid body 71 may include accessing the arteriole vasculature of the carotid body and injecting a composition in accordance with the present disclosure into the vasculature, so as to fill the carotid body 71 with the composition. After injection, the composition will temporarily occlude blood flow within the carotid body 71 while the ablative component thereof diffuses into the tissues of the organ and completes ablation thereof (e.g., so as to ablate all receptors in the organ, to ablate particular receptor types in the organ, to ablate chemical receptors, to ablate baroreceptors, etc.). Such a method may be advantageous to safely treat the carotid body with minimal collateral damage to surrounding tissues. As the composition may quickly breakdown in the general blood flow, the risks to the subject are minimized, with ablation being very controllably delivered only to the tissues in the carotid body 71 that are intimately served by the vasculature thereof. The delivery tools 1600*a,b* may be coupled with one or more controllers 1615*a,b* respectively to manage needle deployment/retraction 1620*a,b*, coupling of the delivery tips 1605*a,b* or one or more sensors 1610*a,b* with external electronics, a polygraph, or the like.

FIGS. 17A and 17B show aspects of a delivery system in accordance with the present disclosure for treating tissues along a vessel. FIG. 17A shows aspects of a delivery tool 1700 for use in a delivery system in accordance with the present disclosure. The delivery tool 700 includes a jacket 1705 including a plurality of ports 1710 through which a plurality of delivery tips 1715*a,b* in accordance with the present disclosure may pass through in order to couple with a local anatomical site of interest, to stabilize the delivery tip, etc. The delivery tips 1715*a,b* may include one or more electrodes 1720 and/or sensors at the tip thereof in order to interface with the local anatomical site of interest (e.g., to measure local electrophysiological activity, to determine placement of the tip, to determine if the tip has exited the lumen, etc.). In aspects, the delivery tips 1715*a,b* may include an insulating layer 1725 configured so as to isolated one or more aspects of the delivery tip 1715*b* from the surroundings. In aspects, the insulating layer 1725 may include a varying thickness, optionally arranged so as to form one or more step transitions along the length of the delivery tip 1715*b*. Such steps may be advantageous for limiting the depth of penetration of the delivery tip 1715*b* into the local tissues.

In aspects, the delivery tips 1715*a,b* may include a lumen through which to deliver 1730 a composition 1735, a chemical substance, a medicament, etc. to the site of interest. The delivery tips 1715*a,b* may include one or more ports, shaped elements, etc. in accordance with the present disclosure to treat a region of tissues, interact with an adjacent volume of tissue in a particular pattern, etc. In aspects, the delivery tips 1715*a,b* may be deployed 1740 from the delivery tool 1700 so as to interact with an adjacent volume of tissue.

In aspects, the delivery tips 1715*a,b* and/or anchors may be slidingly coupled with the jacket 1705 such that they may be advanced 1740 as part of a deployment procedure. In aspects, the delivery tips 1715*a,b* and/or stabilizing elements may be coupled with a connector, actuator, and/or a controller 1745 generally situated at the proximal end of the delivery tool 1700.

FIG. 17B illustrates aspects of a delivery tool 1750 in accordance with the present disclosure placed within a lumen 74. The delivery tool 1750 may include one or more zones 1755*a,b* in accordance with the present disclosure. The delivery tool 1750 includes a first sensing zone 1755*a* located along the length thereof for interfacing with the lumen 74 wall proximally to a treatment site. The delivery tool 1750 includes a second sensing zone 1755*b* located at the distal tip thereof for interfacing with the lumen 74 distally to a treatment site. The delivery tool 1750 includes one or more microneedle delivery tips 1760, which may be advanced from the body of the delivery tool 1750 and into the wall of the lumen 74 into which it has been placed as part of a procedure. Such needle advancement or retraction 17765 may be coordinated by an operator, a controller 1770, etc. In aspects, the microneedle delivery tips 1760 may provide a means for delivering a composition, a chemical agent 1775 into the tissues surrounding the lumen 74. In aspects, the microneedle delivery tips 1760 may include one or more electrodes 1780 to monitor and/or interface (e.g., stimulate, ablate, etc.) with the local tissues upon deployment therein, to monitor (e.g., via impedance changes, via changes in local electrophysiological signals, etc.) a margin of migration or treatment of a bolus delivered to the tissues. In aspects, the delivery tool 1750 may be configured so as to deliver the microneedle tips 1760 into the adventitia of the lumen 74, or optionally directly into the parenchyma of an organ to be treated. Such a configuration may be advantageous to provide a composition in accordance with the present disclosure, a neurotoxin, a cancer treating agent, a neuroblocking agent, a neurostimulating agent, etc. into the target tissues as part of a treatment procedure in accordance with the present disclosure.

Figure 18A:
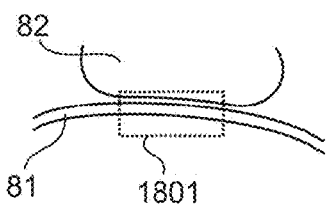
FIGS. 18A-18N show aspects of a delivery system and method for treating tissues in a thin walled structure.
Figure 18B:
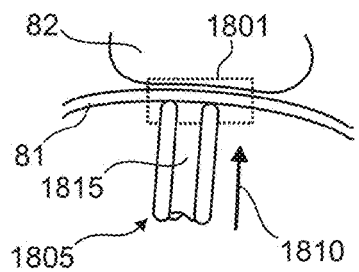
Figure 18C:
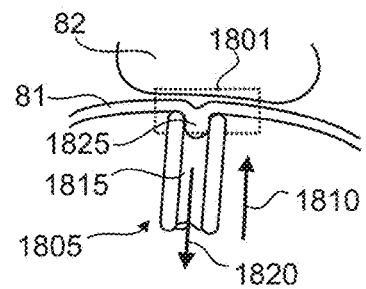
Figure 18D:
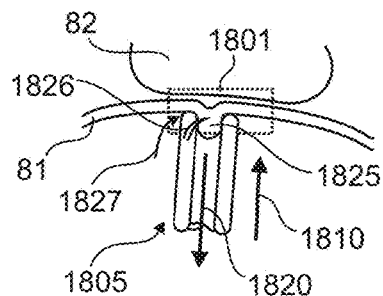
Figure 18E:
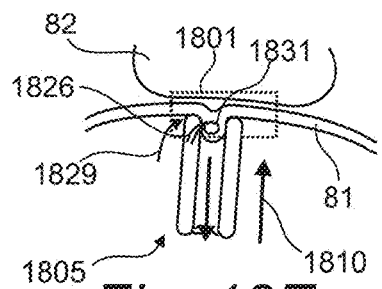
Figure 18F:
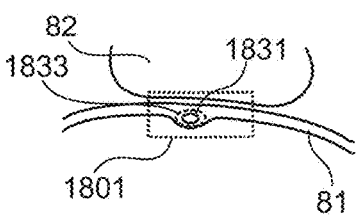
Figure 18G:
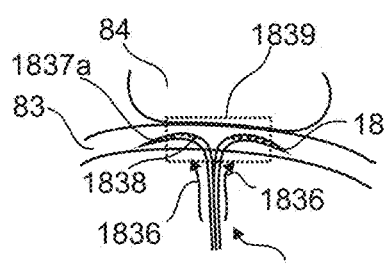
Figure 18H:
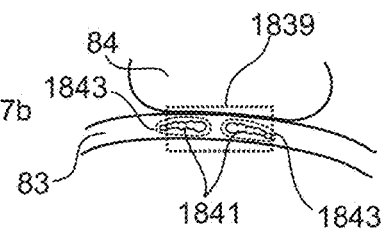
Figure 18I:
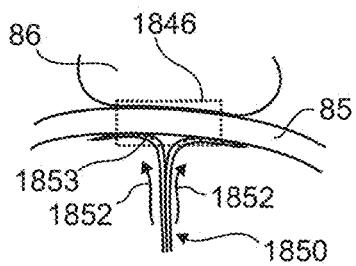
Figure 18J:
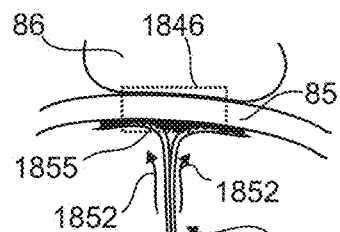
Figure 18L:
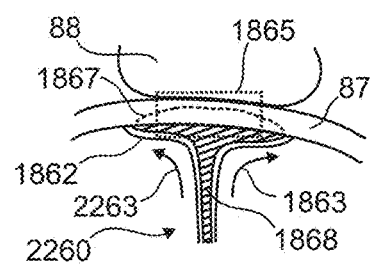
Figure 18M:
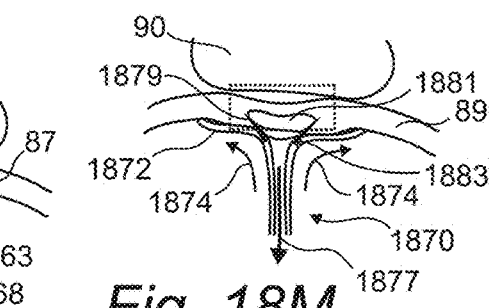
Figure 18K:
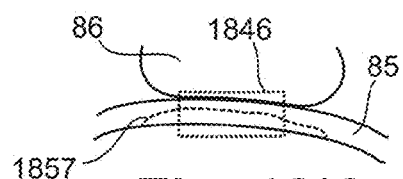
Figure 18N:

FIGS. 18A-18N show aspects of a delivery system and method for treating tissues in a thin walled structure. FIG. 18A shows a thin walled section 81 (e.g., a wall of an atrium, a bowel wall, a bladder wall, an esophagus wall, a membrane, a vaginal wall, a pericardial sac, etc.) and an adjacent structure 82 that is not to be treated (e.g., an esophagus beside an atrial wall, a prostate next to a bladder, a gall bladder next to a duodenum, etc.). The desired treatment zone 1801 is shown substantially within the thin walled section 81.

FIG. 18B illustrates aspects of a delivery tool 1805 in accordance with the present disclosure, the delivery tool 1805 biased 1810 against the thin walled section 81 so as to seal a lumen 1815 against the wall and the tip of the delivery tool 1805.

FIG. 18C illustrates application of a vacuum, or suction 1820 to the lumen 1815 of the delivery tool 1805 to draw a section of tissue 1825 into the lumen 1815. Such an approach may be advantageous to confidently capture and retain the tissue segment for subsequent treatment thereof. In aspects, the tip of the delivery tool 1805 may include a plurality of electrodes (not explicitly shown), for passing an RF current therethrough the section of tissue 1825, so as to safely treat it without affecting the adjacent structure 82.

FIG. 18D illustrates the delivery tool 1805, having drawn a section of tissue 1825 into the lumen 1815 thereof, the delivery tool 1805 driving, engaging, or otherwise penetrating 1827 a microneedle delivery tip 1826 in accordance with the present disclosure into the section of tissue 1825, so as to engage therewith.

FIG. 18E illustrates delivery 1829 of a bolus 1831 of a composition in accordance with the present disclosure into the section of tissue 1825, the composition retained within the section of tissue 1825 for treatment thereof.

In aspects, the tip of the delivery tool 1805 may include one or more electrodes in accordance with the present disclosure to assess the electrophysiological properties of the tissues, to assess the effect of the bolus on the tissues, etc.

FIG. 18F illustrates the thin walled section 81 after removal of the delivery tool 1805, the bolus 1831 embedded therein, one or more active components of the bolus 1831 diffusing into the tissues to form a treatment zone 1833. The adjacent structure 82 is substantially untreated, unpenetrated, etc. Such an approach may be advantageous for precisely treating thin walls without penetrating them, without affecting adjacent structures 82, etc.

FIG. 18G shows a delivery tool 1835 in accordance with the present disclosure including two delivery tips 1837a,b having been advanced 1836 into a thin walled section 83 without penetrating there through or into an adjacent structure 84. The delivery tips 1837a,b include a plurality of ports 1838 for delivery of a composition there through into the thin walled section 83. The desired treatment zone 1839 is shown substantially within the thin walled section 83.

FIG. 18H shows a plurality of boluses 1841 after injection by the delivery tool 1835 of FIG. 18G after the tool has been retracted from the thin walled section 83. One or more active elements of the composition have diffused into the adjacent tissues to form a local treatment zone 1843 within the thin walled section 83 but without substantially affecting the adjacent structure 84. In aspects, the local treatment zone 1843 is the region into which the initial boluses 1841 will migrate after injection into the local tissues. The extent of the local treatment zone 1843 is determined by the properties of the composition delivered, the local tissue properties, and the like.

FIG. 18I illustrates a delivery tool 1850 biased 1852 against a thin walled section 85, the delivery tool 1850 including a plurality of ports 1853 arranged thereupon such that the ports 1853 are in intimate contact with the thin walled section 85 upon biasing 1852 the device there against. The thin walled section 85 is near to an adjacent structure 86 for which treatment is not desired (treatment may generally be desired in the treatment zone 1846).

FIG. 18J shows the delivery tool 1850 after delivery of a bolus 1855 of a composition in accordance with the present disclosure to the interface between the ports 1853 and the thin walled section 85. The tool 1850 may be held against the tissues for a period of time, such that the composition may treat the tissues, such that one or more components of the composition may diffuse into the tissues, etc.

FIG. 18K shows the thin walled section 85 and a treated zone 1857 substantially in the desired treatment zone 1846, having treated the thin walled section 85 without substantially affecting the adjacent structure 86.

FIG. 18L illustrates a delivery tool 1860 with a deployable fixture 1862, the deployable fixture 1862 shaped like an inverted umbrella, a suction cup, etc. the deployable fixture 1862 shown after deployment 1863 within a lumen of a body, the deployable fixture biased against a thin walled section 87. The thin walled section 87 includes a desired treatment zone 1865 substantially residing within the thin walled section 87 and outside of the margins of an adjacent structure 88. The delivery tool 1860 is shown with a bolus 1868 of a composition in accordance with the present disclosure biased against the thin walled structure 87 so as to form a treatment zone 1867 substantially aligned with the desired treatment zone 1865.

FIG. 18M shows a delivery tool 1870 with a deployable fixture 1872 deployed and biased 1874 against a thin walled section 89. The delivery tool 1870 includes a lumen in which a vacuum 1877 has been formed so as to draw a section of the thin walled structure 89 onto one or more delivery tips 1879 in accordance with the present disclosure. After interfacing the delivery tips 1879 with the thin walled structure 89, one or more boluses 1881 of a composition in accordance with the present disclosure may be injected into the section for treatment thereof. In aspects, the delivery tips 1879 or deployable fixture 1872 may include one or more sensors, electrodes, etc. 1883 to record electrophysiological activity, detect contact with the wall, monitor delivery of the boluses 1881 into the thin walled section 89, monitor the resulting treatment process, monitor changes in electrophysiological activity in the adjacent tissues, etc.

FIG. 18N shows the thin walled section 89 and the adjacent structure 90 with the embedded boluses 1881 of composition, the composition forming a treatment zone 1885 substantially within the thin walled section 89.

Some non-limiting examples of agents suitable for performing a stress test (i.e., stressing agents), include a vasodilator, a vasoconstrictor, a neuroblocker, a neurostimulant, a neural antagonist, a neural agonist, an inverse agonist, a diuretic, insulin, glucose, beta-adrenergic receptor antagonist, angiotensin-ll converting enzyme inhibitor, calcium channel blocker, an HMG-CoA reductase inhibitor, digoxin, an anticoagulant, a diuretic, a beta blocker, an ACE inhibitor, a steroid, a combination thereof, or the like.

Sensory fibers tend to run with the SNS but may also run with the PNS (parasympathetic) plexuses although many PNS afferents are used to adjust heart function, and may not likely signal pain directly (i.e., afferent traffic may convey more than simply a local stretch-based pain response).

If sufficient care is not given to limiting medial damage during a procedure, excessive damage to the media of a coronary artery may drive neointimal thickening and stenosis following the procedure. In aspects, ablation modalities such as RF ablation may cause significant trauma to the media during a procedure, and may therefore accelerate restenosis of the vessel after the procedure. The methods provided in accordance with the present disclosure may minimize medial damage and thus provide a means for affecting neural traffic without accelerating restenosis of the vessel.

Generally speaking, the goals of such procedures are: (1) to find suitable target sites, to direct and confirm therapy with sensing devices; (2) to augment neural traffic without damaging the media; and (3) to establish the augmented neural traffic with minimal inflammatory volume.

It will be appreciated that additional advantages and modifications will readily occur to those skilled in the art. Therefore, the disclosures presented herein and broader aspects thereof are not limited to the specific details and representative embodiments shown and described herein. Accordingly, many modifications, equivalents, and improvements may be included without departing from the spirit or scope of the general inventive concept as defined by the appended claims and their equivalents.

What is claimed is:

1. A guidewire comprising:
    an elongate body dimensioned for insertion into a lumen within a body; and
    one or more sensing tips electrically and mechanically coupled to the elongate body, configured to interface with a wall of the lumen, the one or more sensing tips configured to convey one or more electrophysiologic signals associated with an electrophysiological activity in a vicinity of an anatomical site of interest within a vicinity of the lumen;
    a guide tip;
    one or more guide rings configured to slidingly engage with the guide tip; and
    a floating cage coupled with the one or more guide rings, the floating cage comprising one or more sensing elements of the one or more sensing tips;
    wherein the guidewire is configured to monitor the electrophysiological activity.

2. The guidewire in accordance with claim 1, wherein at least one of the one or more sensing tips comprises a sensor configured to measure one or more electrophysiological signals related to at least one of water concentration, tone, evoked potential, remote stimulation of nervous activity, an electromyographic signal, a mechanomyographic signal, a local field potential, an electroacoustic event, vasodilation, vessel wall stiffness, muscle sympathetic nerve activity, central sympathetic drive, tissue tone, nerve traffic, a smooth muscle action potential, and an extracellular action potential.

3. The guidewire in accordance with claim 1, wherein at least one of the one or more sensing tips is dimensioned and configured for placement into a cardiac vessel.

4. The guidewire in accordance with claim 1, further comprising a microcircuit, the microcircuit comprising one or more high fidelity amplifiers and one or more secondary amplifiers each coupled with one or more corresponding sensing tips or secondary sensors.

5. The guidewire in accordance claim 1, further comprising an analog to digital converter and a digital communication module configured to communicate one or more signals in a digital form along the guidewire during use.

6. The guidewire in accordance with claim 1, further comprising a microcircuit and at least one of one or more amplifiers and one or more analog to digital converters, the microcircuit being configured to multiplex signals from the one or more sensing elements of the floating cage and said at least one of the one or more amplifiers and the one or more analog to digital converters.

7. The guidewire in accordance with claim 1, further comprising a reference electrode, at least one of the one or more electrophysiologic signals amplifiable with respect to a potential of the reference electrode.

8. The guidewire in accordance with claim 1, further comprising a therapeutic delivery module, the therapeutic delivery module being configured to at least one of deliver radiofrequency energy, thermal energy, ultrasound energy, and a substance in the vicinity of the anatomical site of interest.

9. The guidewire in accordance with claim 1, further comprising a stimulating electrode, the stimulating electrode being configured so as to interface with tissues in the vicinity of the anatomical site of interest.

10. The guidewire in accordance with claim 1, wherein the guidewire comprises one or more electrodes electrically and mechanically coupled with the elongate body, the one or more electrodes being configured to deliver energy to the anatomical site of interest.

11. The guidewire in accordance with claim 1, wherein the guidewire comprises one or more microneedles slidingly coupled with the elongate body, the one or more microneedles being configured so as to be deployed beyond the elongate body into the anatomical site of interest.

12. The guidewire in accordance with claim 11, wherein at least one of the one or more microneedles comprises a lumen through which a substance may be delivered to the anatomical site of interest.

13. The guidewire in accordance with claim 12, wherein the substance comprises at least one of a neurotoxin, a cancer treating agent, a neuroblocking agent, a neurostimulating agent, a neurodepressant, a vasodilator, a vasoconstrictor, glucose, and insulin.

14. The guidewire in accordance with claim 11, wherein at least one of the one or more microneedles comprises one or more electrodes for at least one of sensing, stimulating, and ablating the anatomical site of interest.

15. The guidewire in accordance with claim 1, wherein the floating cage comprises an expandable cage, the expandable cage comprising a plurality of microwires, each microwire of the plurality of microwires being insulated from each other microwire in the plurality of microwires, each microwire in the plurality of microwires having at least one exposed region providing one of the one or more.

16. The guidewire in accordance with claim 1, further comprising one or more stops coupled to the guide tip, the one or more stops defining a range over which the floating cage may travel.

17. The guidewire in accordance with claim 1, wherein at least one of the one or more guide rings comprises an electronics housing comprising a microcircuit.

18. The guidewire in accordance with claim 17, further comprising a bridge electrically and physically coupled to the microcircuit embedded in the electronics housing via a flexible interconnect.

19. The guidewire in accordance with claim 17, wherein said at least one of the one or more guide rings is electrically coupled to the one or more sensing elements of the floating cage.

20. The apparatus in accordance with claim 17, wherein movement of the floating cage is limited by a size and positioning of said at least one of the one or more guide rings.

* * * * *